United States Patent
Bui et al.

(10) Patent No.: US 6,579,242 B2
(45) Date of Patent: Jun. 17, 2003

(54) METHOD AND APPARATUS FOR PROVIDING PATIENT CARE

(76) Inventors: Tuan Bui, 14436 Greenfield Ct., Green Oaks, IL (US) 60048; Emil S. Macha, 107 Sorrento, Sugar Land, TX (US) 77478; Shan Padda, 1901 N. Clybourn Ave., Chicago, IL (US) 60614; Arthur Schulze, 1819 Half Moon Dr., Wharton, TX (US) 77488; Thomas G. Cooper, 210 Charleston Dr., Friendswood, TX (US) 77546; Clint Deckert, 15518 Markar Rd., Poway, CA (US) 92064; Doron Levitas, 1817 N. Wolcott Ave., Chicago, IL (US) 60622

( * ) Notice: Subject to any disclaimer, the term of this patent is extended or adjusted under 35 U.S.C. 154(b) by 0 days.

(21) Appl. No.: 10/035,631

(22) Filed: Nov. 9, 2001

(65) Prior Publication Data

US 2002/0138017 A1 Sep. 26, 2002

Related U.S. Application Data

(62) Division of application No. 09/219,664, filed on Dec. 23, 1998.

(51) Int. Cl.$^7$ ................................. A61B 5/00
(52) U.S. Cl. .................. 600/537; 600/529; 600/549
(58) Field of Search .................. 600/537, 538, 600/529, 549

(56) References Cited

U.S. PATENT DOCUMENTS

| | | | | |
|---|---|---|---|---|
| 3,368,212 A | * | 2/1968 | Klyce | 600/538 |
| 3,739,943 A | | 6/1973 | Wilhelmson et al. | 222/59 |
| 3,858,574 A | | 1/1975 | Page | 128/205 T |
| 3,884,219 A | * | 5/1975 | Richardson et al. | 600/538 |
| 3,910,257 A | | 10/1975 | Fletcher et al. | 128/2.1 A |
| 3,962,917 A | * | 6/1976 | Tereda | 600/538 |
| 4,173,971 A | | 11/1979 | Karz | 128/702 |
| 4,413,314 A | | 11/1983 | Slater et al. | 364/188 |
| 4,449,538 A | | 5/1984 | Corbitt et al. | 128/760 |
| 4,453,552 A | * | 6/1984 | Ensign | 600/749 |

(List continued on next page.)

OTHER PUBLICATIONS

Literature describing Baxter's FLO–GARD * 6201 Volumetric Infusion Pump, copyrighte 1992.
Literature of I–Flow Corporation advertising its Vivus 4000 Infusion System.
One–page article by Jerry Hirsch entitled "Portable IV Frees Patients," printed in The Orange County Register, D section, Nov. 21, 1991.

(List continued on next page.)

Primary Examiner—Robert L. Nasser

(57) ABSTRACT

A patient management system includes a programmable patient monitor for monitoring and recording a plurality of physiological conditions of a patient, a plurality of physiological condition sensors and a communications unit. The plurality of patient monitoring sensors are electrically coupled to the programmable patient monitor. Each sensor detects a particular physiological condition of the patient, such as core temperature, ECG electrodes for providing an electrocardiogram and blood oximetry sensors. The patient monitor is small and compact and easily worn by the patient during his normal at home activities. To provide communication with a caregiver via a remote controller at the caregiver's location, a communications unit is disposed in the facility. The communications unit may be selectively coupled to the programmable patient monitor for receiving, storing and transmitting to the remote controller patient physiological condition data and for transmitting instructions from the remote controller to the programmable patient monitor. When the patient connects the patient monitor to the communications unit, the patient can communicate with the caregiver at the remote location.

2 Claims, 68 Drawing Sheets

RESPIRATION RATE ALGORITHM
PEAK DETECTION PROCESS

U.S. PATENT DOCUMENTS

| | | | |
|---|---|---|---|
| 4,531,527 A | 7/1985 | Reinhold, Jr. et al. | 128/696 |
| 4,561,443 A | 12/1985 | Hogrefe et al. | 128/419 PG |
| 4,586,260 A | 5/1986 | Baxter et al. | 33/125 C |
| 4,624,661 A | 11/1986 | Arimond | 604/151 |
| 4,676,776 A | 6/1987 | Howson | 604/31 |
| 4,696,671 A | 9/1987 | Epstein et al. | 604/67 |
| 4,731,051 A | 3/1988 | Fischell | 606/67 |
| 4,756,706 A | 7/1988 | Kerns et al. | 604/66 |
| 4,797,840 A | 1/1989 | Fraden | 364/557 |
| 4,803,625 A | 2/1989 | Fu et al. | 364/413.03 |
| 4,810,243 A | 3/1989 | Howson | 604/31 |
| 4,828,545 A | 5/1989 | Epstein et al. | 604/66 |
| 4,850,972 A | 7/1989 | Schulman et al. | 604/151 |
| 4,865,584 A | 9/1989 | Epstein et al. | 604/67 |
| 4,901,221 A | 2/1990 | Kodosky et al. | 364/200 |
| 4,925,444 A | 5/1990 | Orkin et al. | 604/80 |
| 4,933,843 A | 6/1990 | Scheller et al. | 364/413.01 |
| 4,942,514 A | 7/1990 | Miyagaki et al. | 364/190 |
| 4,952,928 A | 8/1990 | Carroll et al. | 340/825.54 |
| 4,995,268 A | 2/1991 | Ash et al. | 73/861.05 |
| 5,038,800 A | 8/1991 | Oba | 128/904 |
| 5,069,222 A * | 12/1991 | McDonald, Jr. | 600/538 |
| 5,078,683 A | 1/1992 | Sancoff et al. | 604/67 |
| 5,100,380 A | 3/1992 | Epstein et al. | 604/67 |
| 5,109,849 A | 5/1992 | Goodman et al. | 128/633 |
| 5,115,133 A | 5/1992 | Knudson | 250/341 |
| 5,116,312 A | 5/1992 | Blankenship et al. | 604/66 |
| 5,137,023 A | 8/1992 | Mendelson et al. | 128/633 |
| 5,152,296 A | 10/1992 | Simons | 128/670 |
| 5,153,827 A | 10/1992 | Coutré et al. | 364/413.02 |
| 5,155,693 A | 10/1992 | Altmayer et al. | 364/550 |
| 5,165,874 A | 11/1992 | Sancoff et al. | 417/474 |
| 5,167,235 A | 12/1992 | Seacord et al. | 128/664 |
| 5,191,891 A | 3/1993 | Righter | 128/710 |
| 5,207,642 A | 5/1993 | Orkin et al. | 604/65 |
| 5,213,099 A | 5/1993 | Tripp, Jr. | 128/633 |
| 5,226,425 A | 7/1993 | Righter | 128/710 |
| 5,230,623 A | 7/1993 | Guthrie et al. | 433/72 |
| 5,256,157 A | 10/1993 | Samiotes et al. | 604/246 |
| 5,291,190 A | 3/1994 | Scarola et al. | 340/825.06 |
| 5,295,062 A | 3/1994 | Fukushima | 364/188 |
| 5,297,554 A | 3/1994 | Glynn et al. | 128/665 |
| 5,307,263 A | 4/1994 | Brown | |
| 5,317,506 A | 5/1994 | Coutré et al. | 364/413.02 |
| 5,338,157 A | 8/1994 | Blomquist | 417/2 |
| 5,361,758 A | 11/1994 | Hall et al. | 128/633 |
| 5,368,562 A | 11/1994 | Blomquist et al. | 604/65 |
| 5,376,070 A | 12/1994 | Purvis et al. | 604/31 |
| 5,378,231 A | 1/1995 | Johnson et al. | 604/67 |
| 5,395,321 A | 3/1995 | Kawahara et al. | 604/67 |
| 5,395,329 A | 3/1995 | Fleitschhackor et al. | 604/95 |
| 5,400,246 A | 3/1995 | Wilson et al. | 364/146 |
| 5,412,400 A | 5/1995 | Takahara et al. | 345/119 |
| 5,429,602 A | 7/1995 | Hauser | 604/65 |
| 5,469,855 A | 11/1995 | Pompei et al. | 128/664 |
| 5,482,446 A | 1/1996 | Williamson et al. | 417/474 |
| 5,485,408 A | 1/1996 | Blomquist | 364/578 |
| 5,509,422 A | 4/1996 | Fukami | 128/670 |
| 5,522,396 A | 6/1996 | Langer et al. | 128/696 |
| 5,544,651 A | 8/1996 | Wilk | 128/633 |
| 5,558,638 A | 9/1996 | Evers et al. | 604/66 |
| 5,573,506 A | 11/1996 | Vasko | 604/65 |
| 5,582,593 A | 12/1996 | Hultman | 604/65 |
| 5,590,648 A | 1/1997 | Mitchell et al. | |
| 5,642,735 A * | 7/1997 | Kolbly | 600/549 |
| 5,643,212 A | 7/1997 | Coutré et al. | 604/131 |
| 5,664,270 A | 9/1997 | Bell et al. | |
| 5,724,025 A | 3/1998 | Tavori | |
| 5,873,369 A | 2/1999 | Laniado et al. | |
| 5,967,975 A | 10/1999 | Ridgeway | |
| 5,971,921 A | 10/1999 | Timbel | |
| 6,083,136 A | 7/2000 | Lisiecki | |
| 6,102,856 A | 8/2000 | Groff et al. | |
| 6,165,133 A * | 12/2000 | Rapoport et al. | 600/529 |
| 6,185,446 B1 * | 2/2001 | Carlsen, Jr. | 600/529 |

OTHER PUBLICATIONS

Chapter 5 entitled "Direct Manipulation" from Shneiderman "Designing the User Interface: Strategies for Effective Human–Computer Interaction," Addison–Wesley Publishing Company, Second Edition, © 1992, reprinted with corrections 1993.

Literature of Baxter's MultiPlex™ Series 100 Fluid Management System, 2 pp., no date listed.

Literature of Baxter "Introducing MultiPlex™ Series 100 Fluid Management System," copyright 1988.

J. C. Crone, Jaromir Belic and Roger W. Jelliffe, M.D., "A Programmable Infusion Pump Controller," taken from 30th Annual Conference on Engineering in Medicine and Biology, Nov. 5–9, 1977; pp. A–35827 through A–35837.

Selective portions of Chapter 9 of Mayhew, "Principles and Guidelines in Software User Interface Design," Prentice Hall PTR, Englewood Cliffs, New Jersey, 1992.

Electronic's Article of Feb., 1990, by Jack Shandle, entitled "Who Will Dominate the Desktop in the '90's" pp. 48–50.

"Block Medical: Growing With Home Infusion Therapy," taken from INVIVO, The Business and Medicine Report, Apr., 1991: pp. 7–9.

"IEEE–488 and VXIbus Control, Data Acquistion, and Analysis . . . the Most Choices," select pages taken from National Instruments. Application Software Products and Application Software Overview, (1991) 17 pages.

"LabView˙2 User Manual; Chapter 2, The Front Panel," taken from National Instruments Corporation, Jan. 1990; pp. 1–36.

A.H. McMorris, J.L. Kelleway, B. Tapadia and E. L. Dohmann, "Are Process Control Rooms Obsolete?", taken from Control Engineering, pp. 42–47, Jul, 1971.

Abbott Laboratories, The Blue Line System, Lifecare, copyright, 1990.

L.C. Sheppard, "Computer Based Clinical Systems: Automation and Integration," taken from 39th ACEMB, Sep. 13–16, 1986; pp. 73–75.

Bedder, et al., "Cost Analysis of Two Implantable Narcotic Delivery Systems," Journal of Pain and Symptom Management, vol. 6, No. 6, Aug., 1991, pp. 368–373.

Peter Lord, Hossein Allami, Mark Davis, Raul Dias, Patrice Heck, and Robert Rischell, pp. 66–71 from book chapter entitled "MiniMed Technologies Programmable Implantable Infusion System," describing clinical trials from Nov., 1986.

"IMED≐Status™ Infusion Management System, " 6 page brochure, IMED Corporation, San Diego, CA, no date listed.

James D. Foley and Andries Van Dam "Fundamentals of Interactive Computer Graphics," selected pages from Chapters 1 and 2, Addison–Wesley Publishing Company, ©1982, reprinted with corrections 1983.

* cited by examiner

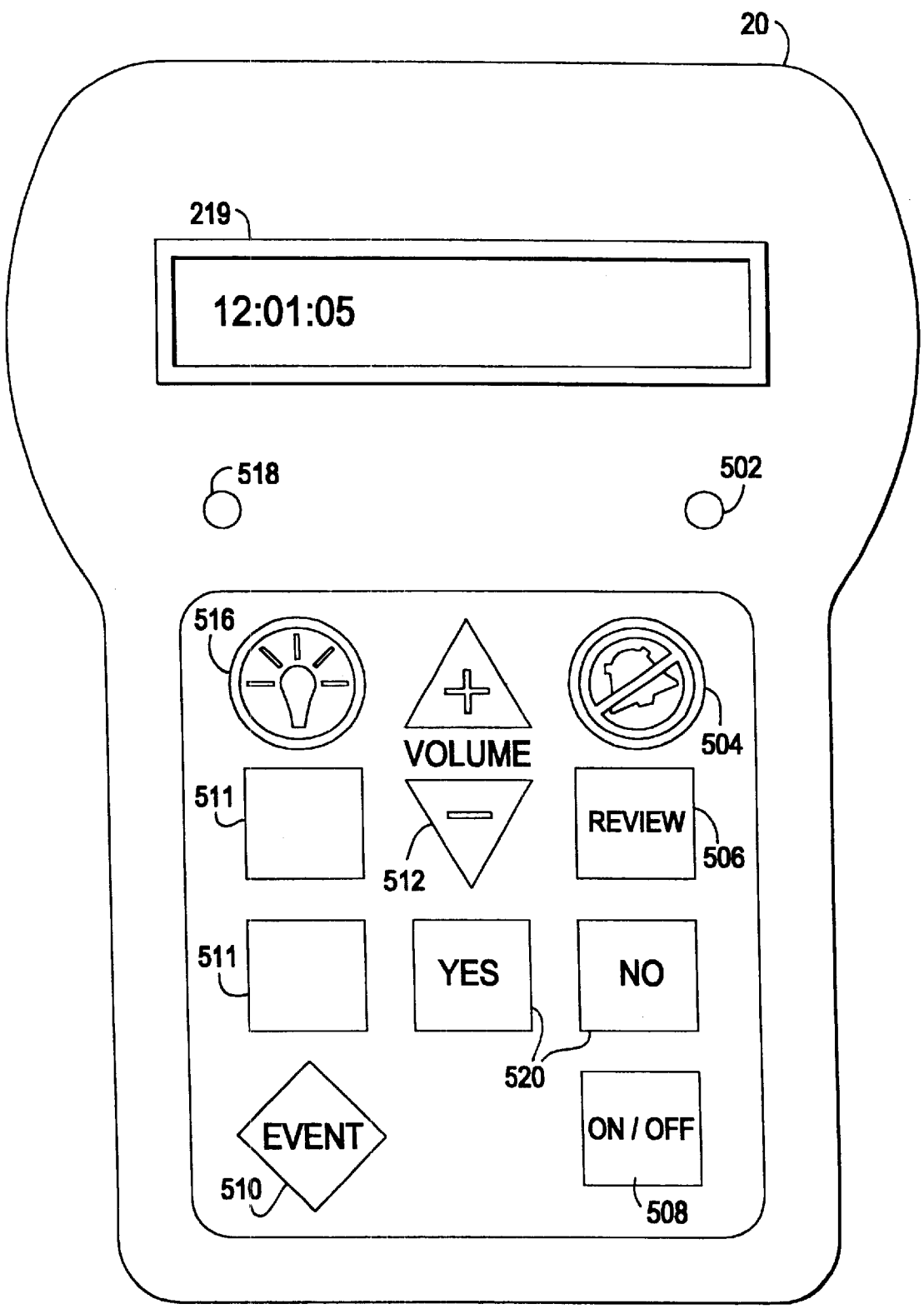

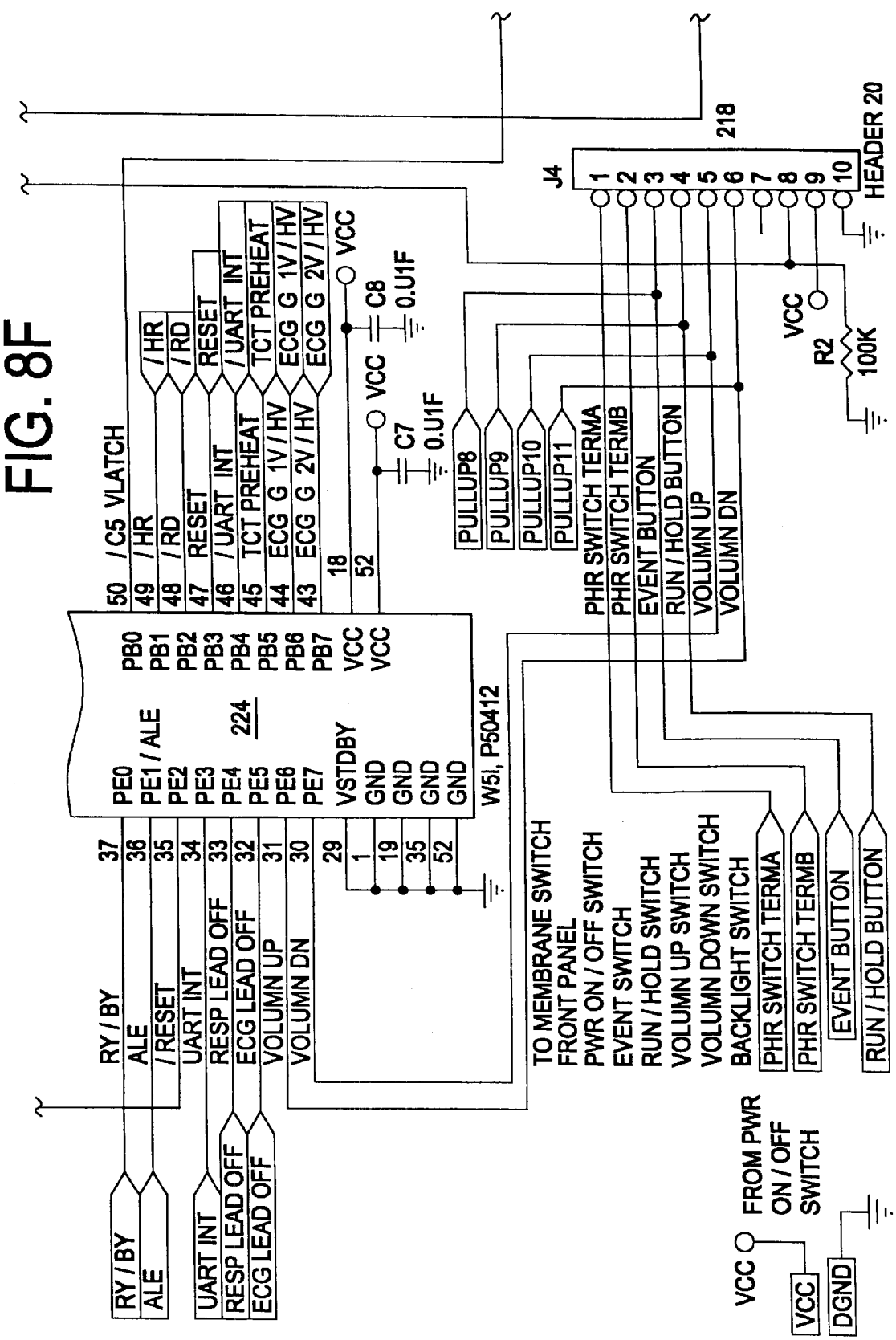

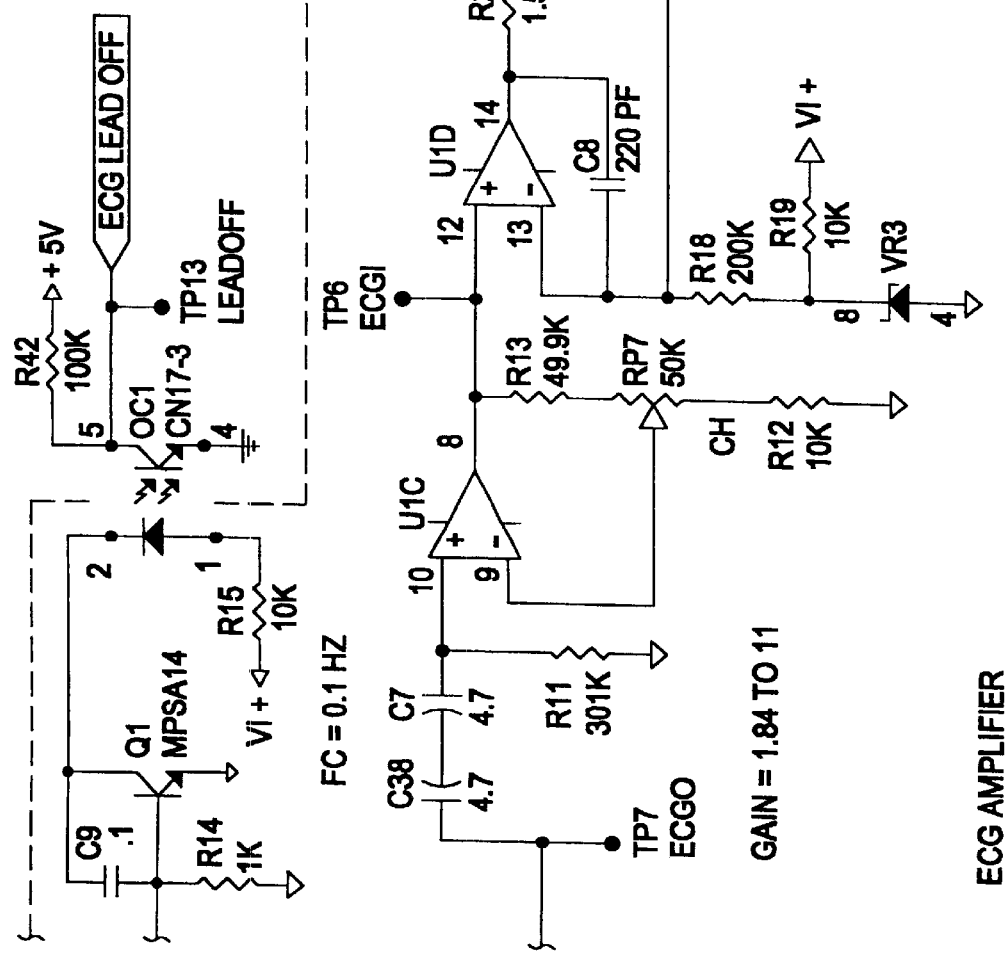
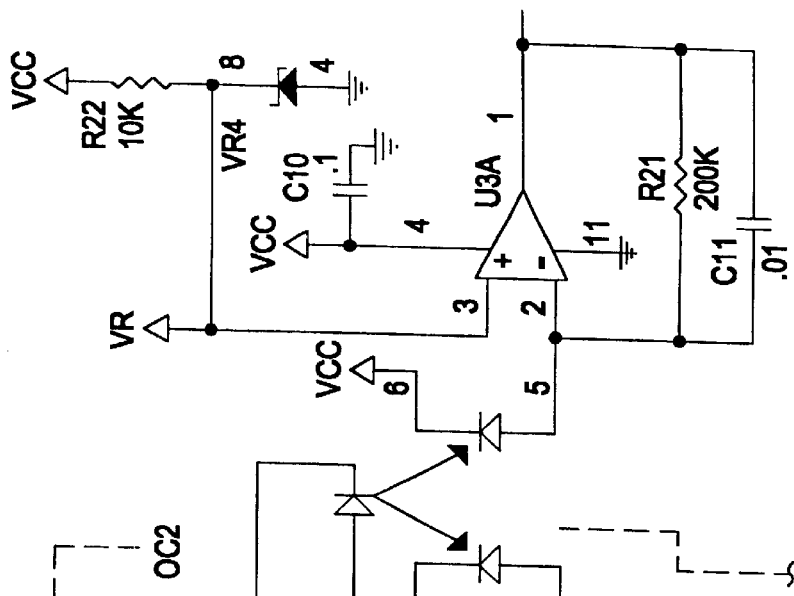
FIG. 9B

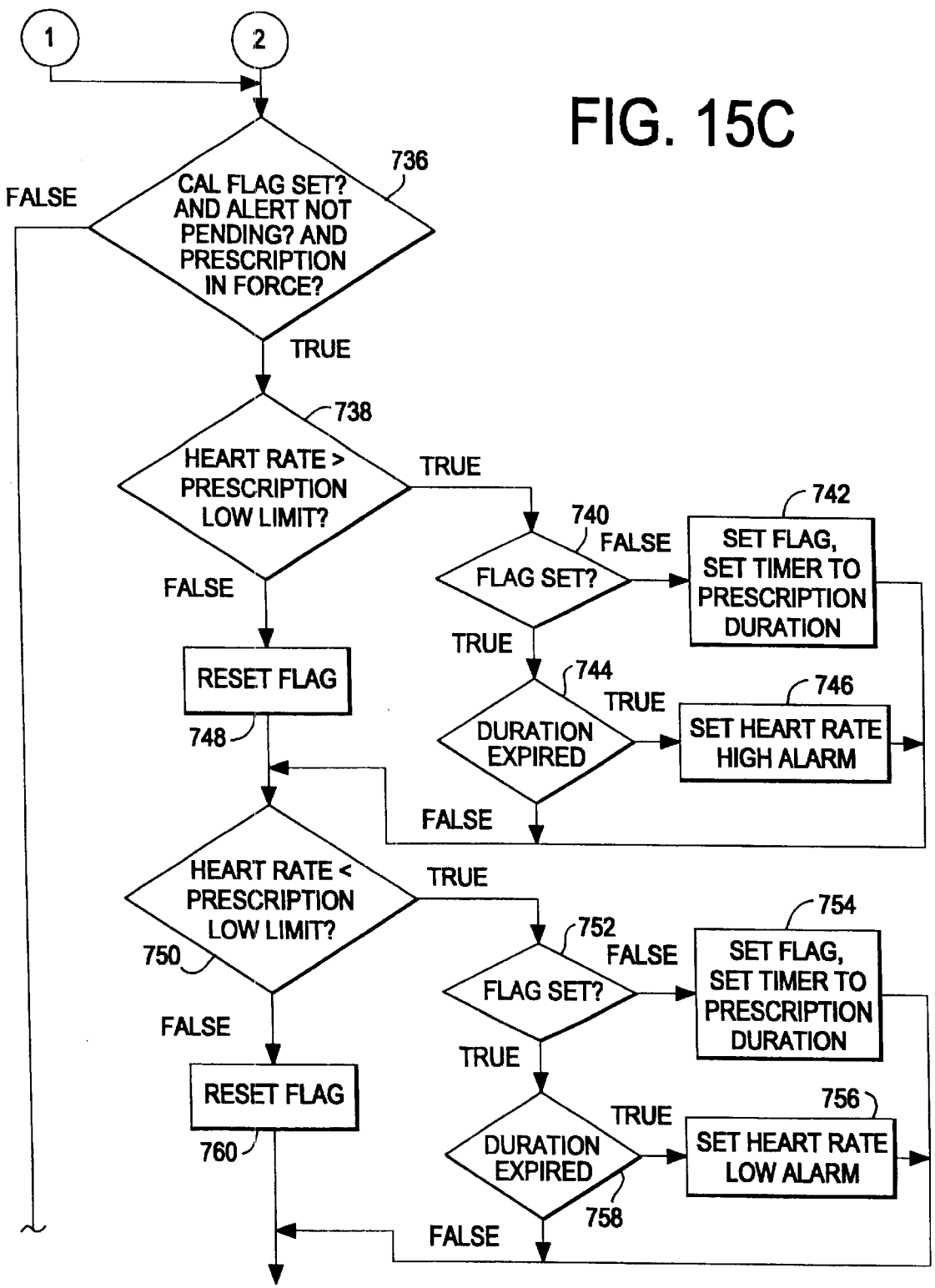

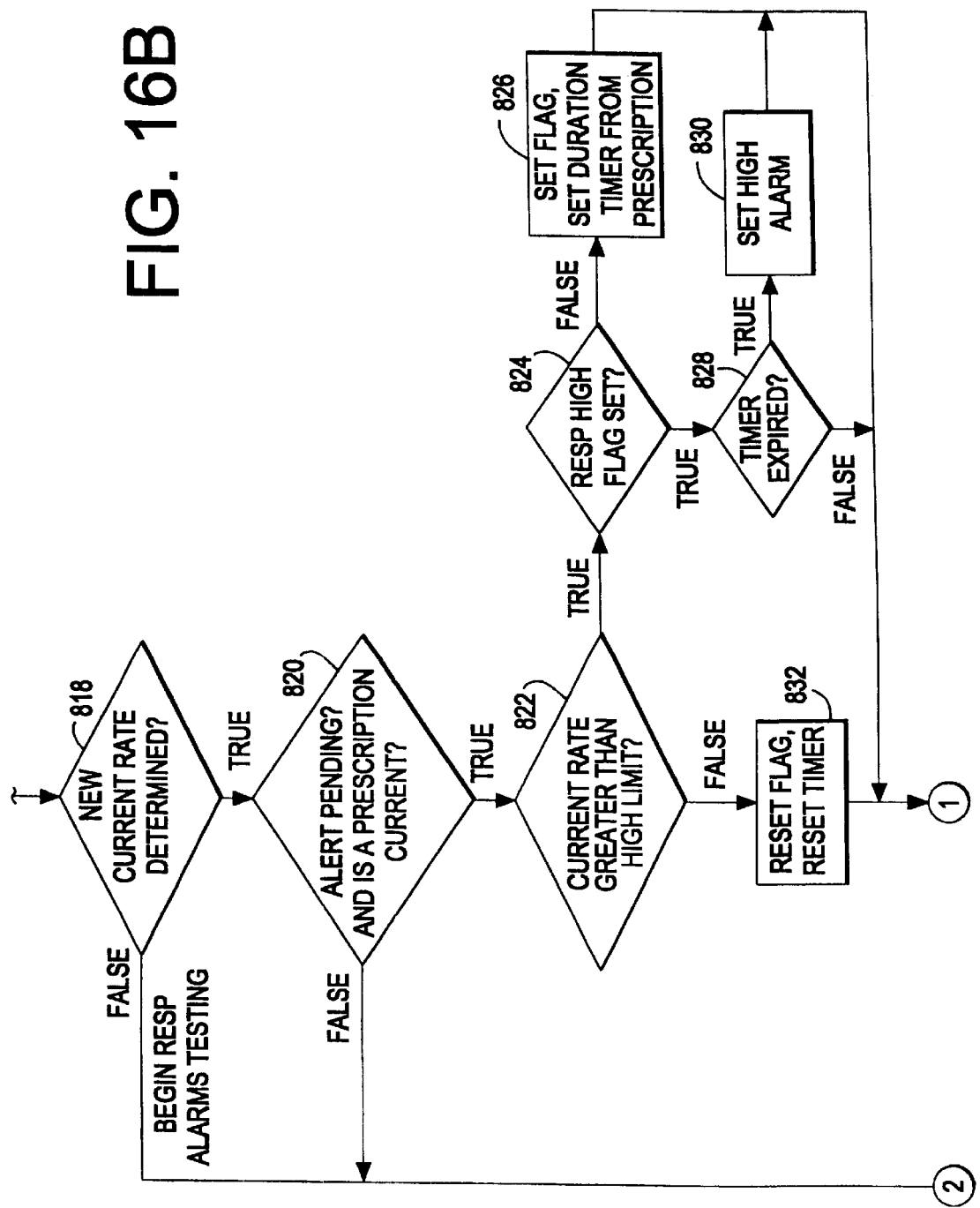

US 6,579,242 B2

METHOD AND APPARATUS FOR PROVIDING PATIENT CARE

RELATED APPLICATIONS

This is a divisional application of U.S. patent application Ser. No. 09/219,664 filed Dec. 23, 1998.

BACKGROUND OF THE INVENTION

This invention relates generally to a management system and a method of providing patient care in the home or alternate care setting, i.e., to a system which functions as a virtual hospital room.

A hospital room is a place where a patient can receive medical treatment and have his physiological condition monitored under the supervision of a healthcare professional both continuously and at prescribed times. As the cost of health care increases, the trend is to discharge the patient from the hospital earlier, but to continue the therapy at the patient's home or at an alternative care facility. Various medical devices, such as infusion pumps and respirators, allow the patient to receive therapy outside the hospital environment. In many instances the caregiver must visit the patient's home to monitor and control the medical device. Some medical devices, however, include means for enabling the caregiver (or healthcare professional) to monitor and control the medical device's functions from a remote location.

Co-pending U.S. patent application Ser. No. 08/951,976, filed Oct. 16, 1997, titled "Medical Apparatus With Remote Virtual Input Device", which is assigned to the assignee of this application, describes a medical apparatus for remote monitoring and controlling of a medical treatment device, such as an infusion pump. The medical apparatus described therein includes a medical device for administering a medical treatment and a remote controller. The caregiver can control operation of the medical device either at the patient's location using the device's input device or from the remote location by activating a virtual input device.

U.S. Pat. No. 5,807,336 for "Apparatus for Monitoring and/or Controlling a Medical Device", which is assigned to the assignee of this application, describes an apparatus for remotely monitoring and controlling a medical device in which stored data can be transferred from the medical device on a real-time basis to the remote controller while the medical device is administering medical treatment.

Co-pending U.S. patent application Ser. No. 08/703,543, filed Aug. 27, 1996, titled "Medical Treatment Apparatus and Method", which is assigned to the assignee of this application, describes a combination of a medical treatment device, such as an infusion pump, and one or more sensors, which detect the medical condition of the patient. The sensors are connected to the medical treatment device, so that signals generated by the sensors, which indicate the patient's medical condition, can be stored as data in a memory contained within the medical treatment device. By connecting the sensors directly to the medical treatment device, such data can be safely stored within the device for later downloading by a remote monitor/controller. The use of such sensors during the administration of a treatment, however, may limit the patient's mobility.

U.S. Pat. No. 5,522,396 to Langer et al. discloses a remote system for monitoring a patient's heart. A patient station, which is intended to be worn by the patient, includes a monitor for monitoring a patient's heart or other physiological function and a transmitter for transmitting data. The patient station, however, does not provide for alarms should the patient's condition require contacting the caregiver.

U.S. Pat. No. 5,590,648 to Mitchell et al. discloses a unitary command center (generally resembling a cart) having a computer for receiving, storing, processing and transmitting information, and a plurality of interfacing ports. Various patient monitoring sensors modules and therapy modules are intended to be connected to the ports. However, the command center is suitable for an ambulatory patient.

U.S. Pat. No. 5,678,562 to sellers discloses an ambulatory physiological monitor intended for Holter monitoring with a removable disk cartridge and a wireless modem. Transmitting data over a cell phone system is costly and not all patients may be capable of using the removable disk cartridges.

U.S. Pat. No. 5,568,814 to Gallant et al. discloses an ambulatory patient monitoring system for measuring and storing predetermined diagnostic parameters of a patient. One or more plug-in sensor units is coupled to a portable portion of the system, which is worn by the patient. The portable portion is designed to be coupled to a personal computer for programing, downloading and monitoring of the data, but does not provide for alarms should the patient's condition be outside prescribed values.

In addition to providing therapy at home or in the alternative care facility, many patients may still need monitoring of their physiological conditions. Some patients may require continuous monitoring of respiration and heart rate, for example. Other patients may only need their vital signs, such as temperature, blood pressure, heart rate, taken at scheduled times or when a caregiver requests the measurements, such as for diagnosis.

There is a need for a patient home management system which provides for continuous monitoring of physiological conditions of an ambulatory patient. There is a need for a lightweight, easy to wear patient monitor for an ambulatory patient, which can be configured to accept a wide variety of diagnostic and monitoring sensors. There is a need for an ambulatory patient monitor which is versatile, but not unnecessarily complex. There is a need for a patient home management system which provides for measurement of a patient's vital signs on a regular schedule or at the direction of a caregiver at a remote location. There is a need for a patient home management system which provides for ease of communication with the caregiver. There is a need for a patient home management system which provides for the storage and transmission of patient physiological condition data. There is also a need for a patient home management system which monitors the patient's condition and when the patient's physiological condition falls outside prescribed limits, provides a means of notifying the patient to contact the caregiver or automatically contacts the caregiver. There is a further need for a patient home management system which provides for the monitoring of the various sensors used to detect the patient's physiological condition.

SUMMARY OF THE INVENTION

A patient home management system embodying the invention provides a comprehensive system for monitoring ambulatory or homebound patients in the home or alternative care environment. The patient management system includes a programmable, ambulatory patient monitor for monitoring and recording a plurality of physiological conditions of a patient. A plurality of patient monitoring sensors are electrically coupled to the programmable, ambulatory patient monitor. Each sensor detects a particular physiological condition of the patient, such as core temperature, respiration characteristics including respiration rate, electrocardiographic electrodes for providing signals to produce an electrocardiogram and blood oximetry sensors.

The ambulatory patient monitor is small and compact and easily worn by the patient during his normal at-home activities.

To provide communication with the caregiver, a communications unit is disposed in the patient's home or the alternate care facility. The communications unit includes a modem or other telecommunications device which can communicate with a remote controller at the caregiver's office. The communications unit is generally larger than the ambulatory patient monitor and is situated at a convenient location where the patient can hear or see messages from it. The communications unit may be selectively coupled to the programmable, ambulatory patient monitor for receiving, storing and transmitting to the remote controller patient physiological condition data and for transmitting instructions from the remote controller to the programmable, ambulatory patient monitor. The patient can communicate with the caregiver using the communications unit. When the patient connects the ambulatory patient monitor to the communications unit, the patient can communicate with the caregiver at the remote location while the caregiver is viewing patient stored data transmitted from the ambulatory patient monitor via the communications unit.

The communications unit may also be used to monitor physiological conditions of the patient which do not require continuous monitoring. For example, the communications unit may connect to and receive physiological signals from a spirometer, a blood gas analyzer, a non-invasive blood pressure monitor, a scale for measuring a patient's weight and a temperature sensor.

The programmable, ambulatory patient monitor includes a plurality of sensor interface circuits. Each interface circuit is coupled to a particular patient monitoring sensor. Each sensor generates a physiological signal representative of a physiological condition of the patient. The interface circuit converts the physiological signal to physiological data, which is stored in memory. When the ambulatory patient monitor is connected to the communications unit, physiological data may be downloaded to the communications unit for later transmission to the remote controller. The communications unit also transmits instructions from the remote controller to the ambulatory patient monitor. Such instructions include, for example, prescribed normal ranges for physiological condition readings and schedules for making particular physiological measurements.

The ambulatory patient monitor includes a processor which executes a monitoring routine in accordance with the instructions received from the remote controller. The monitoring routine compares the physiological conditions detected b the sensor with a stored instruction having a predetermined range of values for that particular sensor. If the detected signal is outside the predetermined range, a patient alarm signal is generated.

An alarm signal is generated when a sensor signal indicates a condition requiring intervention of the caregiver. When an alarm signal is generated, the patient must contact the caregiver. In doing so, the patient may call the caregiver directly or connect the ambulatory patient monitor to the communications unit. The communications unit will then automatically communicate with the remote controller. Alternatively, the communications unit may automatically contact the caregiver upon receipt of the alarm system. Preferably the communications unit includes voice-over-data communications capability so that the patient can speak with the caregiver while the caregiver is viewing the physiological data transmitted from the communications unit to the remote controller. The alarm signal is resettable only upon receipt of a new instruction from the remote controller. This ensures that the patient contacts the caregiver when an alarm condition is detected.

The communications unit includes apparatus for communicating with the remote controller. The apparatus for communicating with the remote controller may be a typical telephone modem or voice-over-data modem, a cable modem or some form of wireless communication such as radio frequency (RF), infrared (IR) or the like. The communications unit also includes a routine for transmitting instructions received by the programmable, ambulatory patient monitor from the remote controller and for transmitting patient physiological condition data from the programmable, ambulatory patient monitor to the remote controller.

Long-term or continuous monitoring sensors are preferably connected to the ambulatory patient monitor; short-term or single measurement sensors are preferably selectively coupled to the communications unit. Examples of sensors which may be connected to the ambulatory patient monitor include sensors such as core temperature and ECG. Sensors which measure a patient's vital signs on an infrequent or scheduled basis, such as blood pressure or weight are preferably selectively connected to the communications unit. Additional sensors for infrequent or scheduled measurements include a spirometer, a blood gas analyzer, a non-invasive blood pressure monitor and a temperature sensor. For example, if the patient's blood pressure must be taken twice a day, the communications unit will provide a signal to the patient to connect the blood pressure unit and take the measurement at the schedule times. If the caregiver prefers the patient to take a particular measurement at an unscheduled time, the remote controller can communicate directly with the communications unit, which will provide a signal to the patient to take the measurement.

Signals from the communications unit and the ambulatory patient monitor can be visual or aural. Preferably, the communications unit includes a display for providing text or graphical messages to the patient and a speaker for providing spoken messages to the patient. Tones may also be used in connection with alarm signals. Preferably, the ambulatory patient monitor includes a display for graphical or textual messaes, lamps for use in signalling of alarm conditions and a speaker for audio messages and tones. Additionally, a printer or other output device may be connected to the communications unit for displaying or printing out the stored data, either automatically or on demand.

Another function of both the ambulatory patient monitor and the communications unit is to monitor the operation of the sensors when measuring physiological conditions of the patient. If a sensor is attached improperly, an alert signal is provided. The patient can reset an alert signal, for example, by attaching the sensor properly in a timely fashion. Alert signals are generally not life-threatening and do not require contacting the caregiver, so they may be reset by the patient. However, if the alert signal is not reset within a reasonable time, the monitoring routine may issue an alarm signal.

The remote controller, located at a hospital or a caregiver's office, includes software which interacts with the communications unit via the communications apparatus (i.e., by modem and a telephone line, or by another means of communication, such as wireless or cable). The remote controller software collects data stored in the communications unit and presents the information for review by the caregiver. When connected to the communications unit, the remote controller software can also program the ambulatory patient monitor by sending it new instructions and monitor the functions of the sensors connected to the ambulatory patient monitor and to the communications unit. The remote controller software can also schedule and program (i.e., set the schedule for taking measurements and for turning them on and off) the sensors connected to the ambulatory, patient monitor and the sensors selectively connected to the communications unit.

BRIEF DESCRIPTION OF THE DRAWINGS

FIG. 4 is a top view of a programmable, ambulatory patient monitor;

FIGS. 9A–9D are a circuit diagram of the ECG interface circuit;

FIGS. 15A–15D are a flow chart of the oximetry driver and task flow in the ambulatory patient monitor;

FIGS. 16A–16E are a flow chart of the temperature and breath rate task flow in the ambulatory patient monitor;

DETAILED DESCRIPTION OF THE PREFERRED EMBODIMENT

Figure 1:
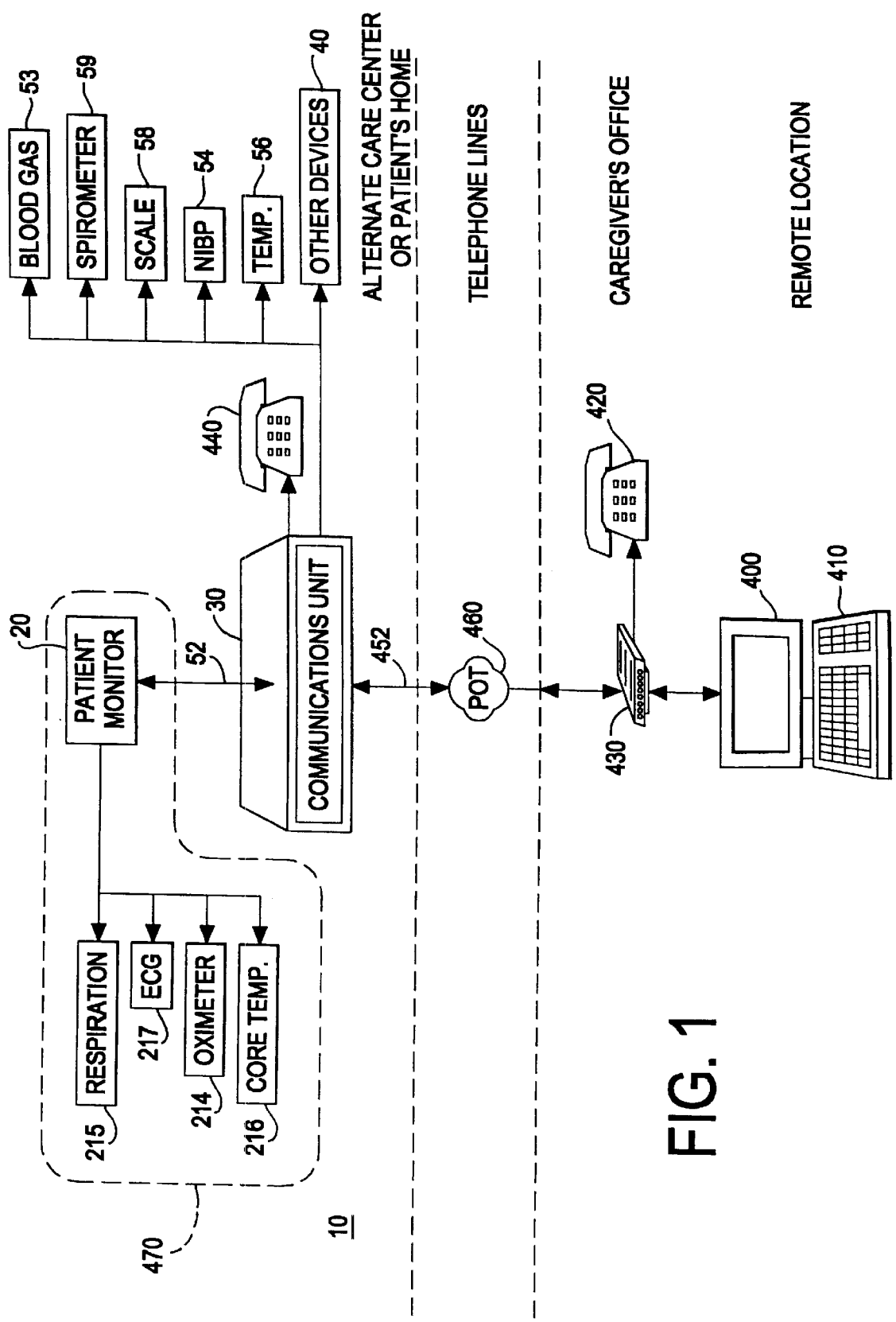
FIG. 1 is a block diagram of a patient management system according to one embodiment of the invention.

Referring now to the drawings and especially to FIG. 1, a patient home management system embodying the present invention is generally shown therein and referred to by reference numeral 10. Patient home management system 10 includes a programmable, ambulatory patient monitor, 20, to which one or more physiological sensors 214, 215, 216 and 217 are connected. Physiological sensor 214 is a pulse oximetry sensor and measures oxygen in the blood stream, sensor 215 measures respiration, sensor 216 measures core temperature and sensors 217 receiver electrocardiographic signals. Each of these sensors is intended to be worn by the patient continuously, or for several hours at a time. The physiological condition of the patient, as detected by each sensor, is stored in the ambulatory patient monitor 20.

From time-to-time, ambulatory patient monitor 20 is connected to communications unit 30 by communications medium 52, which may be a removable cable or a wireless medium (such as an IR port or RF transceiver). With medium 52 coupling monitor 20 to communications unit 30, communications unit 20 to communications unit 30, communications unit 30 can retrieve stored data representative of the patient's physiological conditions detected by sensors 214, 215, 216 and 217.

Communications unit 30 controls additional physiological sensors 53, 54, 56, 58 and 59. These additional sensors are typically used to measure physiological conditions infrequently or at specified times. Sensor 56 measures temperature and, for example, may be used to verify a temperature reading by core temperature sensor 216. Sensor 53 measures blood gas. Sensor 59 is a spirometer for measuring volume of respiratory air flow. Sensor 54 (NIBP) measures blood pressure non-invasively. A patient may only need to take his blood pressure using non-invasive blood pressure sensor 54 twice a day, for example. Sensor 58 measures the patient's weight. The patient's weight may only be needed daily or weekly by scale 58. Communications unit 30 can also monitor other devices, such as an infusion pump, or download data to a personal computer 40 located at the patient's home or alternative care facility, such as when the caregiver visits the patient.

Communications unit 30 includes a modem 31 (not shown) which is used to connect over telephone lines 460 to a caregiver at a remote location. Modem 31 may be a voice-over-data modem to enable the patient to communicate with the caregiver while the caregiver views the patient's physiological data or other wireless means of communication. The remote location, such as the caregiver's office, includes a comparable modem 430 connected to a personal computer 400 (or other stored data device or network supervisory system). Remote control software 410 operating on the computer 400 is used by the caregiver to send instructions to the communications unit 30. Some of the instructions provided by the caregiver through the remote control software 410 include setting the range of valves for the physiological sensors. A detected value outside the range for the patient causes an alarm signal, to be generated by the ambulatory patient monitor 20. Generation of an alarm signal alerts the patient to contact the caregiver, preferably by connecting the ambulatory patient monitor 20 to communications unit 30. In an alternative embodiment, the ambulatory patient monitor may include a wireless communication means such as an IR port or RF transceiver. In this alternative embodiment, the generation of the alarm signal is transmitted wirelessly to the communications unit 30, which then automatically contacts the caregiver.

Figure 2:
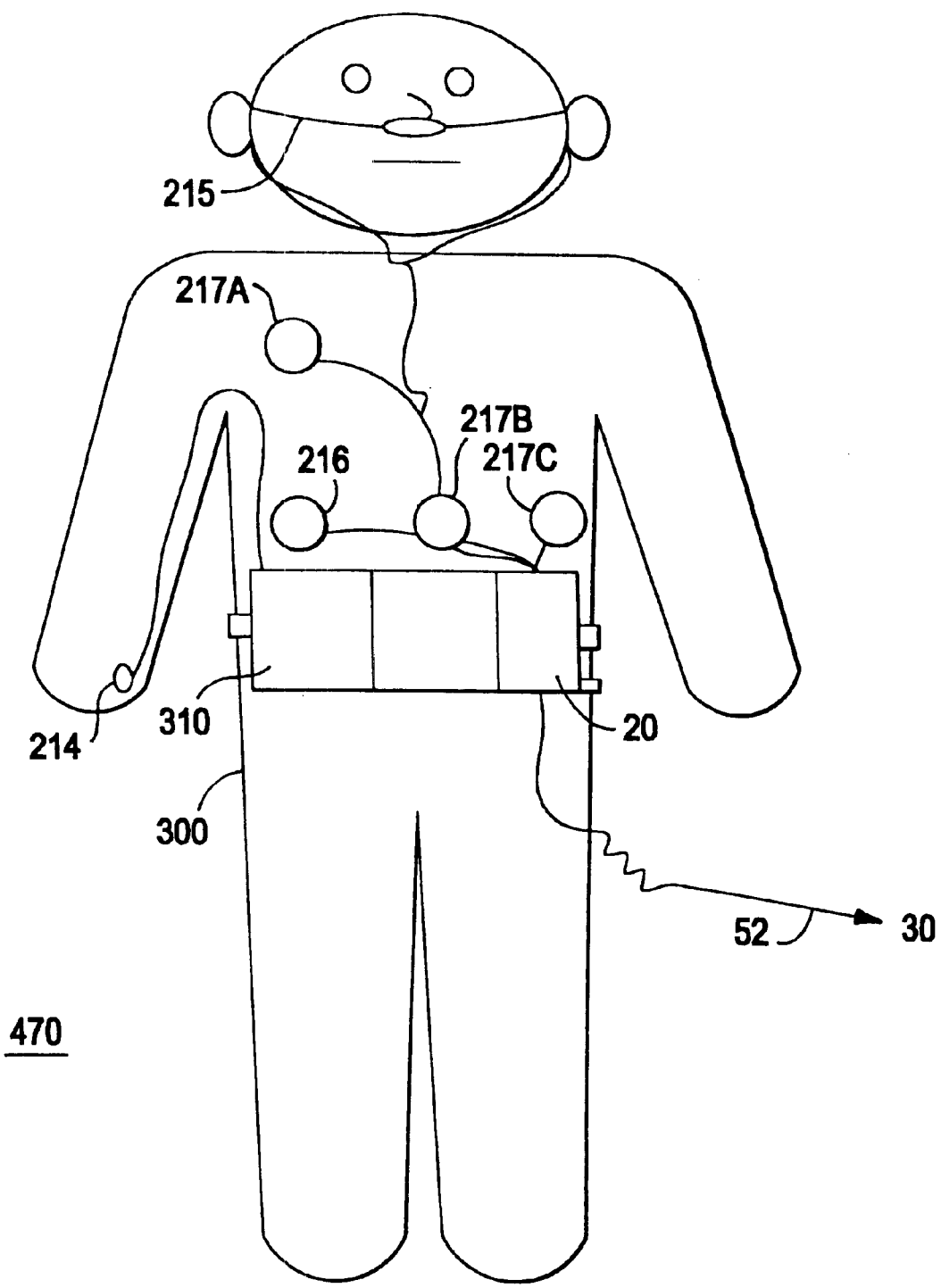
FIG. 2 is a schematic of the patient interface portion of the patient management system shown in FIG. 1.

Referring to FIG. 2, patient 300 is shown wearing programmable, ambulatory patient monitor 20 in a belt pouch 310. Respiratory sensor 215, core temperature sensor 216, pulse oximetry sensor 214 and ECG electrodes 217A, 217B and 217C are attached to patient 300 for detecting the patient's physiological condition and to monitor 20. While four sensors are shown attached to the patient, it should be noted that one, some or all of the these sensors (and any other sensors which may be required by the caregiver) may be attached to the patient and connected to the monitor 20. Detachable medium 52 is selectively attachable to monitor 20 for coupling to communications unit 30.

Figure 3A:
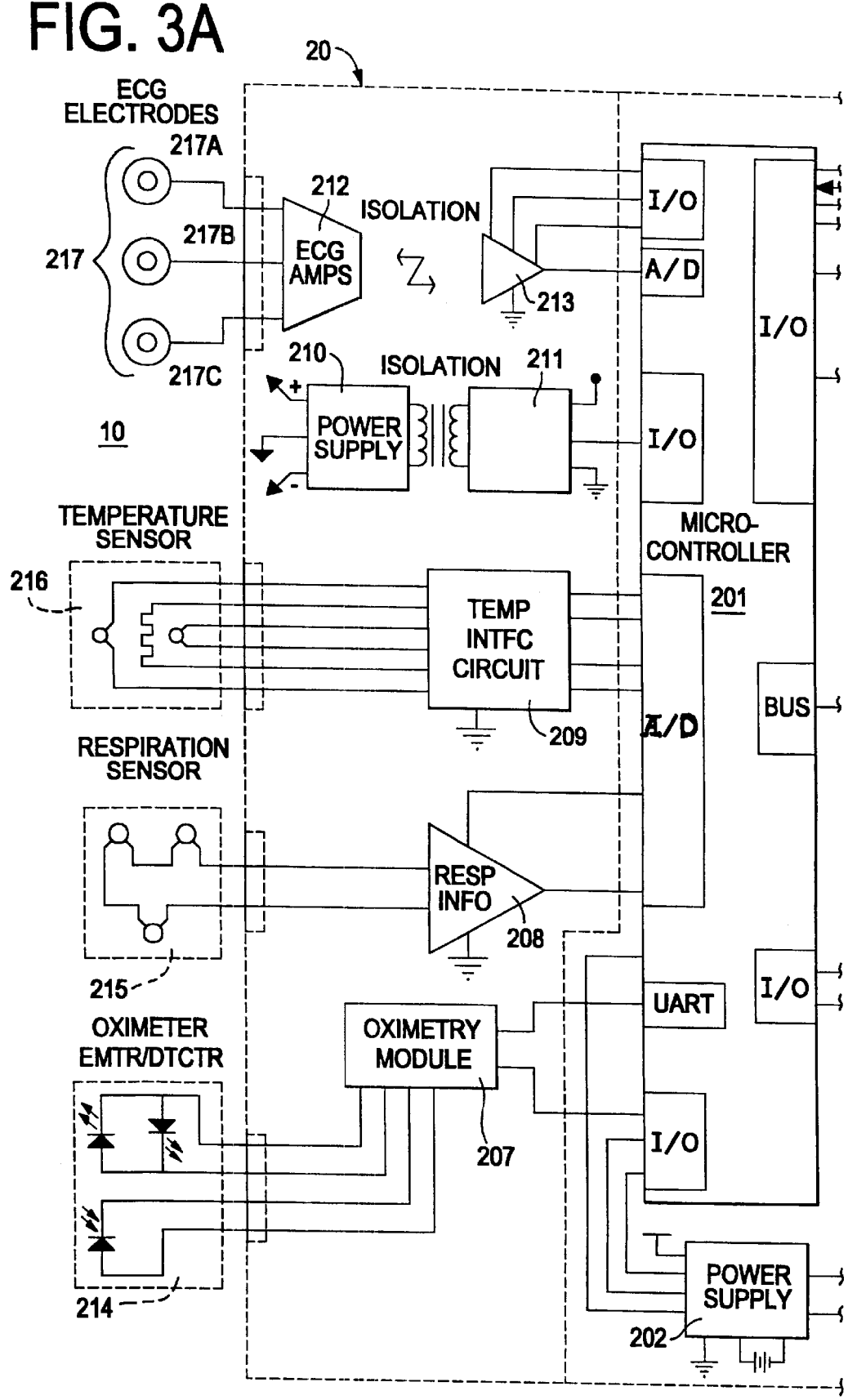
FIGS. 3A–3B are an overall schematic of the patient management system of FIG. 1.
Figure 3B:
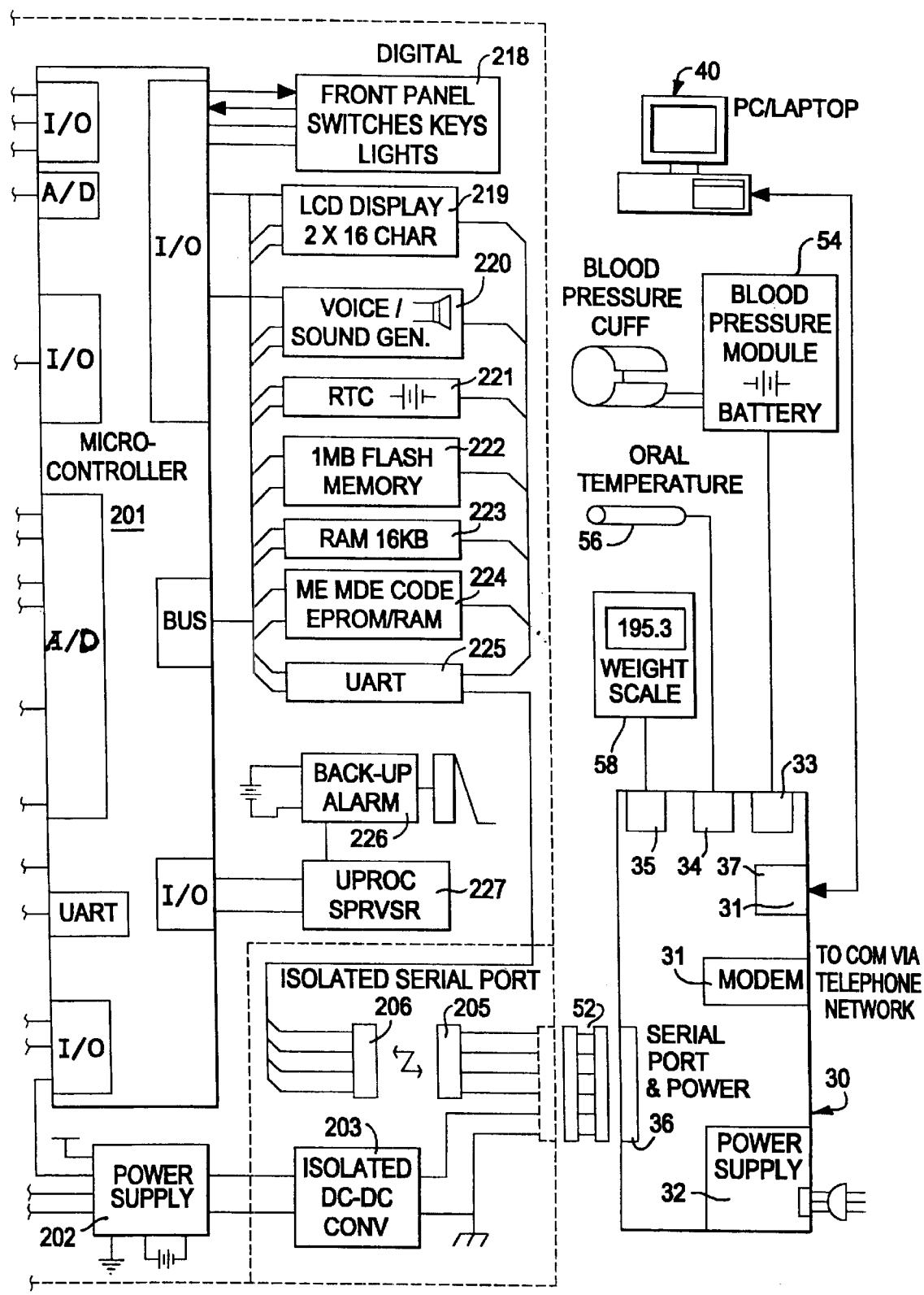
Figure 5:
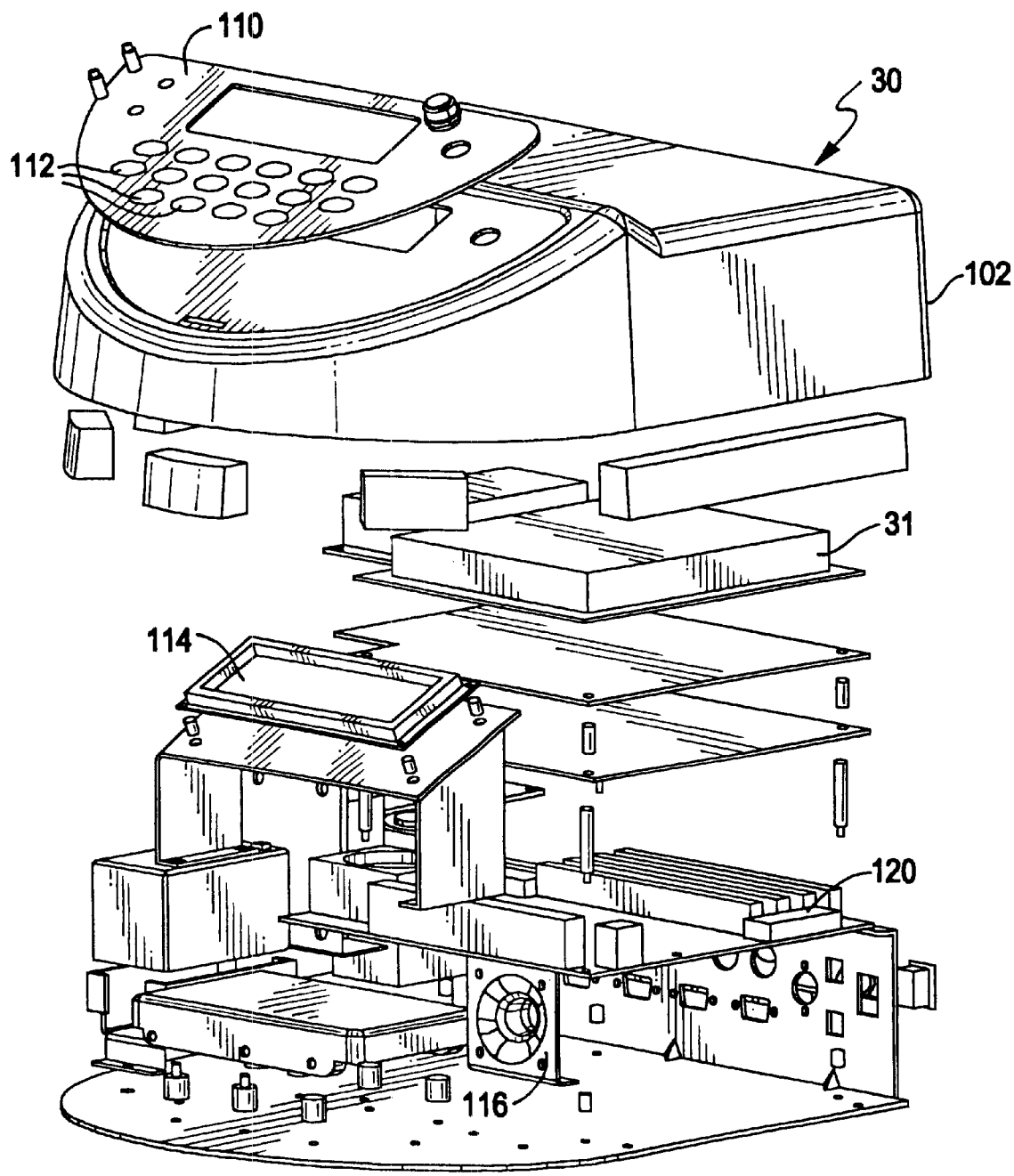
FIG. 5 is an exploded perspective view of a communications unit.
Figure 6:
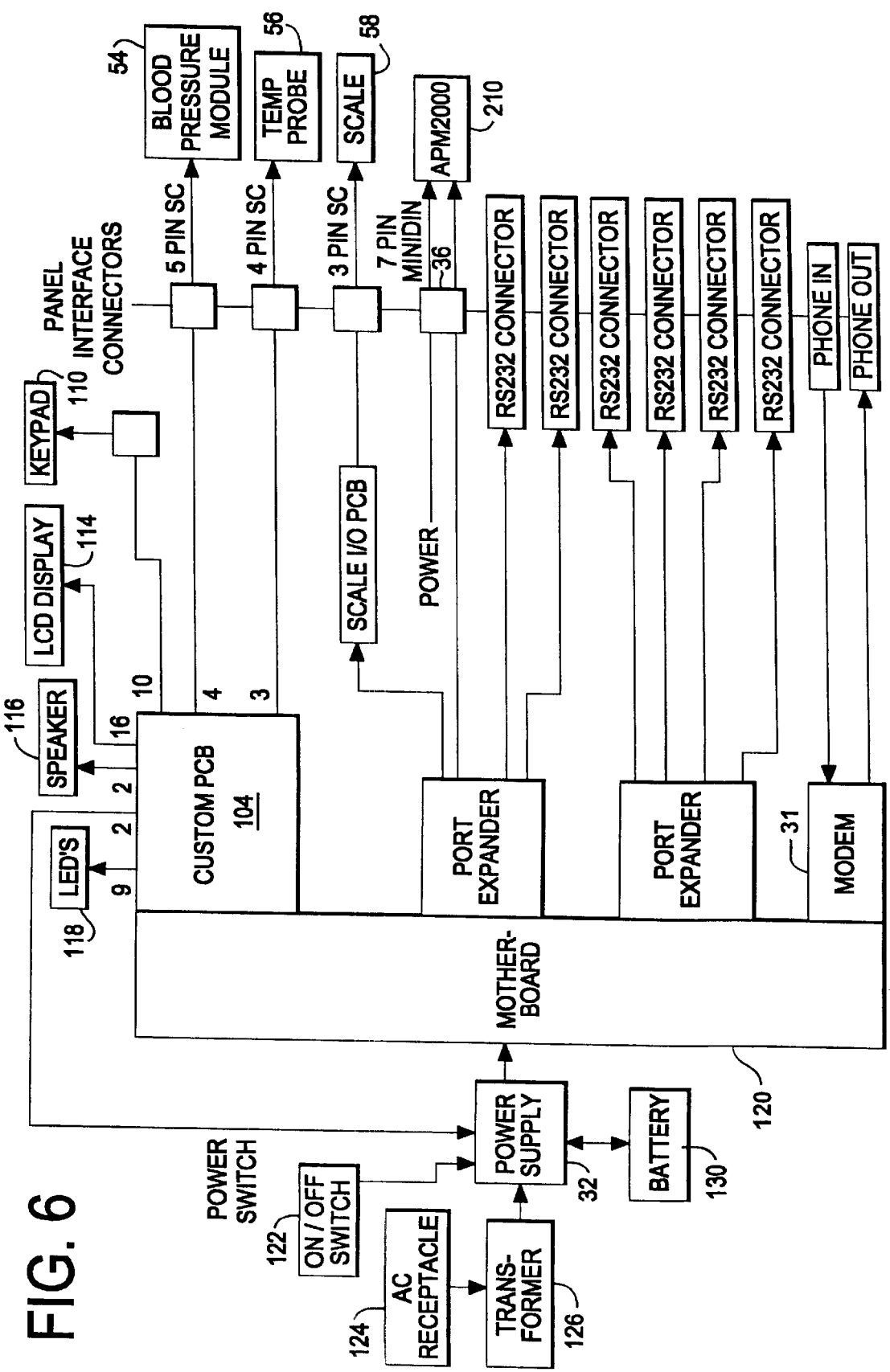
FIG. 6 is a block diagram of the electronics in the communications unit of FIG. 5.
Figure 7A:
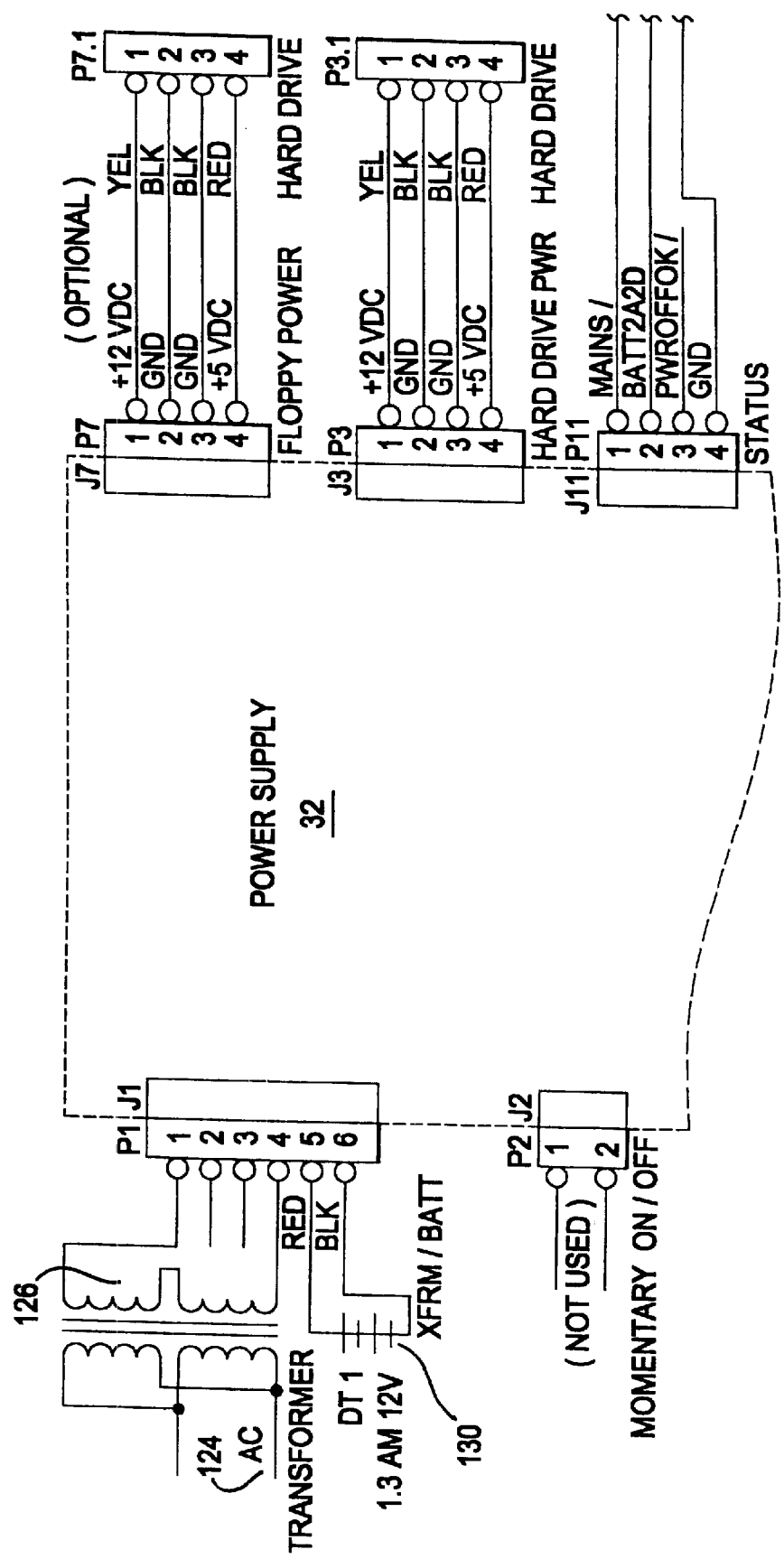
FIGS. 7A–7D are a circuit diagram showing connections among the components shown in FIG. 6.
Figure 7B:
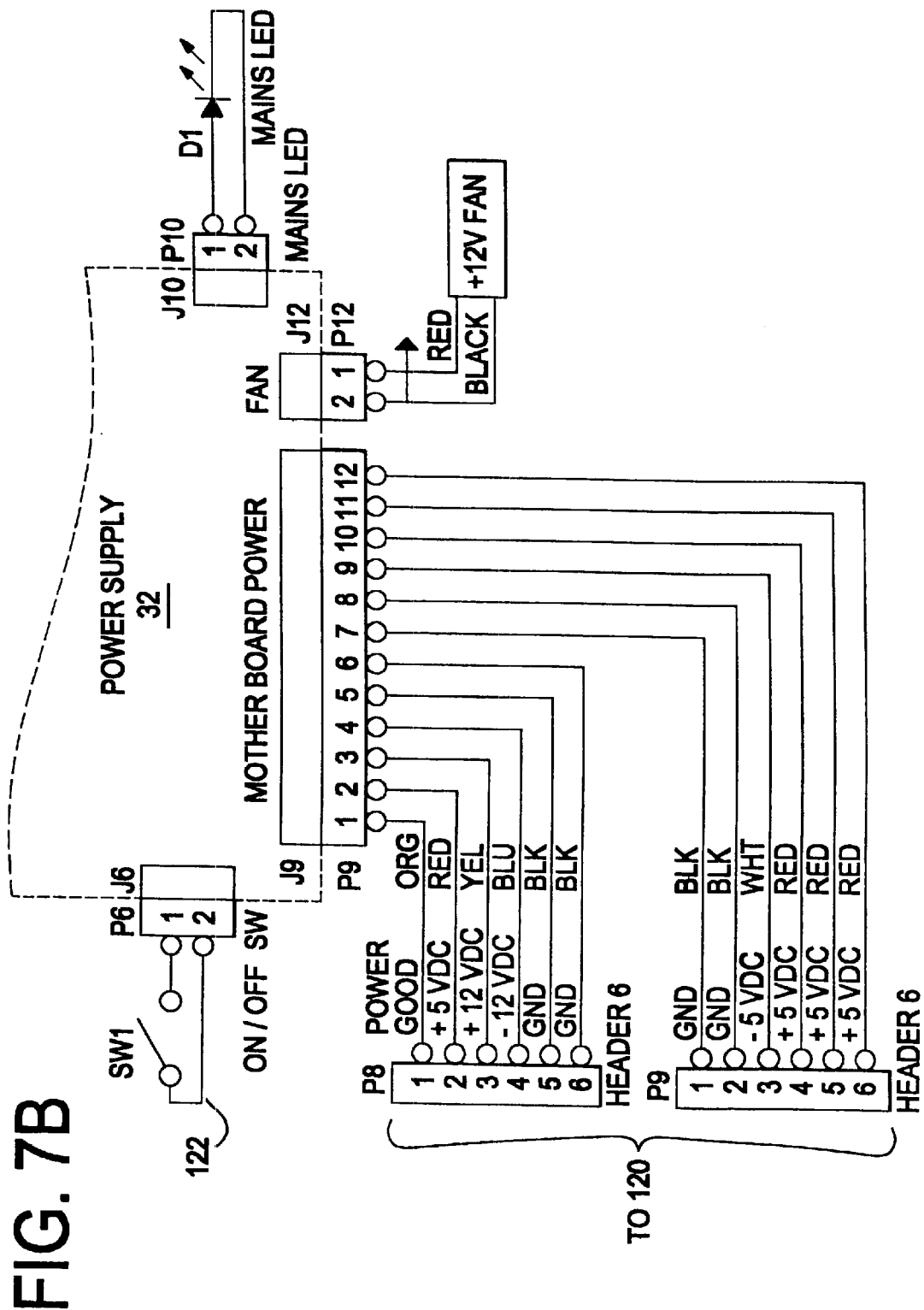
Figure 7C:
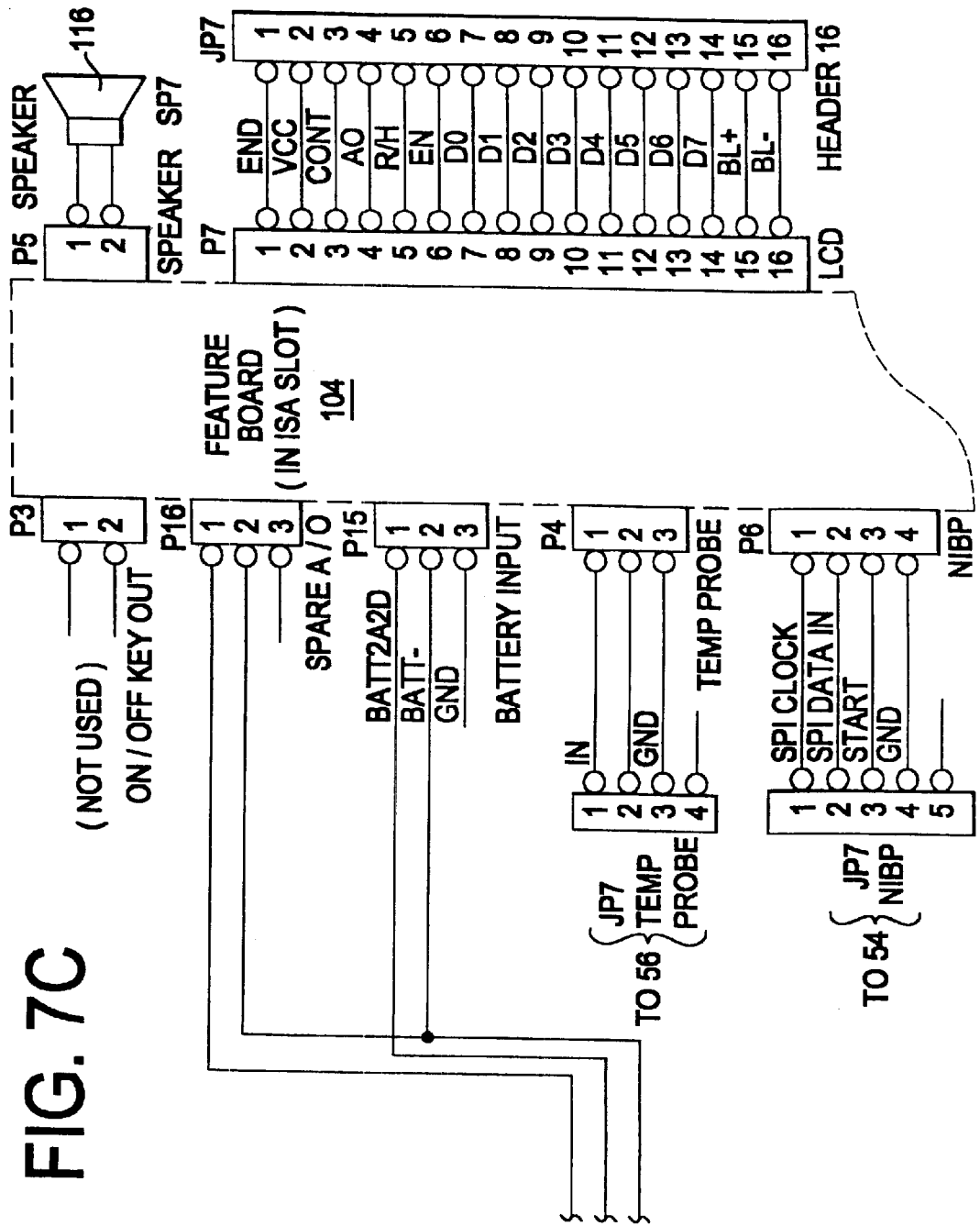
Figure 7D:
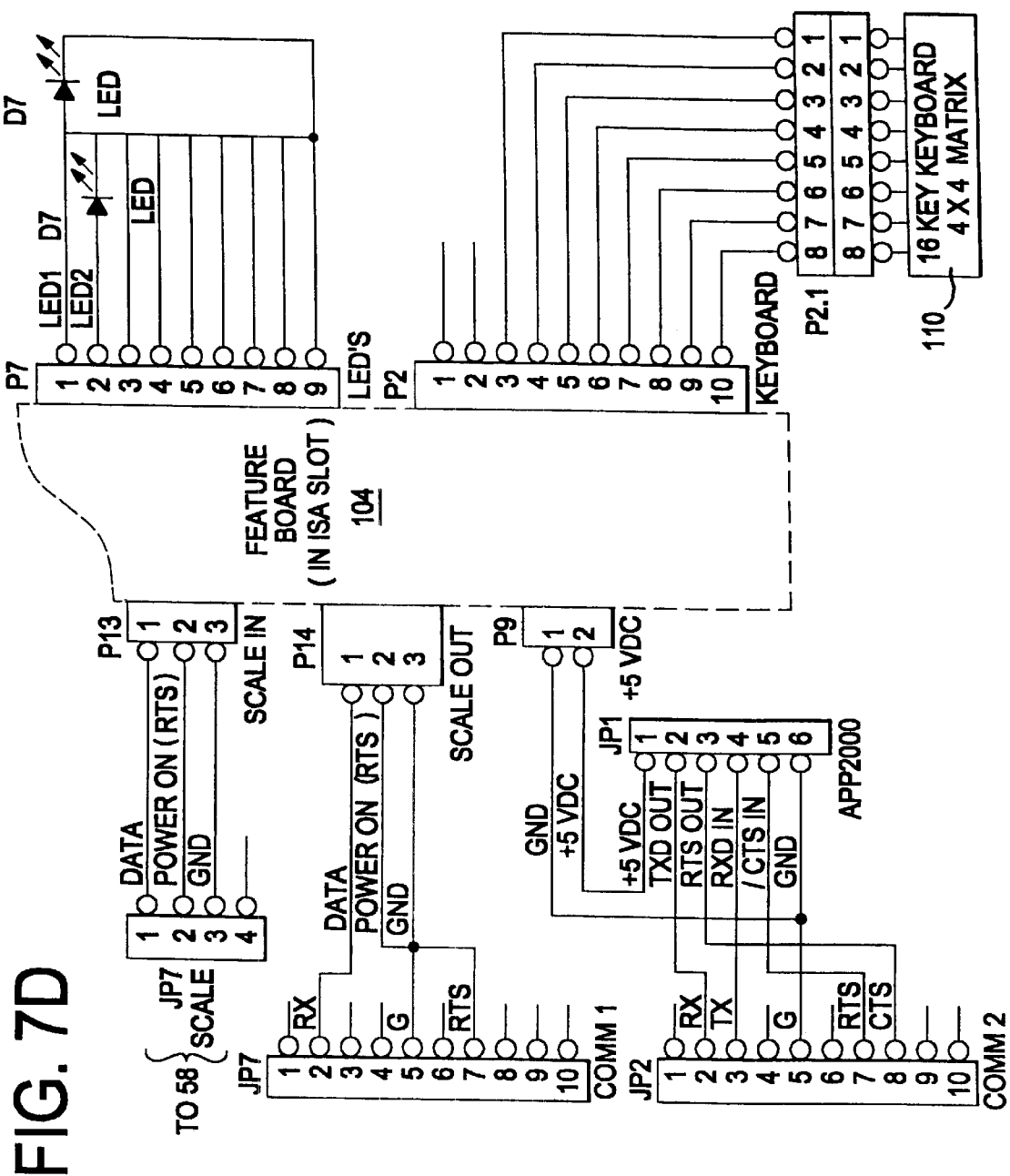
Figure 8A:
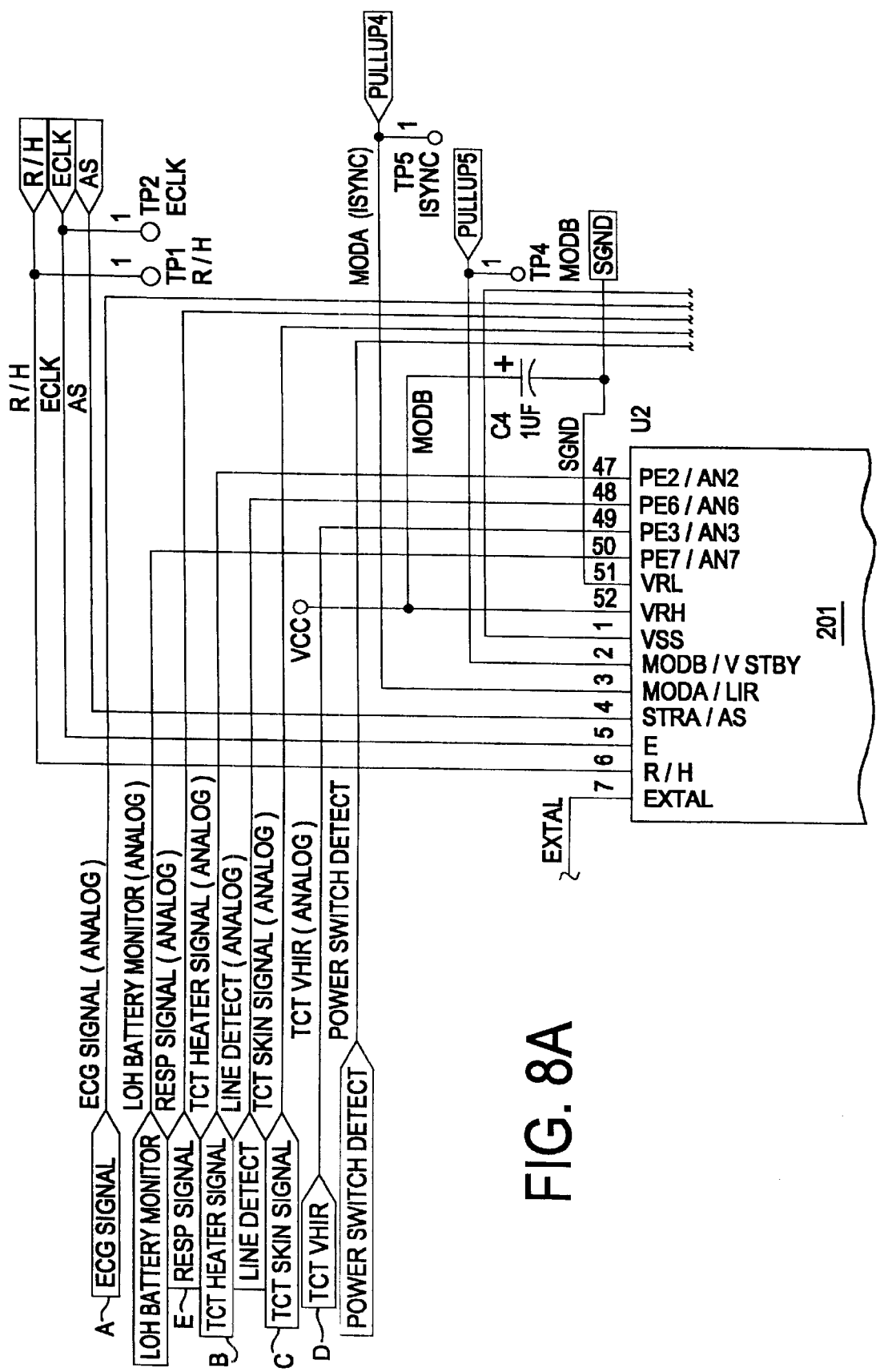
FIGS. 8A–8S are a circuit diagram showing connections among the electronics of the ambulatory patient monitor.
Figure 8B:
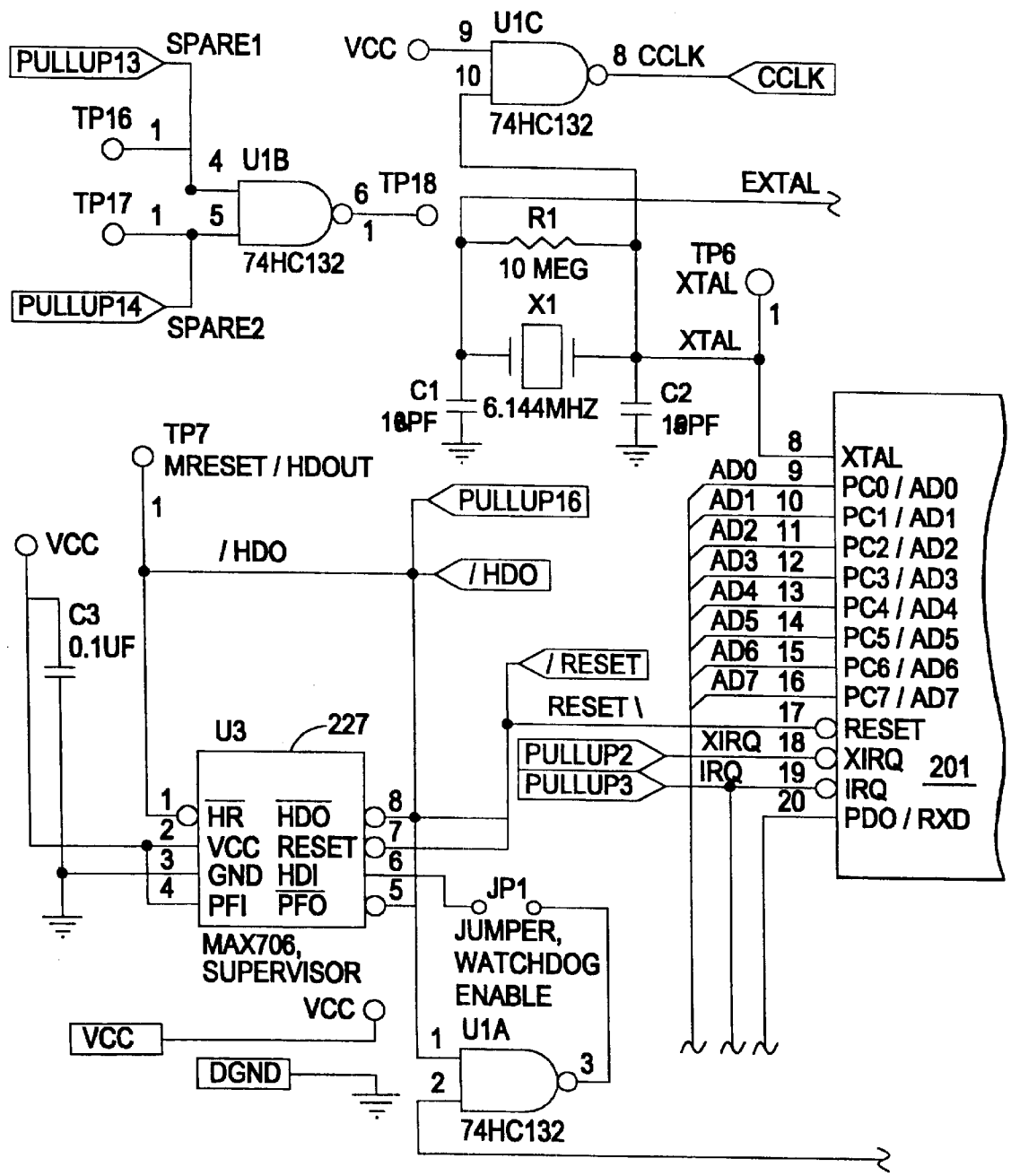
Figure 8C:
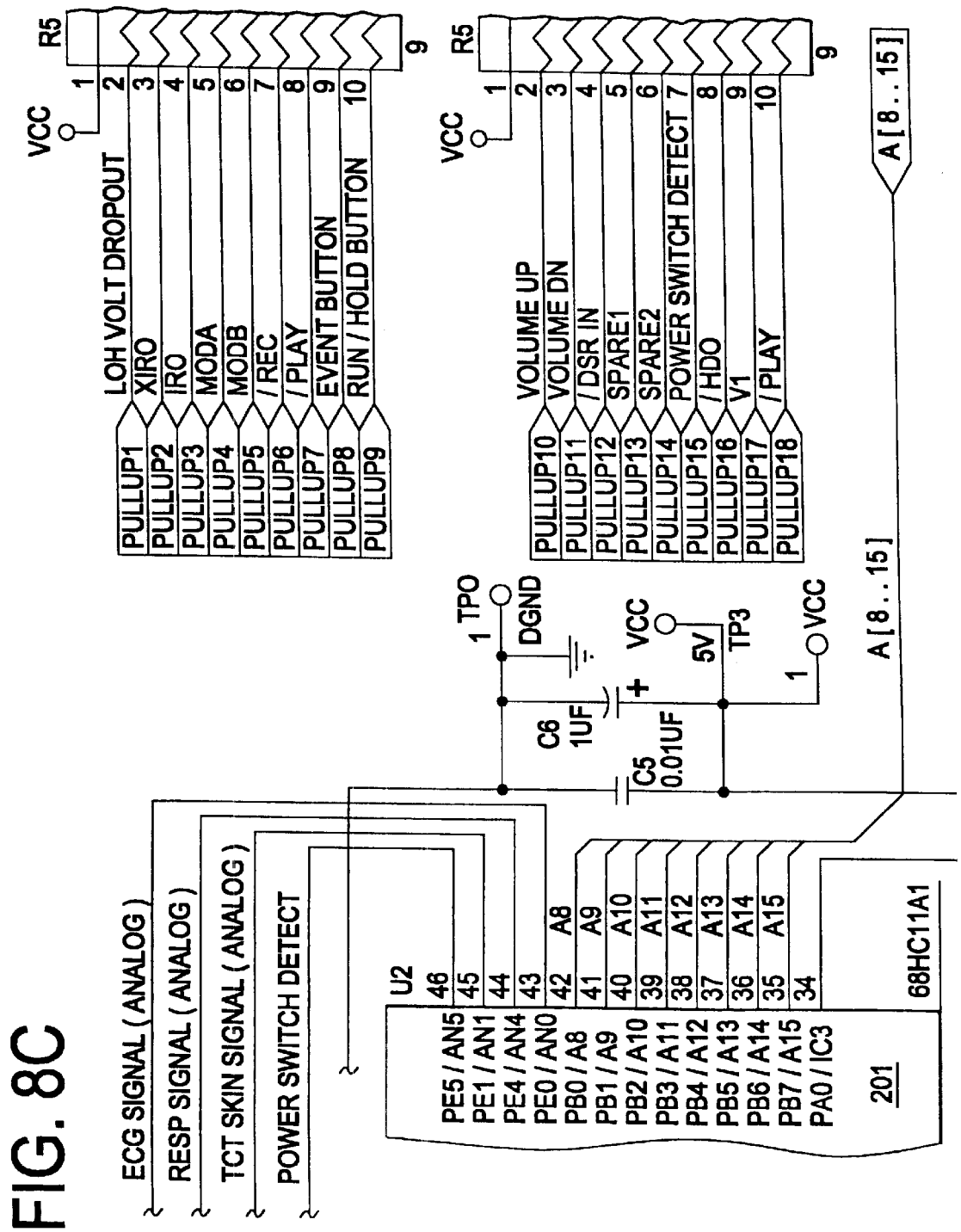
Figure 8D:
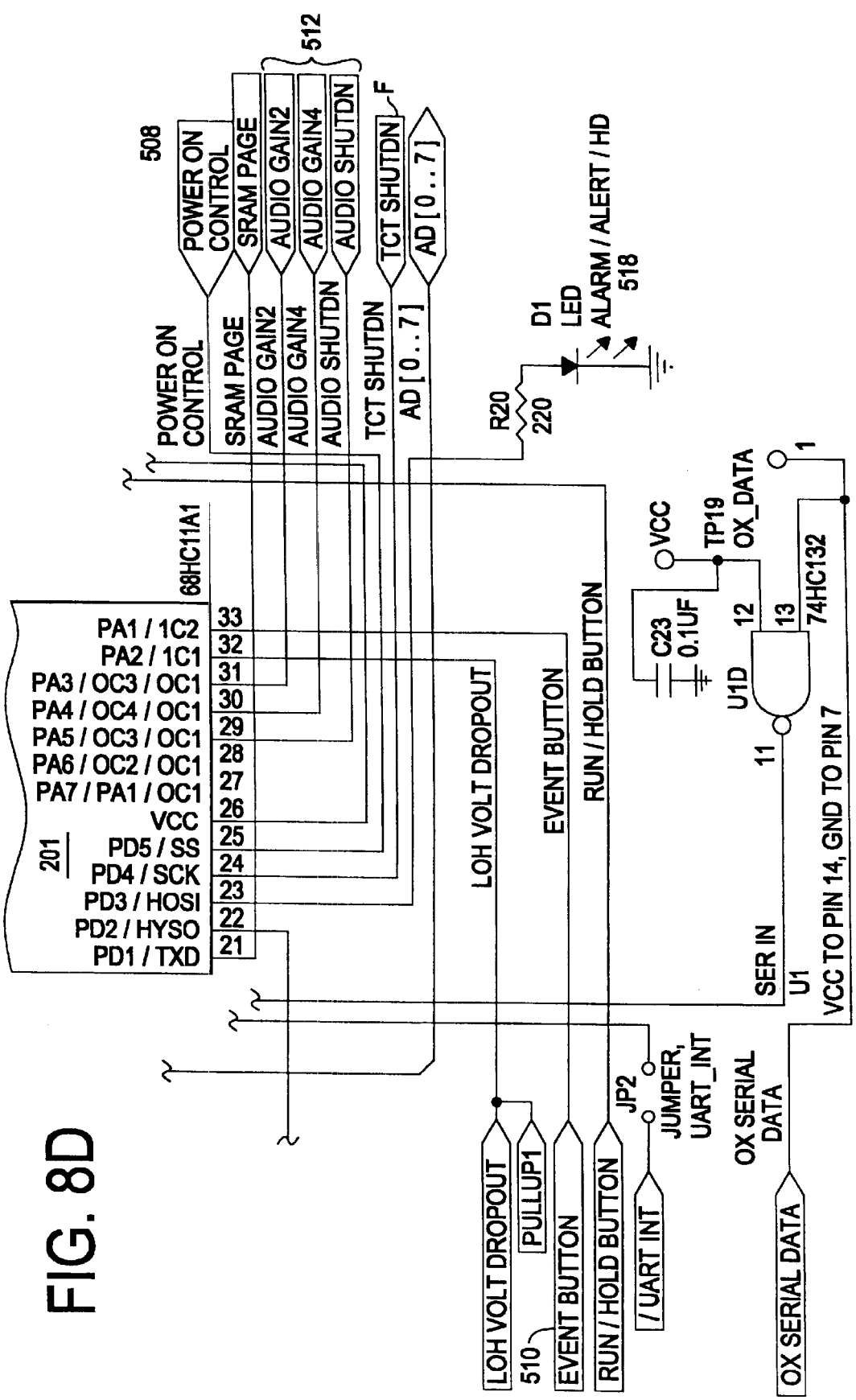
Figure 8E:
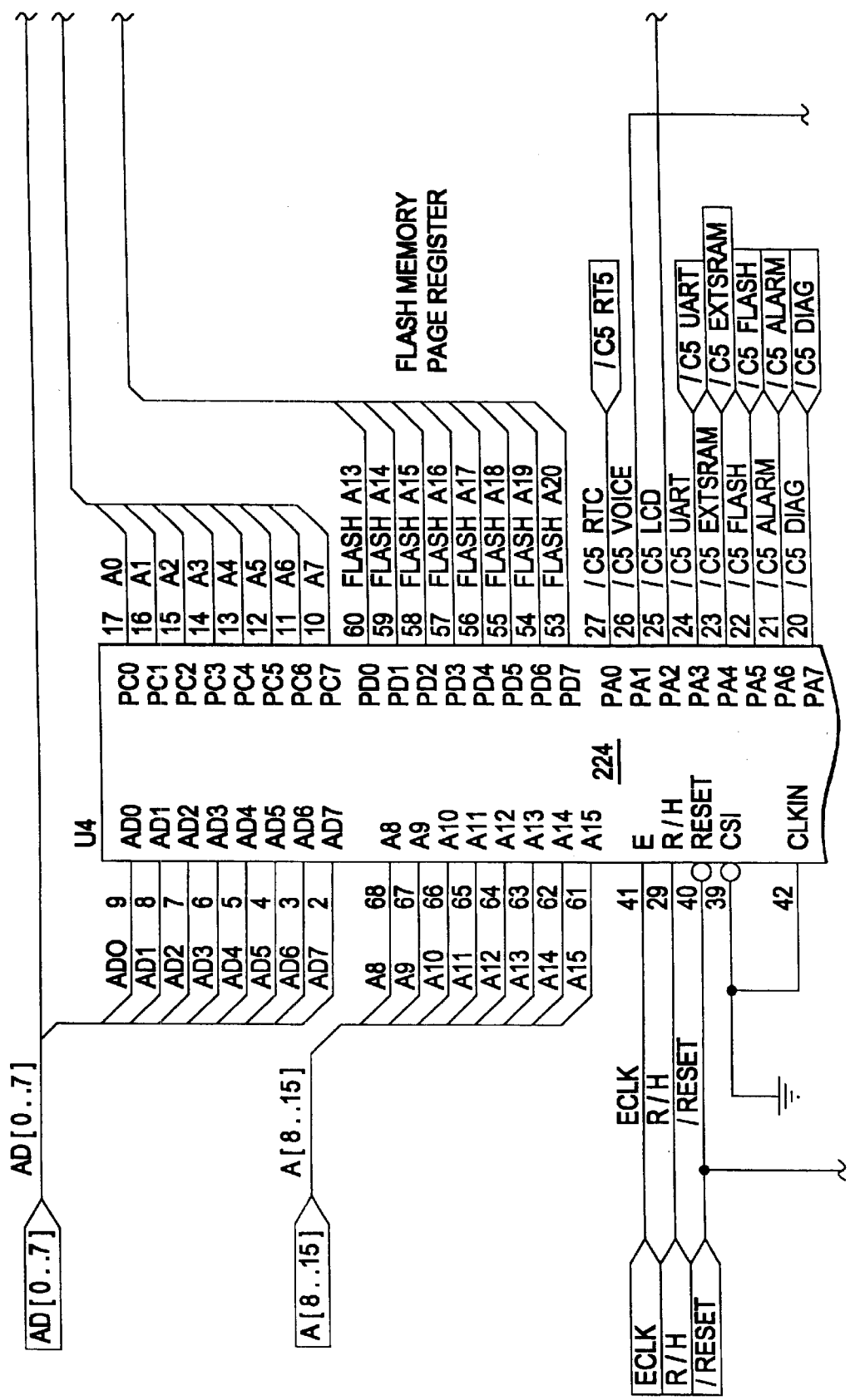
Figure 8G:
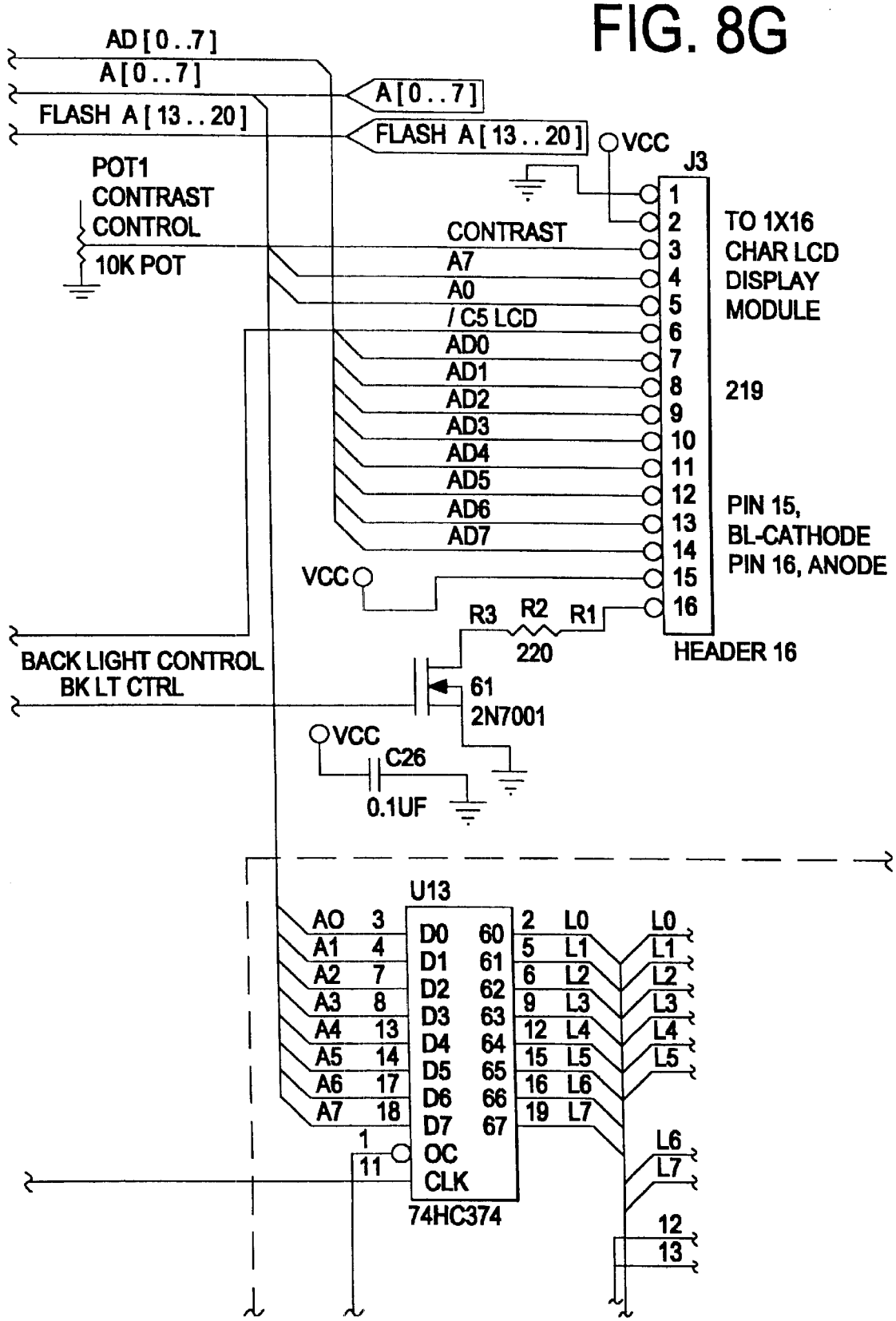
Figure 8H:
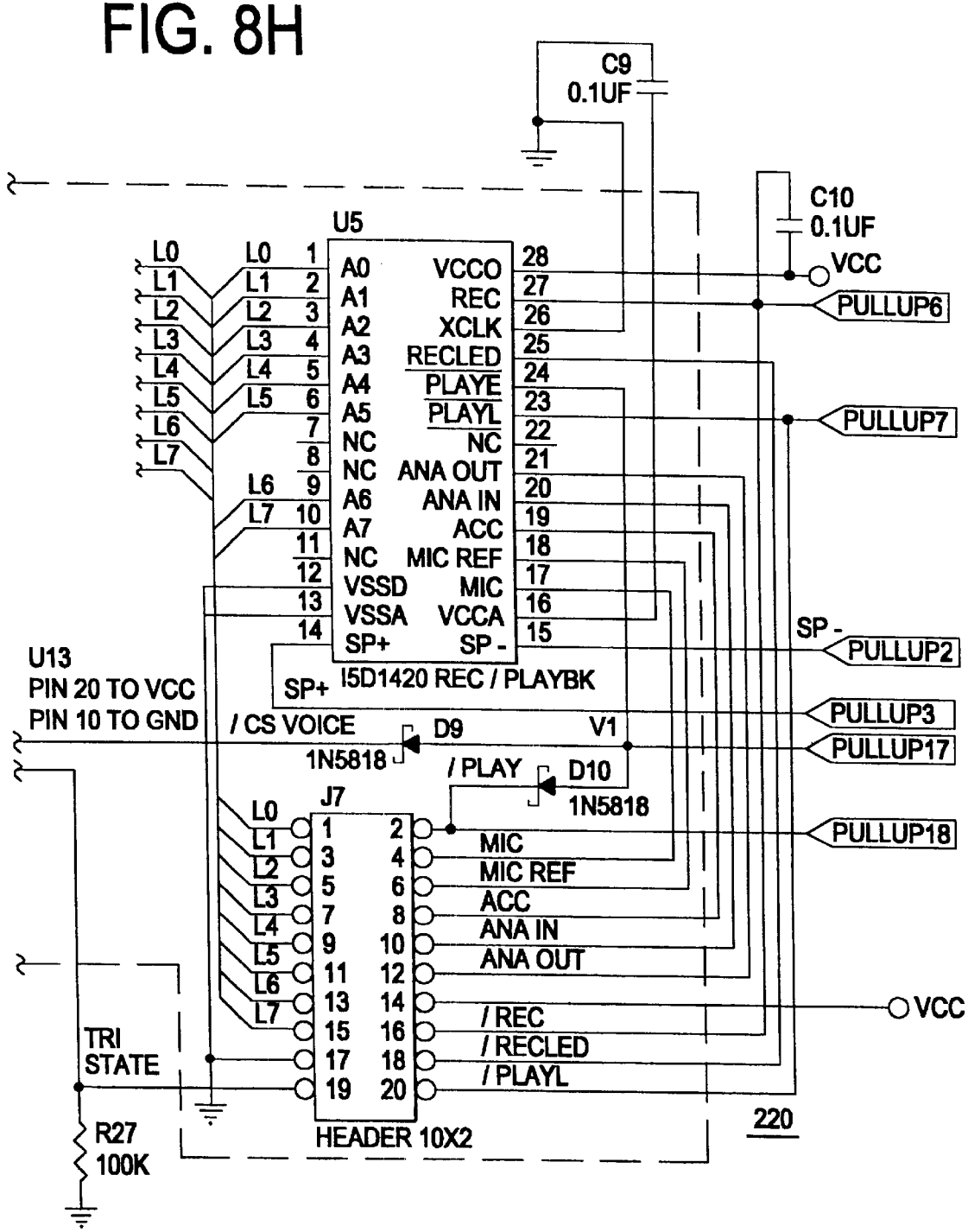
Figure 8I:
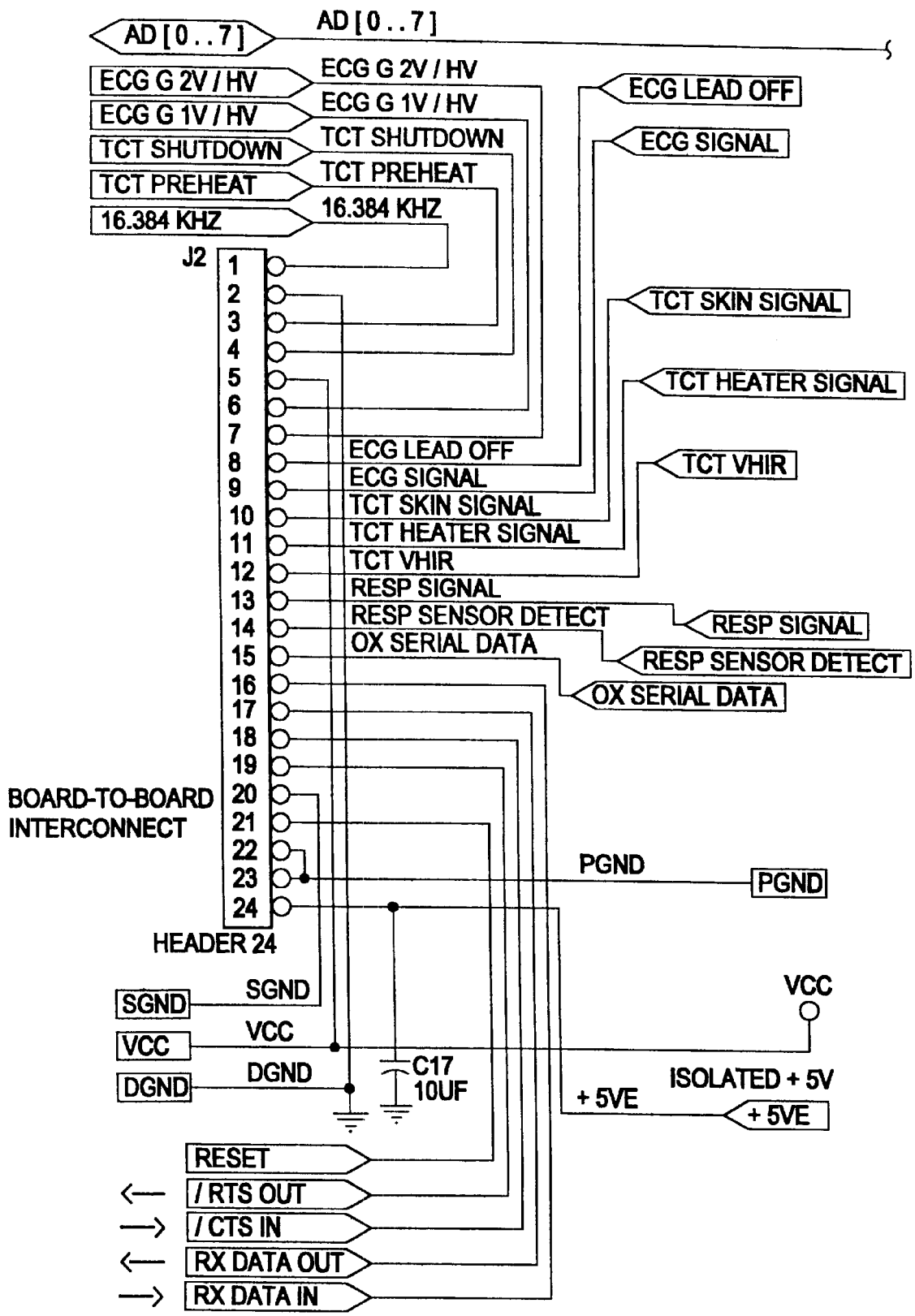
Figure 8J:
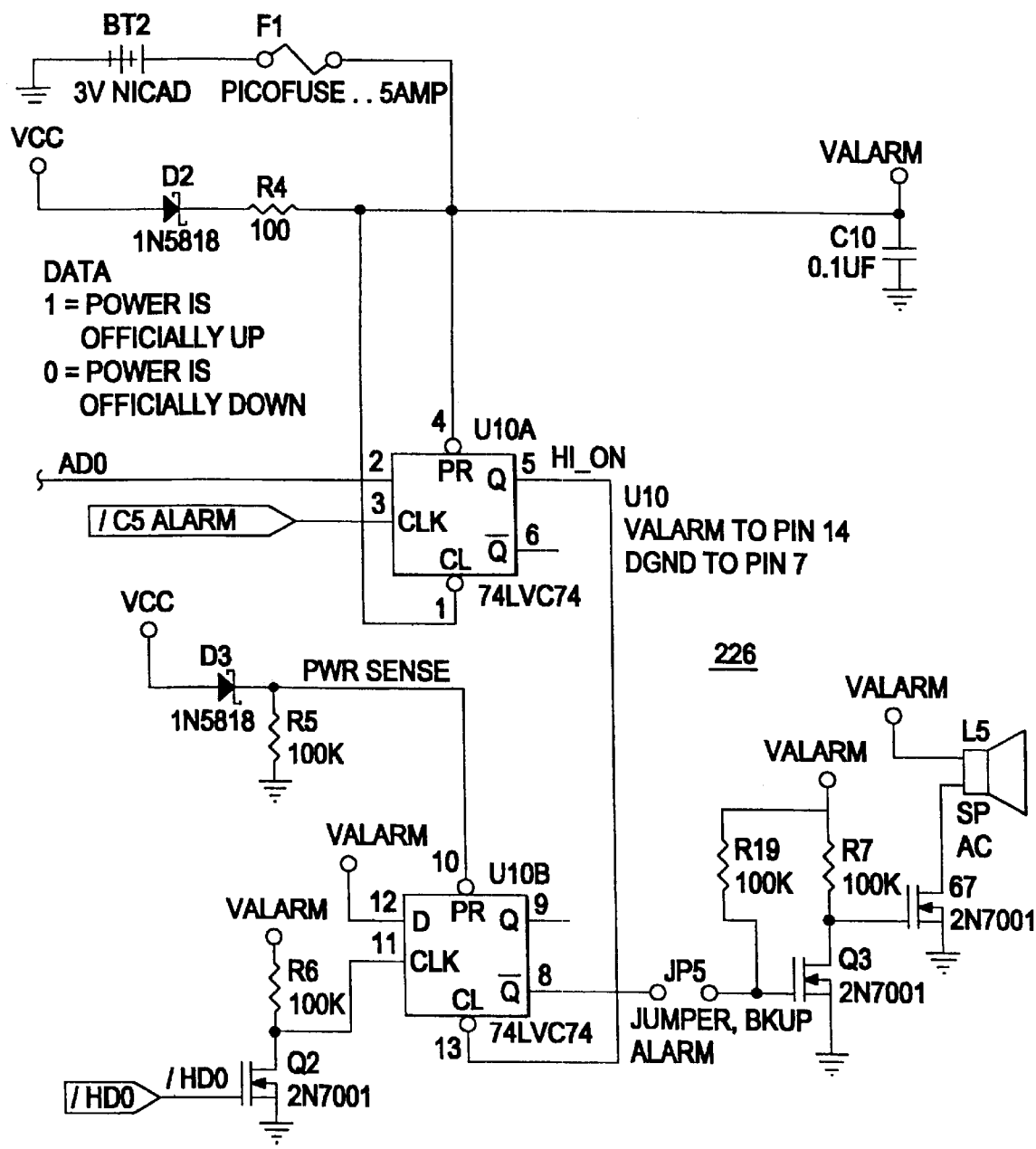
Figure 8K:
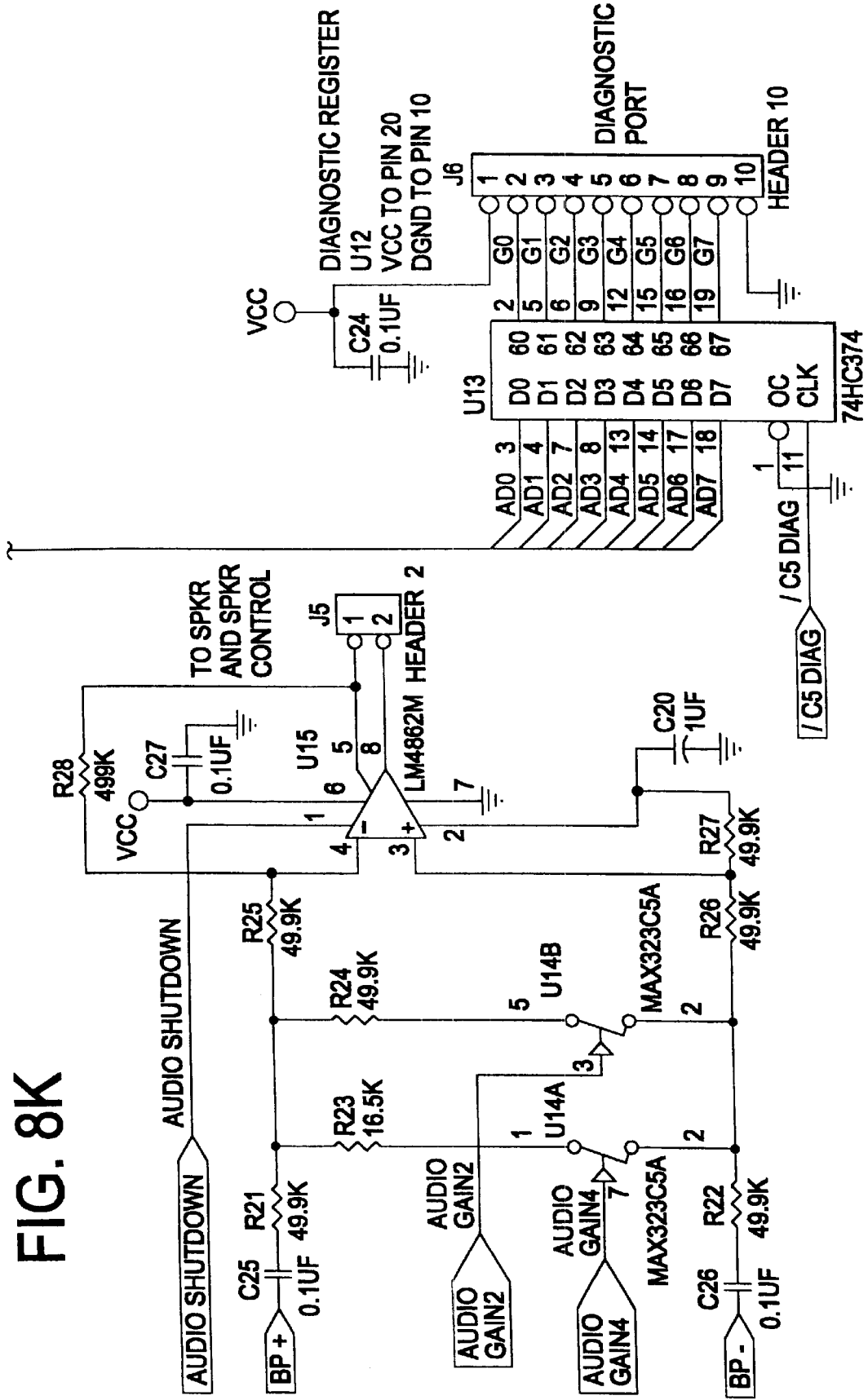
Figure 8L:
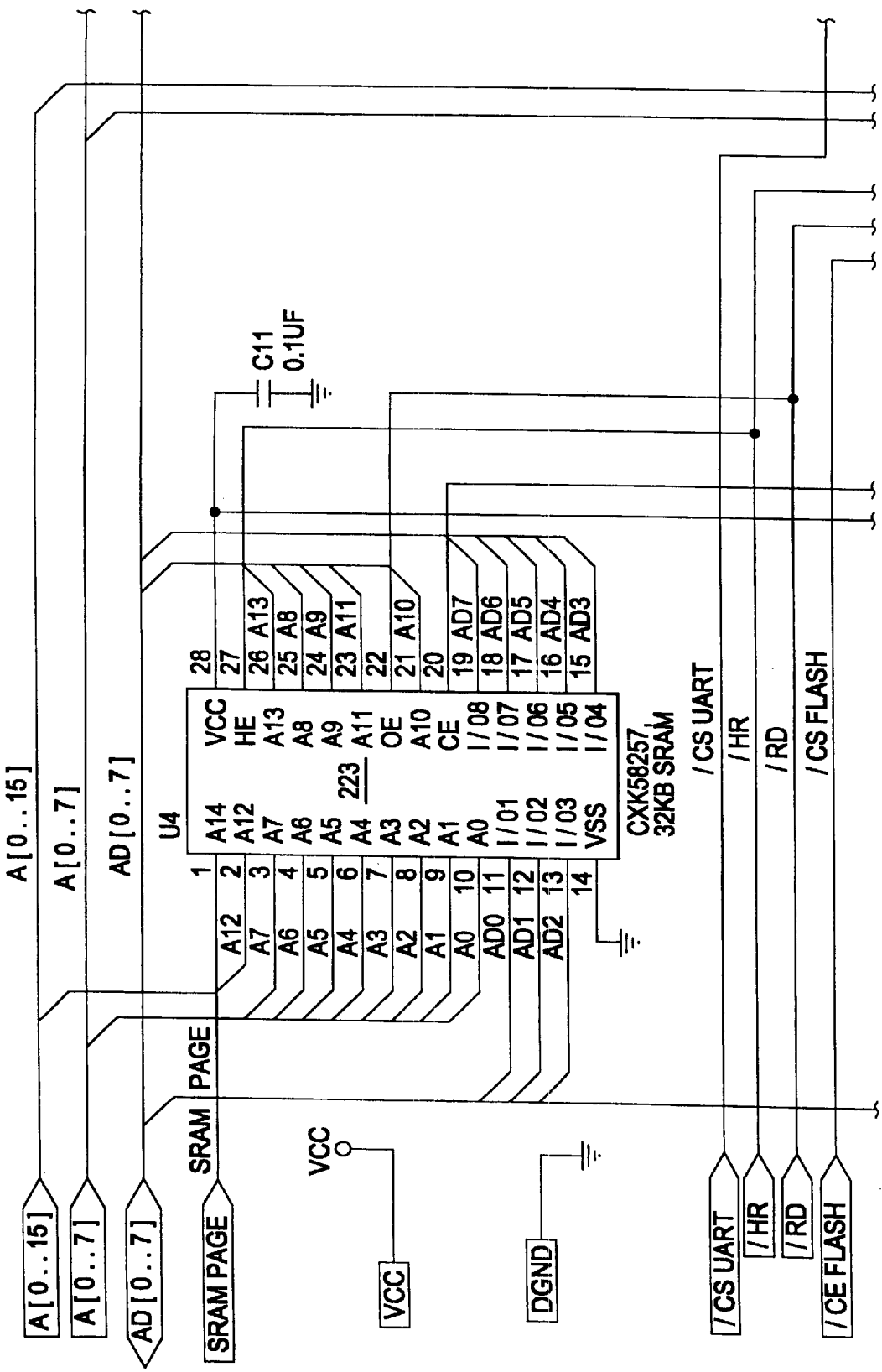
Figure 8M:
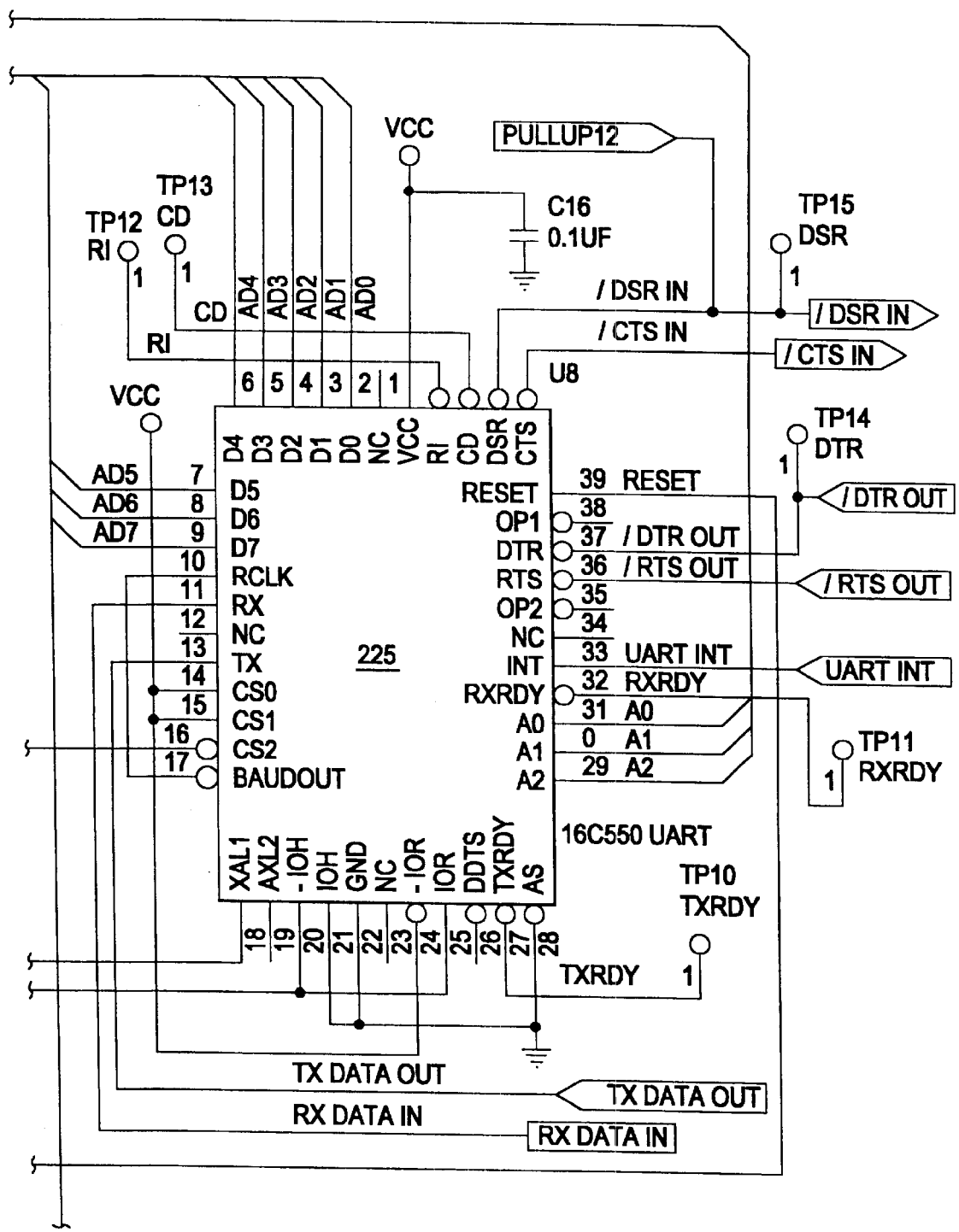
Figure 8N:
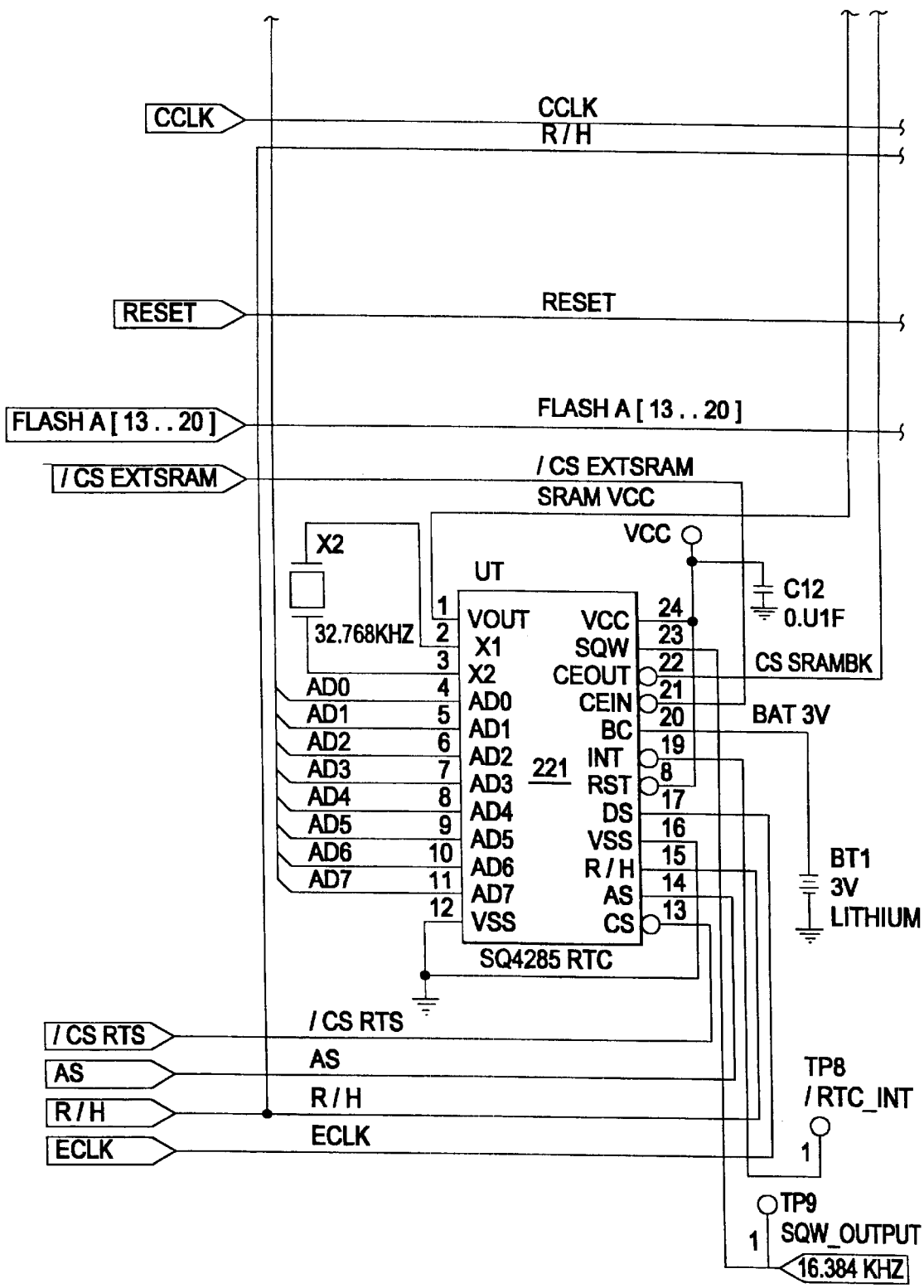
Figure 80:
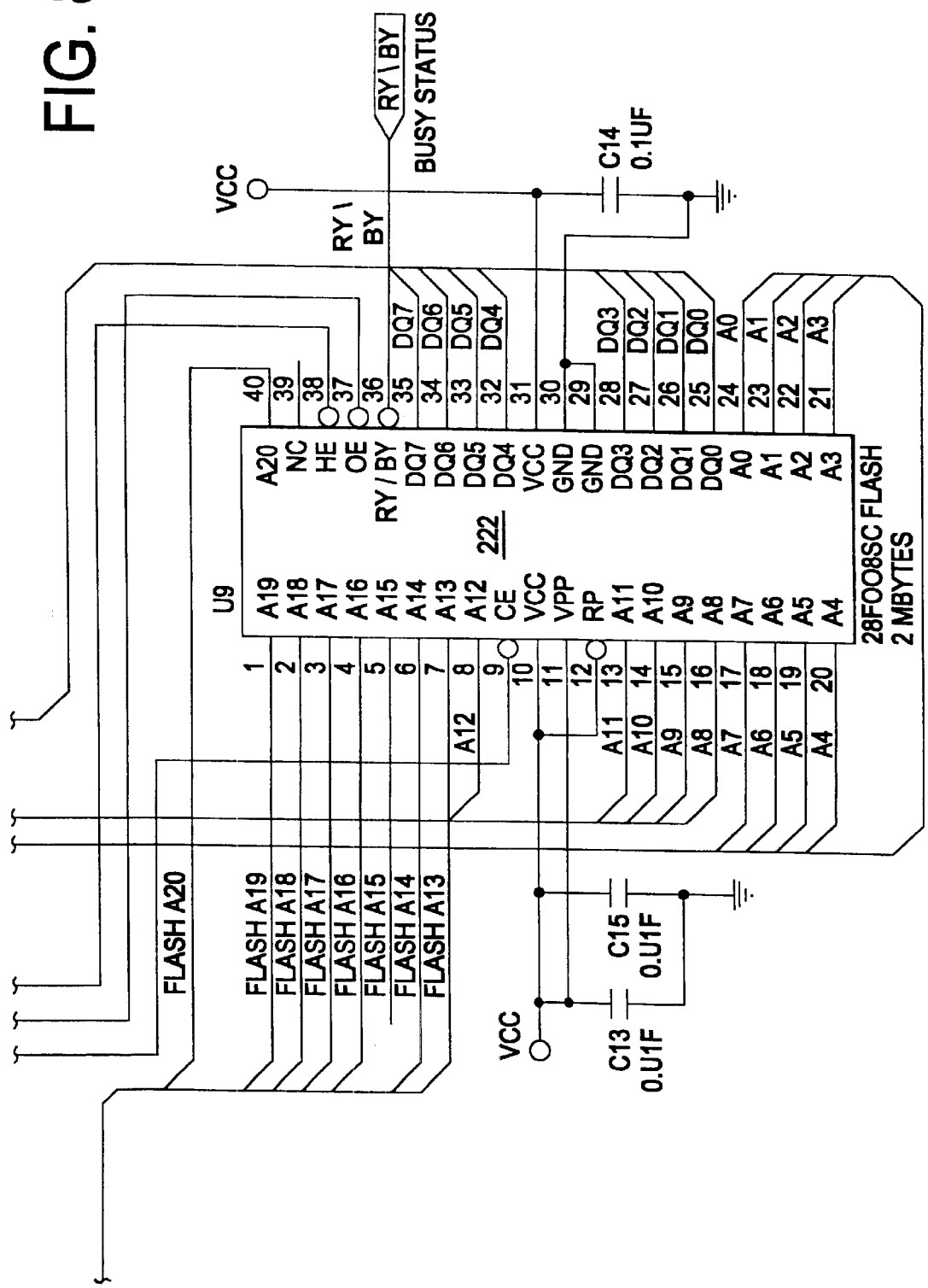
Figure 8P:
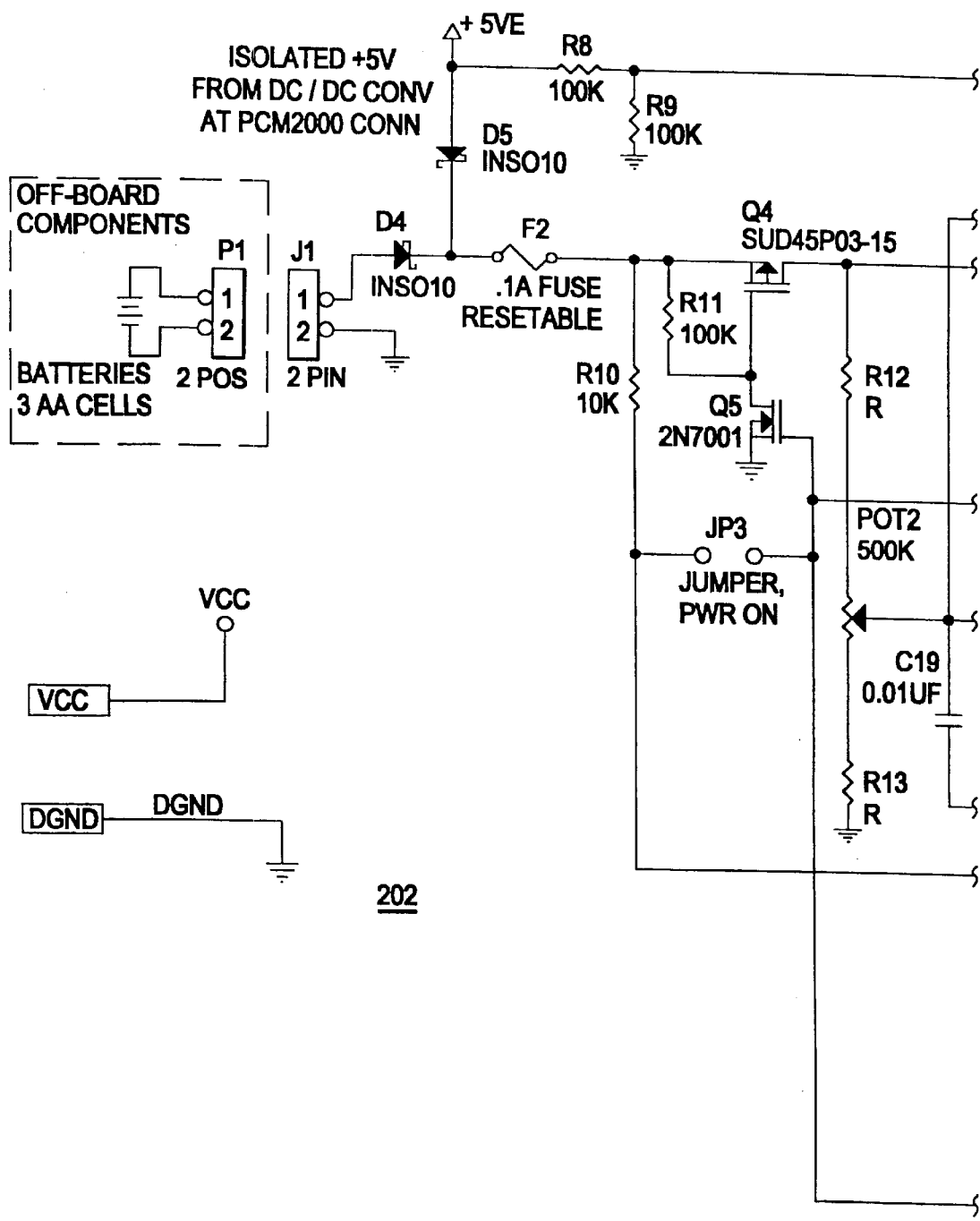
Figure 8Q:
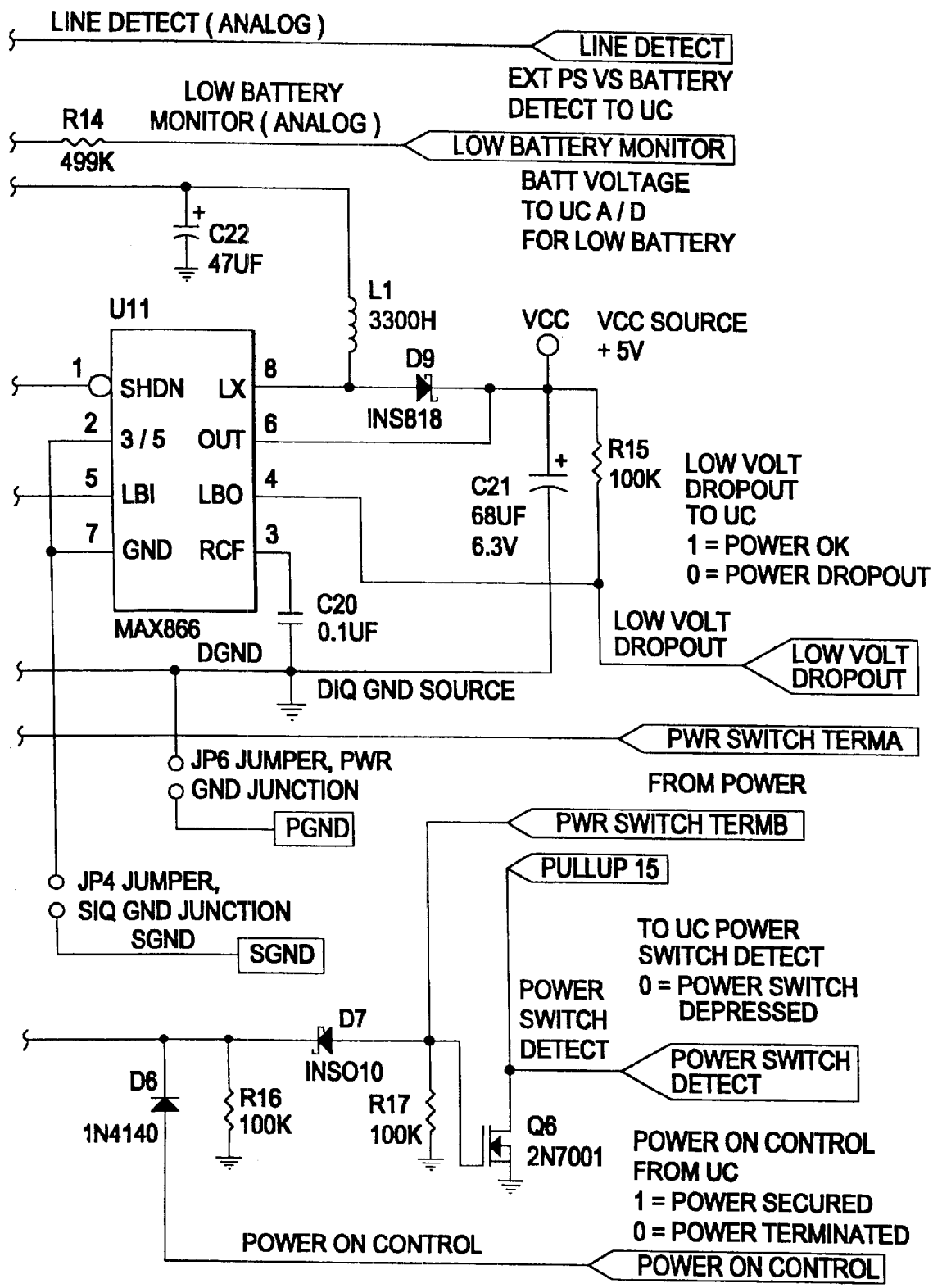
Figure 8R:
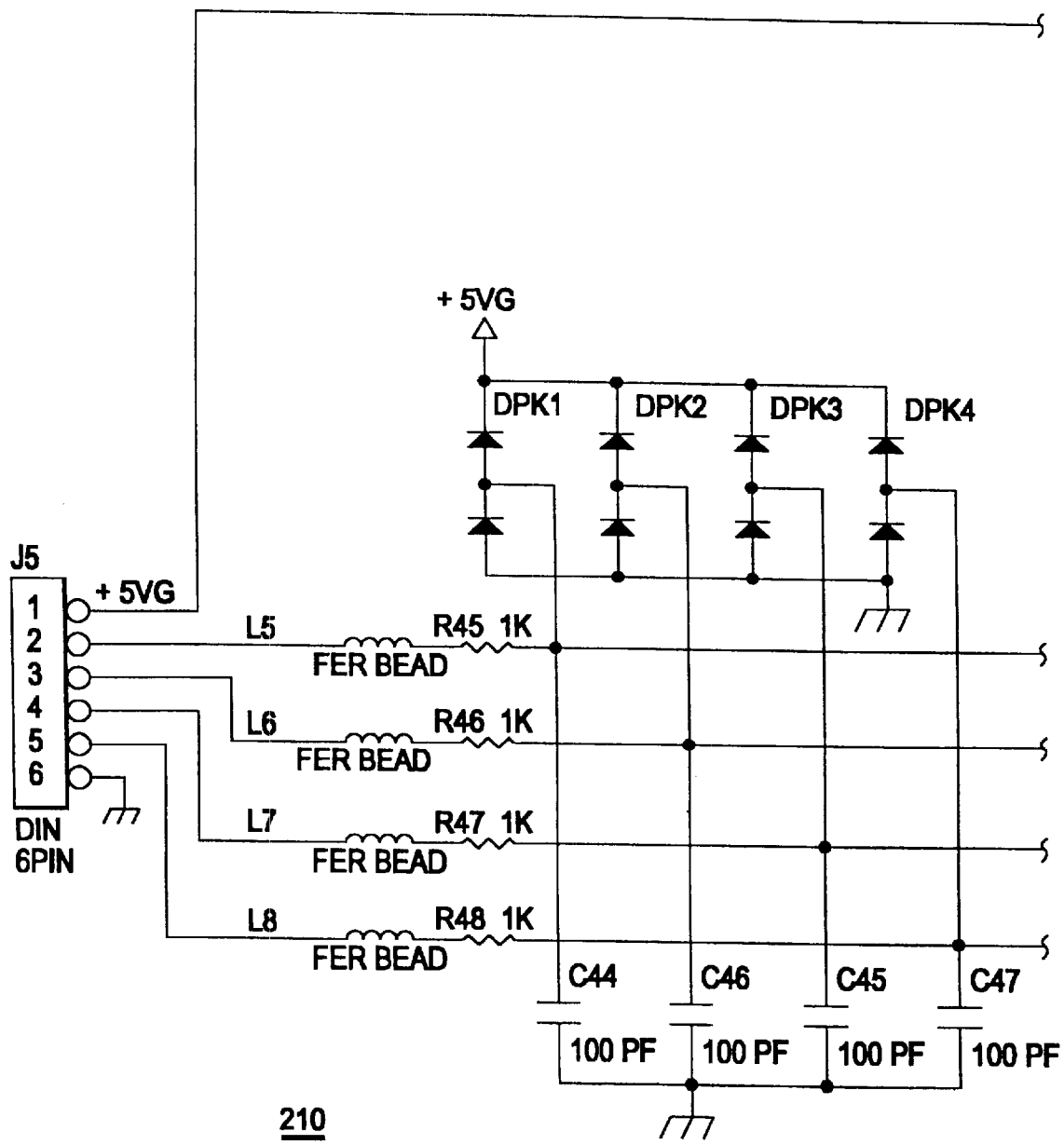
Figure 8S:
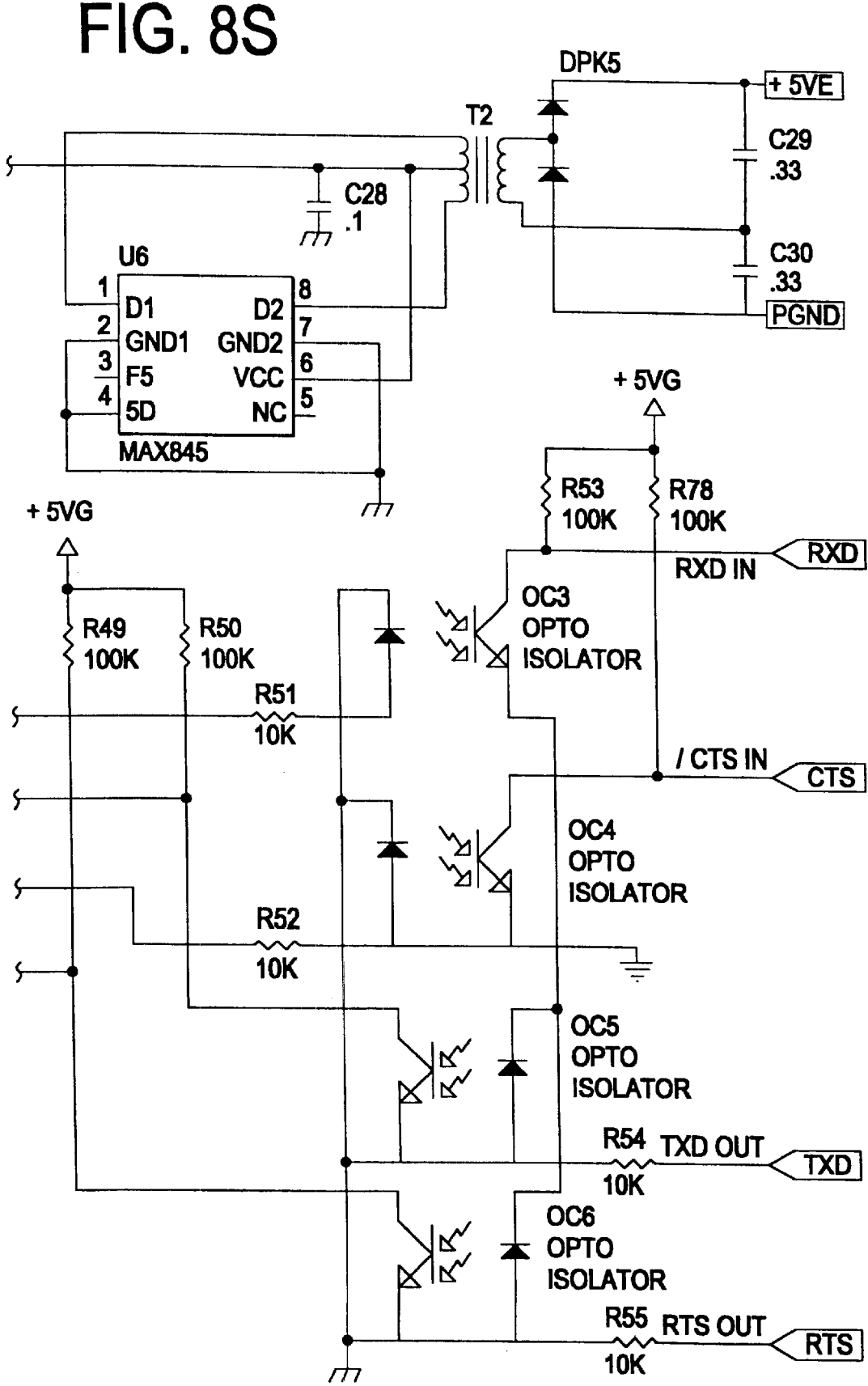
Figure 9A:
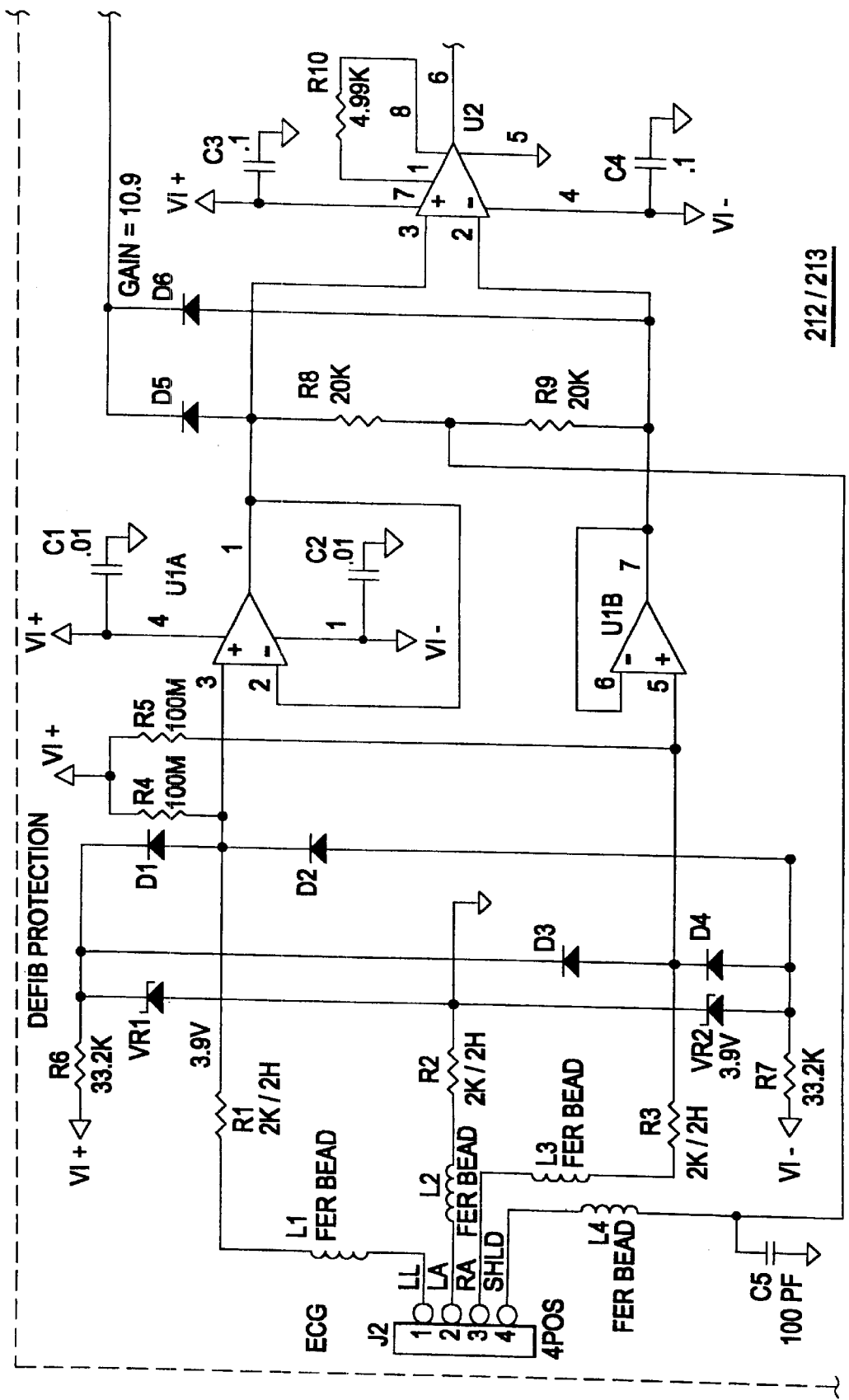
Figure 9C:
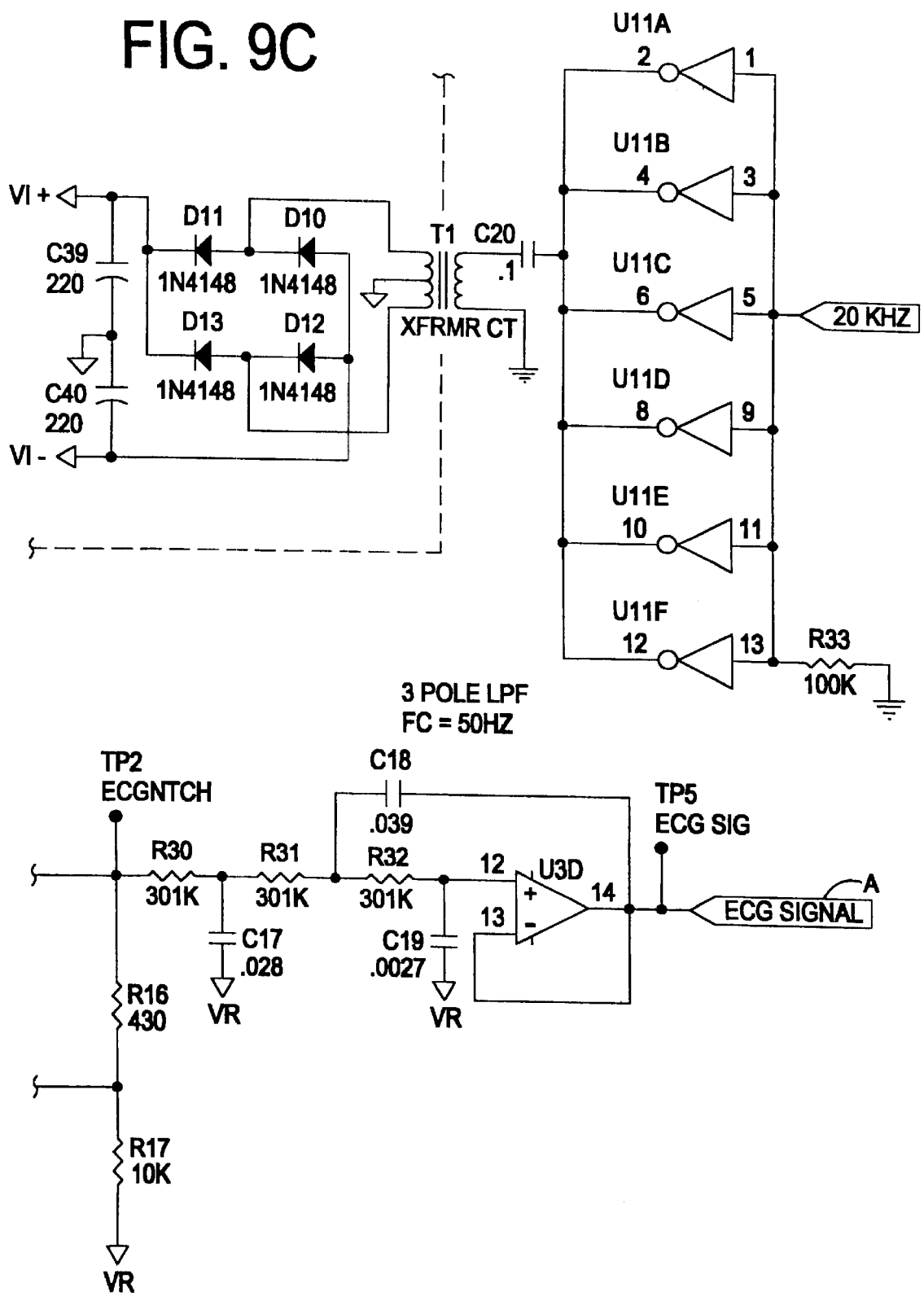
Figure 9D:
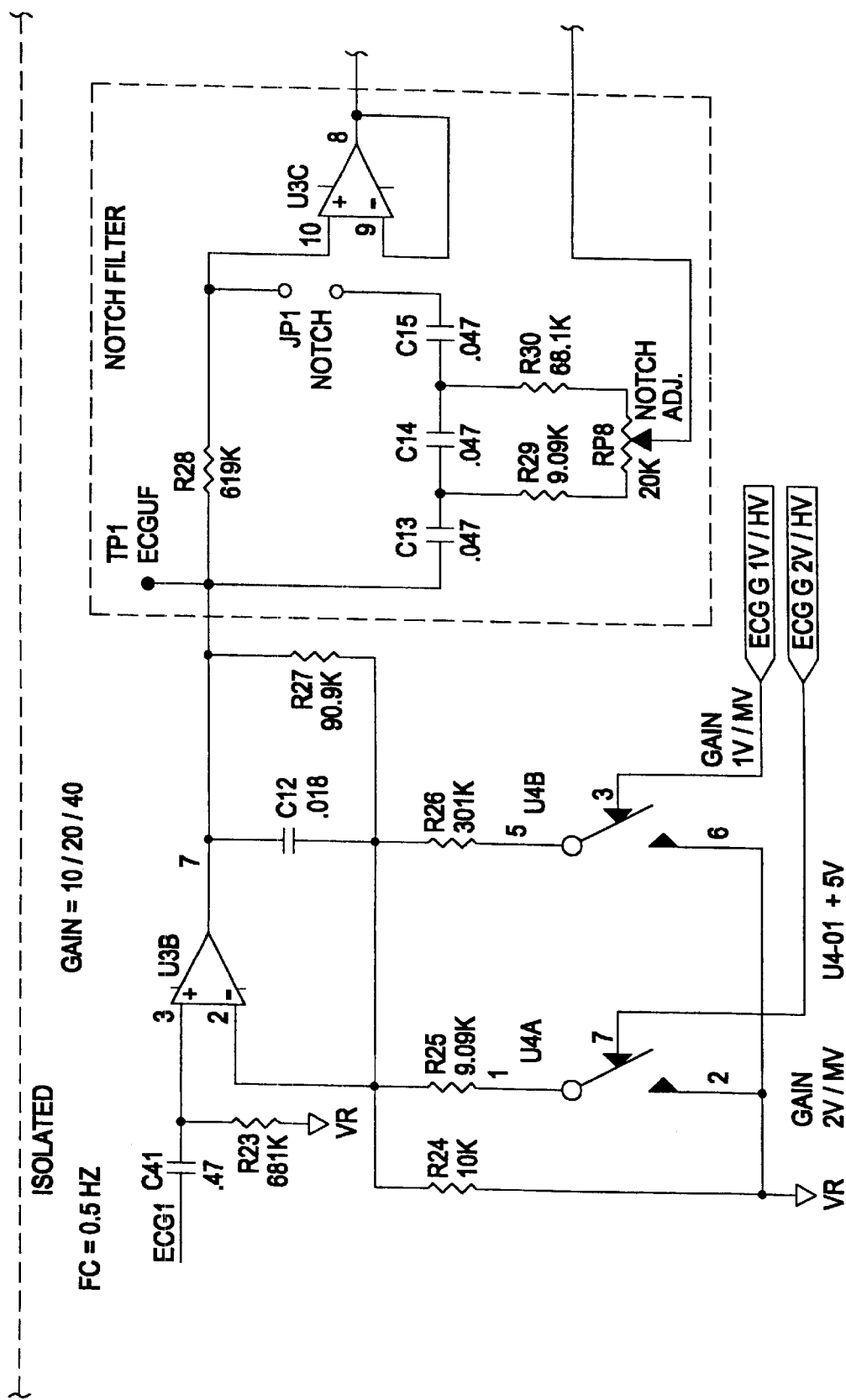

Referring to FIGS. 3A–3B, patient management system 10 includes ambulatory patient monitor 20 coupled to communications unit 30 via media 52. In FIGS. 3A–3B, medium 52 is shown as a detachable cable. Cable 52 may be replaced with a wireless transceiver (RF or IR) in each of monitor 20 and communications unit 30 for providing communication therebetween. Instructions from a caregiver via remote control software 410 are received through modem 31 of communications unit 30 for transfer to monitor 20 when cable 52 is attached. Monitor 20 and communications unit 30 are located at the patient's home or alternate care facility. Communications unit 30 provides a communication link to remote control software 410 over a communication line 452. Communication line 452 can be a telephone line, wireless telephone (such as cell phone), radio link or other form of communication.

Communications Unit

Referring to FIGS. 3A–3B, 5, 6 and 7A–7D, communications unit 30 includes housing 102, custom keypad 110 having a plurality of keys 112, LCD display 114 and speaker 116. Communications unit 30, in this embodiment, also includes a built-in modem 31 for communicating over a telephone line with the remote control software 410 at the caregiver's office. As described above, modem 31 may also be a wireless transceiver (IR or RF). Communications unit 30 includes power supply 32 for receiving standard AC current. Power supply 32 receives power from battery 130 in the event of a line power outage. Otherwise, power supply 32 receives power from line power from AC receptacle 124 through transformer 126. An on/off switch 122 is provided for turning the communications unit 30 on and off.

Communications unit 30 is shown with four interface circuits 33, 34, 35 and 37, located on custom printed circuit board 104, for controlling three separate medical devices and one optional device. Interface circuit 33 is used to couple to blood pressure module 54. Interface circuit 34 is used to couple to temperature sensor 56. Interface circuit 35 is used to couple to weight scale 58. Interface circuit 37 is used to couple to an optional device, shown here as a personal computer 40. Other medical devices may also be coupled to communications unit 30, depending on the caregiver's requirements for the patient. Examples of other sensors that can be used with the communications unit 30 include blood gas analyzers and glucose testers. Data signals generated from each separate medical device are stored in a memory located on mother board 120 of communications unit 30 for later transmission to the caregiver. If a printer or display is coupled to the communications unit 30, the stored data can also be printed or displayed.

Communications unit 30 includes connector 36 for use in coupling to cable 52 for coupling with monitor 20. Connector 36 includes a serial data port for transmitting and receiving data between monitor 20 and communications unit 30 as well as a power connection, which is used to power monitor 20 when monitor 20 is coupled thereto.

The communications unit 30 operates from external line power with an internal battery 130 for short term power storages. Communications unit 30 provides both visual (alphanumeric and graphical displays on display 114 and lamps 118) and aural (tones and voice from speaker 116( for ALARM and ALERT conditions. Communications unit 30 provides interfaces to specific sensors (blood pressure monitor, temperature probe, weight scale, etc.). Communications unit 30 provides for monitoring the individual sensors and other devices attached to it. If a specific sensor is improperly attached or malfunctions, communications unit 30 generates an ALERT signal. In this embodiment modem 31 is a simultaneous voice-over-data modem which allows patient-to-caregiver communication during data transmissions or during setup and troubleshooting. As noted above, modem 31 may be replaced with a wireless transceiver, with or without voice-over-data capability.

Blood pressure module 54 is coupled to communications unit 30 via interface circuit 33 and provides automatic measurement, storage and transmission of the patient's blood pressure data. If interface circuit 33 detects a pressure cuff disconnect or blood pressure measuring device malfunction, communications unit 30 provides a ALERT signal, and automatically notifies the patient (with a visual and/or aural warning).

Weight scale 58 measure the patient's weight with a 0.1 pound resolution. A measured weight signal is applied to interface circuit 35. Communications unit 30 records and stores the patient's weight for subsequent transmission to the caregiver. Malfunction of the weight scale 58 results in an ALERT signal.

Temperature sensor 56 provides for temperature measurement of the patient. A variety of different temperature sensors may be used; oral, rectal, tympanic, etc. This measurement may be used as a backup or check of the values detected by core temperature sensor 216. Communications unit 30 provides an ALARM signal if the detected temperature is outside the values set by the caregiver. These values are set by the instructions downloaded by the communications unit 30 as prescribed by the caregiver and sent via the remote controller. Communications unit 30 detects sensor errors in temperature sensor 56 and provides an ALERT condition. Communications unit 30 transmits temperature data to the caregiver in accordance with a predetermined schedule or if an out-of-limit temperature is sensed.

Preferably the communications unit 30 includes controls that are easy for the patient to understand and use and displays which are easy for the patient to read. An LCD display 114 provides text messages including current time of day, patient instructions and ALERT/ALARM messages. Preferably, the display 114 includes 20 digits per line, 4 lines with backlight. A blinking green LED 118 indicates the communications unit 30 is operating. A blinking red LED 118 indicates there is an ALARM/ALERT pending.

Various user entry keys 112 are provided. A LAMP key turns on the backlight for 2 seconds. VOLUME UP/DOWN keys control the volume of the audio, both speech and tones. A DIAL key causes the communications unit 30 to immediately contact the caregiver (physician/service provider) for assistance. YES and NO keys allow response to questions, such as from the caregiver. A REVIEW key provides a means for a caregiver (or patient) to review the settings of the monitoring routine and identify the causes of the ALARM/ALERT. A Silence key allows the user to silence an ALARM or ALERT audio signal for up to 2 minutes. An internal speaker 116 is used for speech audio and tones related to ALARM and ALERT conditions.

Additional buttons may also be provided. These buttons may be used to facilitate patient queries. For example, when the communications unit 30 is coupled with the remote controller, the remote controller may wish to query the patient for symptoms. Some queries may require only YES and NO responses from the patient. Other queries may require range responses, so a series of numeric labeled keys may be added to communications unit 30. Additionally, the display 114 may also be a dual scan or active matrix display capable of a displaying graphical images to the patient. Graphical images, for example, may be used in showing the patient how to reconnect a sensor.

Operation of the communications unit 30 is easy for both the patient and the caregiver. If the patient's temperature is to be taken, the communications unit 30 alerts the patient with an appropriate text or graphical message, blinking light or audio tone. When a stable temperature is obtained, the communications unit 30 tells the patient that the measurement is complete. When a patient weight is required, the communications unit 30 similarly notifies the patient. When a stable weight is obtained, the communications unit 30 tells the patient to step off the scale.

The communications unit 30 is intended to be operational at all times the patient is being monitored, in order to receive incoming messages from the caregiver and in order to send messages or data to the caregiver. The DIAL key may be also used to automatically dial the remote controller for instructions or to request help or clarification. Additional DIAL keys may also be included. These additional DIAL keys may be programmed to automatically dial a local pharmacy, a paramedic, or a family member, for example. The communications unit 30 checks continuously for sensor, lead wire, and external equipment failures (for those items connected to the communications unit 30). When a failure is detected, the communications suit 30 sounds an ALERT and displays instructions on how to clear the ALERT. ALERTS should be responded to quickly to avoid triggering an ALARM. An ALARM is triggered whenever a monitored physiological variable is measured which is outside of its prescribed limits. A battery low-ALERT indicates when the backup battery is low and should be recharged from a power supply driven by line current. Further details of preferred operation of ALARM and ALERT signals, as well as the warnings displayed are described below.

Programmable, Ambulatory Patient Monitor

Referring to FIGS. 3A–3B and 8A–8S, ambulatory patient monitor 20 includes microcontroller 201 which controls operation of the various functions of ambulatory patient monitor 20. Microcontroller 201, which may be a 68HC11A1, provides signals to control operation of the front panel lights and switches/keys 218 (see FIG. 4). These signals are provided via connector J4. For example, input from Event key 510 is applied to pin 33 of microcontroller 201. Input from power On/Off switch 508 is applied to pin 25 of microcontroller 201. To activate red LED 518, microcontroller 201 provides an enable signal from pin 23. In addition to double insulation on all cables and wires between sensors and the patient and between the sensors and the monitor 20, isolation circuit 210 provides part of the patient protection from ground faults and other electrical shocks.

Isolation circuit 210 provides electrical isolation for the monitor 20 internal circuitry from earth ground which enters the monitor 20 through data port connector J5. The isolation is part of one layer of the double insulated design for the monitor 20. The electrical isolation serve to protect the patient from potentially harmful electrical leakage current. The electrical isolation barrier consists of optical couplers OC3–OC6 and isolation transformer T2. The optical couplers transmit the serial data port signals, RXD, /CTS, TXD and RTS across the isolation barrier via light emitted from a light emitting diode (LED) to a phototransistor, both of which are internal to the optical couplers. The MAC845 is a transformer driver which converts the +5 VDC from the data port to a high frequency (450 to 700 kHz) square wave suitable for driving the transformer. The diode pack DPK5 and capacitors C29 and C30 rectify and filter the signal from the transformer to convert it back to a DC voltage. This external source is used to power the monitor 20 in order to conserve battery power.

The ferrite beads L5–L8, resistors R45–R48, capacitors C44–C47 and diode packs DPK1–DPK4 are used to protect the data port from electromagnetic interference and electrostatic discharge (ESD). The ferrite beads, resistors and capacitors from a filter to attenuate high frequency interference signals. The diode packs and resistors form a clamping circuit to prevent high voltage ESD spikes from damaging the circuitry.

Data messages stored in EEPROM/RAM 224 are retrieved by microcontroller 201 via pins AD0–AD7 and provided to connector J3, which is coupled to display 219, where they are displayed to the user. Voice and tone sounds stored in EEROM/RAM 224 are retrieved via pins A0–A7 and provided to voice and sound operator 220, which are used to drive a speaker. Voice and sound generator 220 includes a playback chip which is preferably a ISD1420 and may also be connected to a speech synthesizer.

Microcontroller 201 stores data and accesses Instructions from three separate memories. Data recorded from each attached sensor is stored or recorded to Temporary Recording Memory 223 and a Main Recording Memory or Flash Memory 222 via lines A13–A20. Instructions pertaining to operation of the monitor 20, ranges of acceptable values (Instruction Table entries), and messages are stored in EEPROM/RAM 224.

The recording memory operation, i.e., the recording of detected physiological data from the sensor modules, involves two recording memories a Temporary Recording Memory 223 and a Main Recording Memory or Flash Memory 222. A 256-byte record is written to both the Temporary Recording Memory 223 and the Main Recording Memory 222. A 256-byte record is written to the Temporary Recording Memory 223 every second while the monitor 20 is in Run Mode, Alarm Mode, or Event Mode of operation (modes of operation are described below). A record consists of the most recent data available from the oximetry 214, temperature 216, and respiratory rate 215 measure systems, and one second of data from the ECG 217 system. The Temporary Recording Memory 223 preferably has a capacity for at least 60 second of records, or 16 Kbytes. The main recording (FLASH) memory 222 preferably is a large memory (at least 1 mbyte) which will contain multiple records as defined above), Flash Memory 222 is used to store data for later transmission to the communications unit 30. Software routines for operating the ambulatory patient monitor 20, the Instruction Table (the range of acceptable values for each sensor for a particular patient described below) and other Instructions received from the caregiver are stored in EEPROM/RAM memory 224.

UART 225 is used to transmit and receive data via isolated serial ports 205, 206. The RS232 driver 205 receives and transmits data from connector 204 which is coupled to communications unit 30 during data transmissions. Processor supervisor 227 controls the hierarchy of interrupts during communication. When connected to communications unit 30, power from communications unit 30 is converted by DC-DC converter 203 and then provided to power supply 202.

Power supply 203 is an isolated DC-DC converter which gets 5 VDC input from the communications unit 30 and outputs an unregulated 5 VDC to power supply 202. Power supply 203 consists of transformer driver integrated circuit MAX845, isolation transformer T2, rectifier diode DPK5 and filter capacitors C29 and C30. This circuit is unique in that it is normally used to provide isolated power to a serial port from the internal circuitry off an electronic device. In this case, power is drawn from the serial port connection to power the isolated internal circuitry of the monitor 20.

Power supply 202 consists of a step-up DC-DC converter and associated circuitry to turn power on and off to the monitor 20. The power input to the DC-DC converter comes from either a battery pack or the unregulated 5 VDC from power supply 203, whichever has the higher voltage.

The ambulatory patient monitor 20 is configured to accept a plurality of sensors. Preferably, the ambulatory patient monitor 20 is configured to monitor electrocardiogram, respiration rate, pulse oximetry and temperature. The ambulatory patient monitor 20 may be configured to accept other sensors, depending on the patient's monitoring, diagnosing or therapy requirements. Monitor 20 includes four interface circuits for interfacing with up to four physiological sensor modules Interface circuits 212, 213 interface with ECG electrode module 217. Interface circuit 209 interfaces with core temperature module 216. Interface circuit 209 interfaces with respiration sensor 208. Oximetry module 207 interfaces with oximetry sensors 214. Outputs from the interface circuits are applied via connector J2 to inputs of microcontroller 201.

Referring to FIG. 4, the ambulatory patient monitor 20 is small, compact, lightweight and can be worn in sensor pouch 310 so the patient can maintain a level of normal activity while being continuously monitored. The ambulatory patient monitor 20 includes both visual, displays and lamps, and aural, tones and voice, warnings for ALARM and ALERT conditions. An ALERT requiring patient attention, such as missing electrode. ALERTS can be cleared by the patient. An ALARM is a condition is a condition requiring immediate contact with the caregiver. Only the caregiver can clear the ALARM.

The ambulatory patient monitor 20 includes LCD display 219, which displays time of day and ALERT/ALARM messages. Display 219 is preferably large enough to display 32 characters in 2 lines, with backlight. Blinking green LED 502 indicates ambulatory patient monitor 20 is operating; blinking red LED 518 indicates an ALARM or ALERT is pending. LAMP key 516 turns on the backlight on the display 614 for 2 seconds. Volume UP/DOWN keys 512 control the volume of audio (speech and tones). EVENT key 510 causes 1 minute of pre-event data and 1–5 minutes of post-event data to be stored in memory 222. YES and NO keys 520 allow response to questions from communications unit 30. ON/OFF key 508 turns ambulatory patient monitor 20 on and must be pressed simultaneously with the YES key 520 to turn the ambulatory patient monitor 20 off. REVIEW key 506 provides a means to review INSTRUCTION settings and to identify causes of ALARMS/ALERTS. SILENCE key 504 allows the user to silence an ALARM or ALERT for up to 2 minutes. An internal speaker (not shown) is used for speech audio and tones related to ALARM and ALERT conditions. A battery door (not shown) is provided for removal and replacement of 3 AA alkaline batteries.

In an alternative embodiment, wireless communication can be used instead of coupling the ambulatory patient monitor 20 to the communications unit 30 via cable 52. In this embodiment, the ambulatory patient monitor 20 and the communications unit each include a wireless transceiver. Thus any communications unit 30 which could be accomplished through cable 52 can also be communicated via the wireless transceivers.

Use of wireless transceivers for communication provides an additional advantage; in the event of an emergency or "panic" situation, to the patient need not connect the cable 52 between the monitor 20 and communications unit 30. Referring to FIG. 4, ambulatory patient monitor 20 includes two panic buttons 511. These panic buttons 511 may be labeled "Panic" and provide a panic function for the patient. When the patient presses the panic button 511, the ambulatory patient monitor 20 changes its internal status to indicate a message is pending and transmits a signal to communications unit 30. The communications unit 30 polls the monitor 20 approximately once per second. Upon receipt of the message, the communications unit 30 determines the monitor 20 is sending an Emergency message. This signal causes communications unit 30 to respond in accordance with whatever emergency procedure has been programmed. For example, the communications unit 30 may be programmed to contact the caregiver at the remote location. Alternatively, the communications unit may be programmed to dial "911." After the communications unit 30 dials "911," it sends an acknowledgement message to the monitor 20. The monitor 20 displays a message, such as "Call to 911 Sent" to advise the patient that help is on the way.

If the communications unit 30 is programmed to contact the caregiver, and communications unit 30 is already in communication with the remote control software 410, the panic signal can be acted upon at the remote location. If communications unit 30 is not in communication with remote control software 410, communications unit 30 will establish communication by dialing the remote location.

The caregiver can respond to the emergency in a number of ways. For example, if modem 31 is a voice-over-data modes, the caregiver can try to establish voice communication with the patient. If the patient is close enough to the communications unit 30, the patient can respond to the caregiver's questions. The caregiver can download the patient physiological condition data to use in evaluating what course of action to take in response to the panic signal. The caregiver can also contact a designated family member to visit the patient or alert the police, ambulance or other medical assistance services.

A single panic button 511 may be provided, in which case the patient must press the panic button twice to enable the emergency function and avoid accidental triggering. However, in a preferred embodiment, at least two buttons must be operated at the same time to minimize accidental triggering of the panic function. For example, both buttons 511 can be panic buttons so that the user must press both buttons 511 to enable the panic function. Alternatively, a single panic button 511 must be pressed simultaneously with another selected button, such as the YES button, to activate the panic function.

In another embodiment of the panic function, the wireless transceiver in the ambulatory patient monitor 20 may provide voice communication. In this embodiment, when the communications unit 30 is connected to the remote controller software 410, the caregiver can talk to the patient. Voice communications from the caregiver are relayed from the communications unit 30 via its transceiver to the transceiver in the ambulatory patient monitor 20.

The patient/user may also record a voice request in the ambulatory patient monitor 20 transmit the recorded voice message to the communications unit 30. The communications unit 30 then transmits the recorded voice message to the caregiver at the remote location. For example, the patient presses the "panic" button. The patient monitor 20 announces, "Speak at the end of the beep." The patient speaks for some period of time. The patient monitor 20 beeps during the recording period so the patient knows his message is being recorded. At the end of the recording session, the patient monitor indicates that a message is pending. When the communications unit 30 polls the patient monitor 20, it responds with "Message Pending." The communications unit 30 requests the message. The patient monitor 20 sends the message, which is transmitted by the communications unit to the caregiver. Then the communications unit sends an acknowledgement to the patient monitor 20. The patient monitor displays the message, "Message Sent" to the patient.

In another embodiment of the panic function, the ambulatory patient monitor can be programmed so that different sequences of the button pressings can be used to contact different people. For example, pressing the panic button 511 and the Yes button 520 may be programmed to contact a patient's family member. Pressing two Panic buttons 511 may be programmed to contact the caregiver. Pressing the Panic button 511 and the No button 520 may be programmed to contact an emergency service In each case, when the ambulatory patient monitor 20 generates the panic signal, which is received by the communications unit 30, the communications unit dials the appropriate telephone umber and establishes contact via telephone or other telecommunications lines.

Sensors

Four sensor/medical devices may be connected to interface circuits of ambulatory patient monitor 20.

Electrocardiogram. The electrocardiogram 217 is one of the preferred modules in ambulatory patient monitor 20. ECG signals from three ECG electrodes 217A, 217B, 217C are provided to ECG amplifier 212. The output of amplifier 212 is applied to amplifier 213 which is connected to input/output ports of microcontroller 201. ECG 217 detects signals from a single lead (2 active electrodes plus a ground electrode) located on the chest of the patient. These signals are recorded and stored as a monitor-bandwidth electrocardiogram.

Referring to FIGS. 9A–9D, interface circuits 212, 213 couple to ECG electrodes 217 via connector J2. The detected signals are first provided to a defibrillation circuit comprising diodes D1, D2, D3, D4, Zener diodes VR1 and VR2 and ferrous beads L1, L2, L3 and L4. The are provided to an amplification circuit and then through a tunable notch filter circuit to provide ECG signal A. ECG signal A is provided to pin 43 of microcontroller 201. The ECG amplification circuit provides several features: inputs from are protected from high voltage defibrillator discharges, electromagnetic interference (EMI) and electrostatic discharge (ESD); electrode leadoff detection; high input impedance (greater than 100 megohms); adjustable gain with a range of from 400 to 2000. Additionally the input and amplifier is optically isolated, the circuit uses low power (about 40 milliwatts), provides selectable gain settings of 0.5, 1.0 and 2.0 V/mV. The notch filter has a center frequency adjustable for 50 Hz or 60 Hz operation (so the unit can utilize foreign or domestic line power).

The ECG lead-off detection functions to detect when an electrode has lost connection to the patient's body. When all three electrodes 217A, 217B, 217C are connected, a small DC current of about 0.035 microamps is passed through electrodes 217C (LL) and 217A (RA) and through electrode 217B (RA) back to isolated common. This current is generated by two 100 megohm pull-up resistor, R4 and R5, which are connected from the isolated 3.5 VDC supply (VI+) to electrode inputs for LL and RA. In this condition, the voltage at electrode inputs LL and RA is above V. When one of these electrodes is disconnected, the voltage at one or both of the LL or RA inputs is pulled up to above 1 VDC. This voltage is transferred to the output of amplifiers U1A or U1B. This amplifier output voltage drives a current through D5 or D6 into the base of Q1 to turn it on. When Q1 is on, current flows through the input to optical coupler OC1 and turns on the output phototransister in OC1. When the output phototransistor in OC1 is turned on, it pulls the lead-off line to a logic low level indicating to the microcontroller 201 that lead-off is activated.

The performance of the ECG module shall meet the requirements of ANSI/AAMI, EC13, ANSI/AAMI ES1, ANSI/AAMI EC38 (Type III) for an apparatus with isolated patient connection when connected to the communications unit 30. Pacemaker spike detection is not required. The input leads attached to the patient are defibrillator-protected. The electrocardiogram module is preferably operated intermittently in order to reduce the data storage requirements and power consumption of the monitor 20.

Only raw ECG data is stored and provided to the caregiver. All analysis or processing of ECG data is done by the caregiver. Thus no ALARMS are ever generated as a result of any detected and stored ECG data. If electrode lead-off condition or a broken lead wire is detected by the monitor 20, an ALERT is triggered. Reconnecting the electrode within a predetermined period of time will clear the ALERT signal. If the patient presses the EVENT KEY or an ALARM condition occurs, monitor 20 stores ECG data for 1 minute prior to the EVENT or the ALARM.

ECG sampling is performed continuously at 240 samples per second. A single analog-to-digital channel converts the analog signal to 8 bit data. The data are recorded to Temporary Memory 223 as it is converted. An algorithm is used to determine an appropriate gain level. This gain level control drives two control lines to the ECG measurement system programmable gain amplifier. The output from the ECG Monitoring Measurement System is preferably 240 bytes each second.

Pulse Oximetry. The pulse oximetry sensor 214 measures pulse rate from a signal associated with the pulse oximeter and measures arterial blood oxygen saturation from a finger sensor through use of non-invasive techniques. Preferably pulse oximeter sensors provided by NONIN are used. These sensors operate using photoemitters and photodetectors to sense pulse rate and oxygen content non-invasively. The output of the pulse oximeter sensors are provided to oximetry module 207 which converts them to a RESP signal E which is provided to pin 44 of microcontroller 201. A respiratory lead off signal is also provided to EEPROM/RAM 224 at pin 33.

ALARMS may be set for high and low pulse rates and for high and low oxygen saturation in accordance with INSTRUCTIONS from the remote controller (stored in the Instruction Table.) The ambulatory patient monitor 20 detects sensor errors or low perfusion conditions and provides an ALERT signal. The ambulatory patient monitor 20 stores pulse rate and oxygen saturation data for one minute prior to an EVENT mark or ALARM condition.

Arterial Pulse Oxygen Saturation ($S_pO_2$): The pulse oximetry module 214 uses standard and clinically accepted indirect techniques to read the arterial oxygen saturation through transmittance or reflectance sensors. Oxygen saturation and pulse rate are computed by the monitor 20 using accepted techniques and algorithms. The pulse oximetry module 214 measures physiological values of arterial oxygen saturation preferably over a range of 70–99%. The pulse rate measurement is preferably over a range from 20 to 300 beats/minute.

The resolution of the pulse oximeter 214 is preferably 1% oxygen saturation and the accuracy is expected to be +/–3% oxygen saturation. The resolution of the pulse rate subsystem is preferably 1 beat per minute and the accuracy is expected to be +/–3%. The time between power on and the stabilization of readings of both oxygen saturation and pulse rate shall preferably not exceed 10 seconds. The power requirements shall preferably not exceed 100 milliwatts during operation with the sensor turned on. In order to conserve power and memory requirements, the pulse oximetry unit 214 may be turned on for 10–20 seconds out of every minute.

The pulse oximetry unit 214 requires about 10 seconds to stabilize from power-on. When enabled, the measurement system is then powered continuously. At power-on, it begins sending 3-byte serial data (9600 baud, 8,N,1) at a frame rate of one frame per second. The first byte contains status, the second byte contains heart rate data, and the third byte contains $S_pO_2$ data. Each frame is examined for acceptability. Frames status with good, low or marginal perfusion status are acceptable. A timeout is set if there is a succession of unacceptable frames or absent frames. An elapsed timeout causes an ALERT condition. The receipt of acceptable frames resets the timeout alarm, and resets the timeout timer.

Microcontroller 201 drives the oximetry module 214 and interface circuit 207 in accordance with a task flow routine. Referring to FIGS. 15A–15D, when the oximetry unit is powered on, the microcontroller 201 begins the oximetry routine at step 700. First the time reference is set at step 702. Then the routine waits for a communication signal at step 704, looping until one is received. When the signal is received, the Calc flag is reset at step 706. A 3 serial character burst is expected every second. At step 708 the routine checks if more than one second has elapsed. If yes, the routine sets an ALERT at step 710 and branches to step 722.

If less than one second has elapsed, the routine checks if more than one tick of the counter has elapsed at step 712. If yes, the buffer is reset and the buffer count is reset at step 714. If only one tick has elapsed, the routine puts the received character in the oximetry buffer and increments the counter at step 716. At step 718 the routine checks if the count is greater than three. If yes, at step 720 the calc flag is set, and data is coupled from the oximetry buffer to the temporary memory 223.

If not, the routine checks if the clac flag is set at step 722. If the calc flag is not set the routine branches to step 736. If the calc flag is set, the routine checks the quality of the $S_pO_2$ reading at step 724. If the data is bad, routine checks if the alert flag has been set at step 726. If the flag is not set, the routine sets the flag and the alert timer at step 728 and branches to step 736. If the flag is already set, the routine checks if the alert has persisted for more than ten seconds at step 732. If true, the routine sets the alert at step 734 and continues to step 736. If the data is not bad, the routine resets the alert and the alert flag at step 730 and continues to step 736.

At step 736, the routine checks if the calc flag is set, an alert is not pending and a prescription (Instruction) is in force. If false, the routine jumps to step 786 and ends. If true, the routine checks if the heart rate is at the heart rate high limit as defined in the Instruction Table at step 738. If true, the routine checks if the flag is set at block 740. If the flag is not set, the flag is set and the timer is set in accordance with the value in the Instruction Table at step 742 and the routine would branch to step 750.

If the heart rate flag is set, the routine checks if the duration has expired in step 744. If it has, the routine sets the heart rate high alarm at step 746 and continues to step 750. If the duration has not expired, the routine continues to step 750. If the heart rate data is not at the high limit, the routine resets the flag at step 748.

At step 750 the routine checks if the heart rate data is at the low limit. If the heart rate data is at the low limit, the routine checks if the flag is set at step 752. If the flag is not set, the routine sets the flag and the timer at step 754 and continues to step 762. If the flag is set, the routine checks if the timer has expired at step 758. If it has, the routine sets the low heart rate alarm and continues to step 762. If the duration has not expired, the routine continues to step 762. If the heart rate data is not at the low limit, the routine resets the flag at step 760 and continues to step 762.

At step 762, the routine compares the data to the $S_pO_2$ value in the Instruction Table. If the data is at the high limit, the routine checks if the flag is set at step 764. If the lag is not set, the routine sets the flag and sets the timer at step 766 and continues to step 774. If the flag is set, the routine checks if the duration has expired at step 768. If the duration has expired, the routine sets the $S_pO_2$ high alarm at step 770 and continues to step 774. If the $S_pO_2$ data is not at the high limit, the routine resets the flag at step 772 and continues to step 774.

At step 774, the routine checks the data to the $S_pO_2$ low limit. If the data is at the low limit, the routine checks if the flag is set at step 778. If the flag is not set, the routine sets the flag and the timer at step 782 and continues step 766. If the flag is set, the routine checks if the timer has expired at step 780. If the timer has expired, the routine sets the $S_pO_2$ low alarm and continues to step 786. If the duration has not expired, the routine continues to step 786. If the $S_pO_2$ data is not at the low limit, the routine resets the flag at step 776 and continues to step 786. At step 786, typically, the routine will branch to step 700.

Heart Rate (Pulse Rate). The heart rate data used by the system 20 can be acquired from three different modules: (1) Pulse Oximetry Module 214, (2) Blood Pressure Module 54, and (3) Electrocardiogram Module 217. The primary source of these data is the Pulse Oximetry Module 214, since it will operate more continuously than the others. Since the Blood Pressure Module 54 is coupled to the communications unit 30, the heart rate data derived form this measurement is not body-worn. Only the data from the pulse oximetry module 214 is used for ALARM and data transfer to the caregiver's base station.

Temperature. A temperature sensor 216 measures the body core temperature. ALARMS may be set for high and low temperatures in accordance with INSTRUCTIONS received from the remote controller. The ambulatory patient monitor 20 detects sensor failures and sensor-off conditions and provides an ALERT signal. The ambulatory patient monitor 20 stores temperature data for one minute prior to an Event mark or Alarm condition.

Figure 21A:
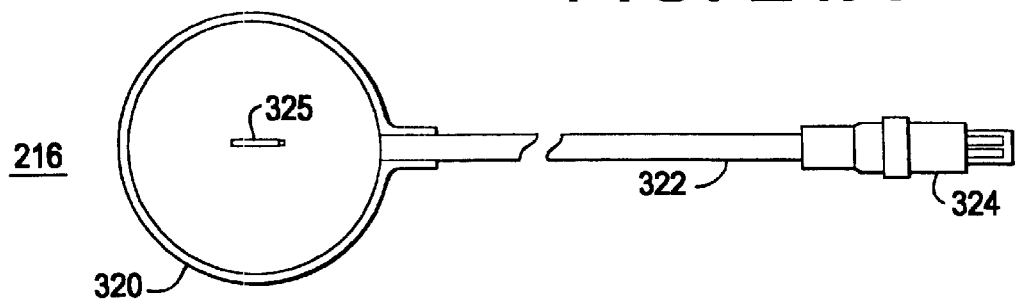
Figure 21B:
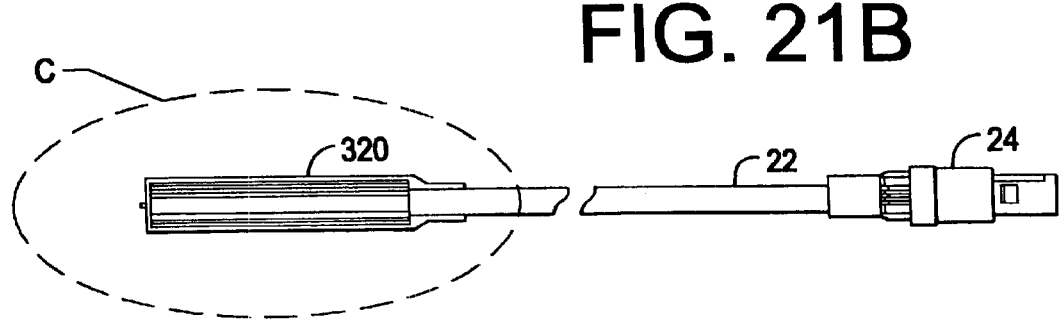
Figure 21C:
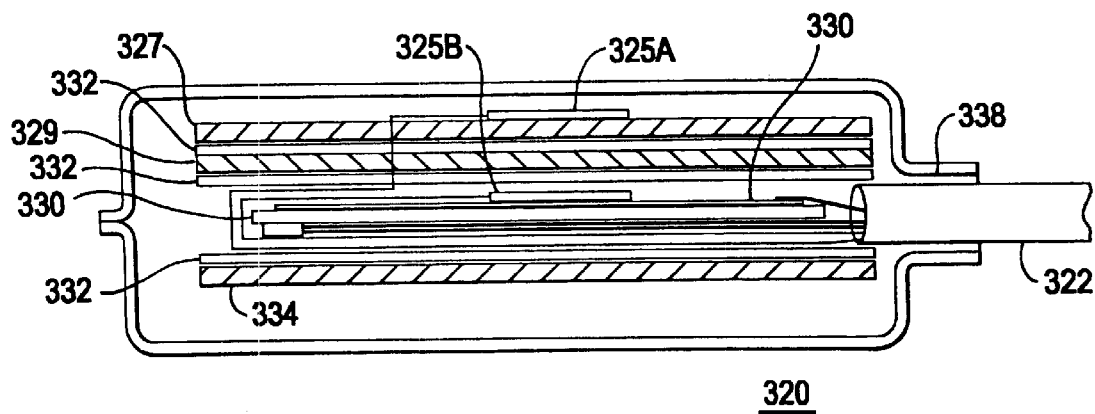

Referring to FIGS. 21A–21C, details of a preferred core temperature sensor 216 are shown. Sensor 216 includes a sensing head 320 connected to a cable 322 at one end and connector 324 at the other end. Connector 324 is coupled with temperature interface circuit 209 of patient monitor 20. The sensing head 320 includes two temperature sensing elements 325A, B. Preferably elements 325 are thermistors or thermocouples. Thermistors 325A, B are separated from one another by a composite layer of two generally circular insulating foam layers 327 and 329 and a circular layer of adhesive 332. Foam layers 327 and 329 provide a thermally insulating annular ring around and over the elements 325A, B. This design is effective for preventing both normal and lateral heat loss from the sensors.

The first thermistor 325A is disposed centrally within and on top of insulating foam layer 327 and is positioned by direct contact with the surface of the skin. This thermistor is the thermistor closest to the patient's skin. The second thermistor 325B is separated from the first thermistor by the composite foam/adhesive layers 327, 332, 329 and disposed along the same vertical line as the first thermistor 325A. A second adhesive layer 332 attaches a film heater element 330 directly over the second thermistor 325B. A thin layer of thermally insulating foam 334 covers the heater 330 and is held in place by a third adhesive layer 332. The entire assembly is enclosed in a heat shrink wrap 338 of a thermally transmissive material. Thus, a region of "zero" heat flow is actively created across the layers of the skin which causes temperature sensor 325A, located at the surface of the skin to read the same temperature as if it were located deeper within the body, beneath the skin's surface.

The temperature interface circuit 209 uses a feedback control loop to control the temperature of the film heater to match the skin temperature. A full proportional control strategy is used to control the temperature of the heater 330 in that control action is taken proportional to the error to drive the error to zero. This overcomes the thermal hysteresis and temperature variation characteristics of an ON/OFF ("bang/bang") controller. Additionally, several safety shutdown provisions are provided to limit current to the heater element to prevent overheating. ALARMS and ALERTS are generated to notify the patient when any potential system failure conditions a detected.

Figure 10A:
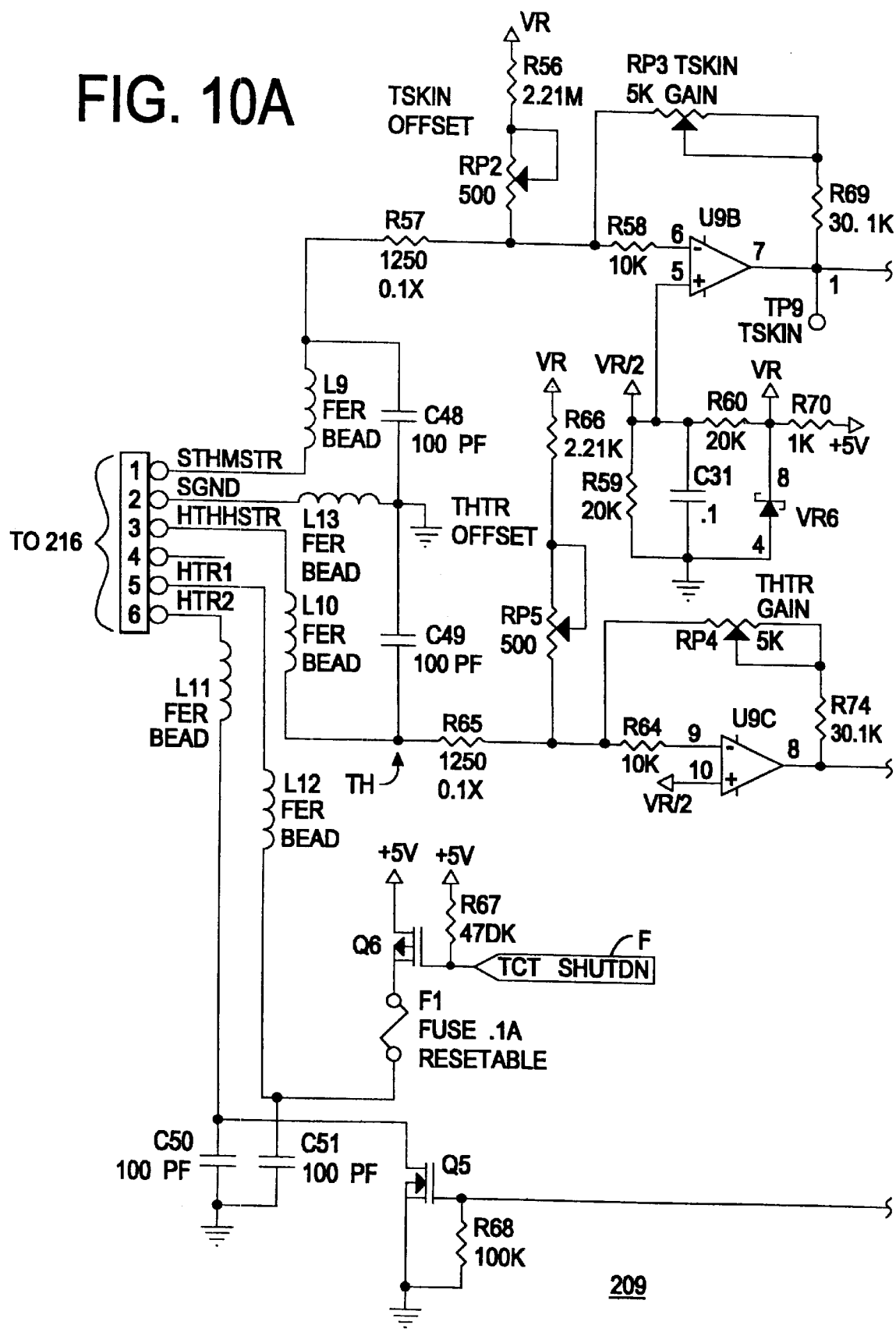
FIGS. 10A–10B are a circuit diagram of the core temperature sensor interface circuit.
Figure 10B:
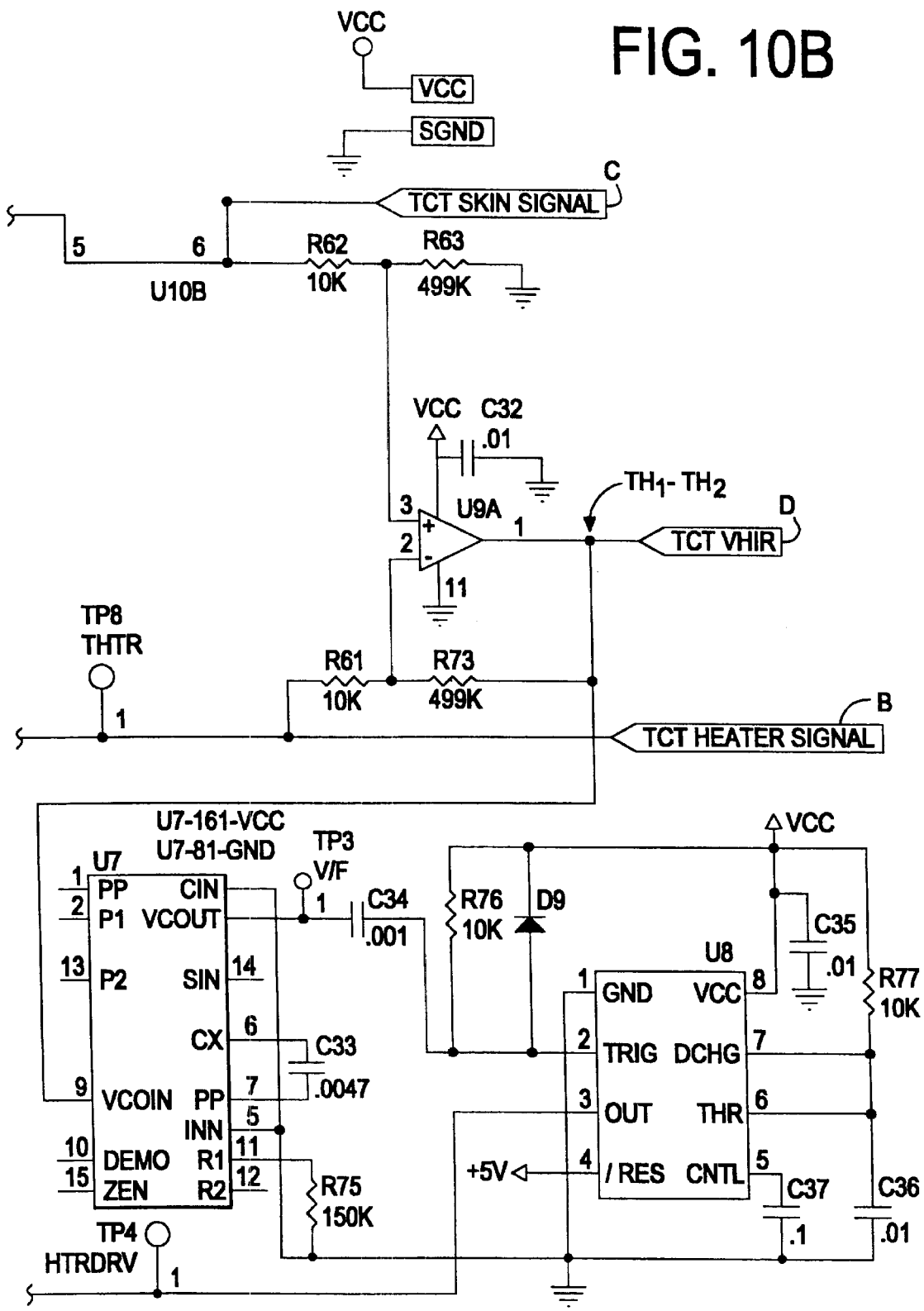

Referring to FIGS. 10A–10B, connector J6 couples with connector 324 of temperature sensor 216. The heater signal which controls the amount of current to the heater 330 is provided from pin 3 OUT of timer U8. Fuse F1 limits the current to the heater to about 100 milliamps. When the fuse F1 opens, TCT shutdown signal F is provided to pin 24 of microcontroller 201. The skin temperature signal C is compared with the heater temperature signal B in comparator U9A. The output of U9A is the error signal D which is used to provide proportional control. This error signal D is applied to voltage controlled oscillator U7 which drives timer U8. When the system is operating in a quiescent state, a small error signal is present and is used to drive the heater to produce sufficient heat to cancel any heat loss from the skin and provide nearly zero flow conditions under the sensor assembly. Signals B, C and D are provided to pins 47, 45 and 49 respectively of microcontroller 201.

The temperature sensor 216, when enabled, is powered continually. The digitized temperature channel is scaled in degrees Fahrenheit within the range 80 to 105 to a resolution of 0.1 degree (which may also be converted to degrees Celsius as required). Timeouts for ALERT conditions similar to those in the Oximetry Measurement System are used. The output for temperature is one byte.

Respiration. Respiration rate is preferably detected from a nasal cannula sensor which contains thermistor sensors for each nostril and shall be active whenever the instruction calls for monitoring, day or night or both. The range of the measured respiration rate shall preferably be from 5 to 40 breaths per minute.

Figure 11A:
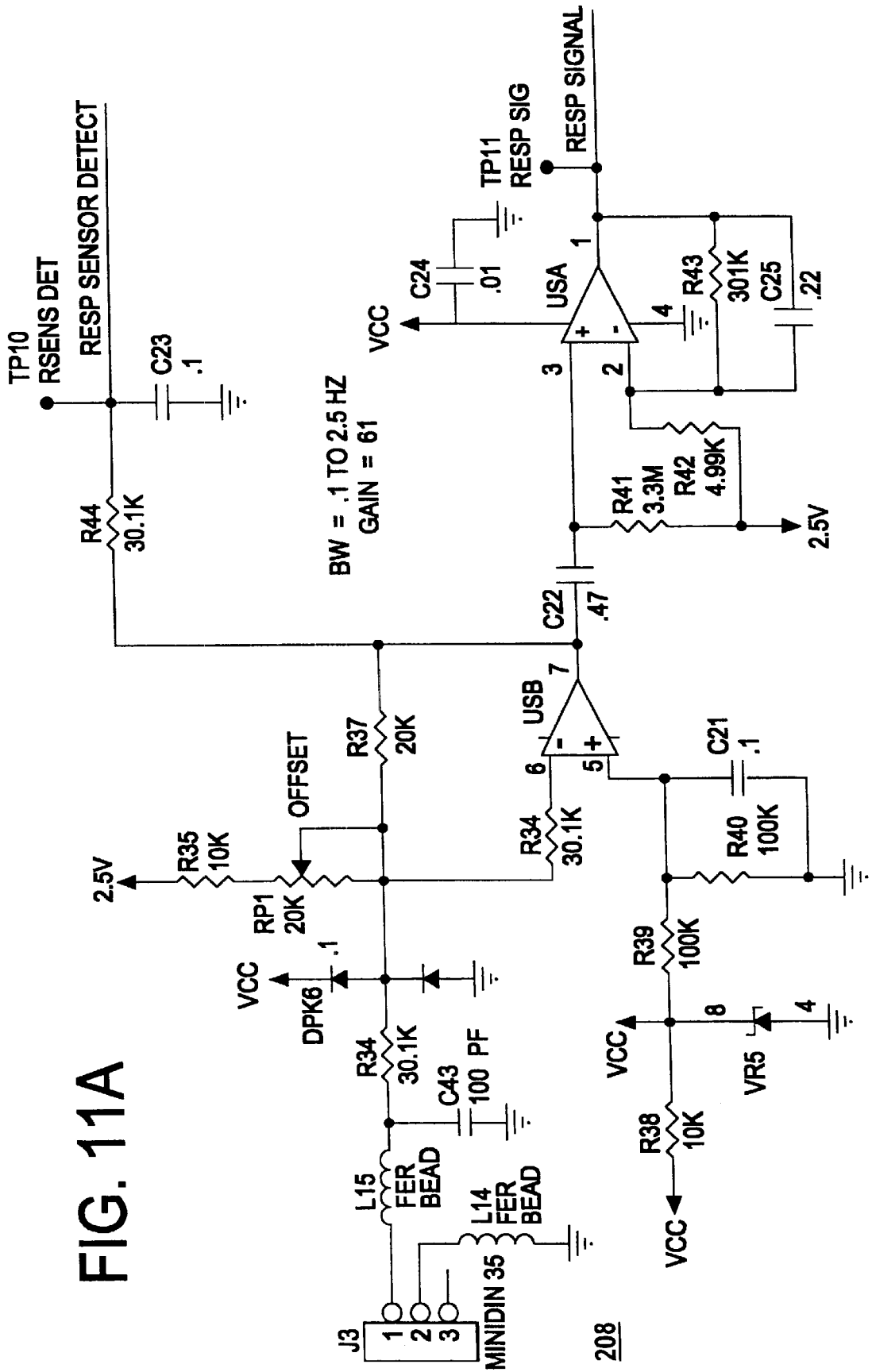
FIGS. 11A–11C are a circuit diagram of the respiration interface circuit.
Figure 11B:
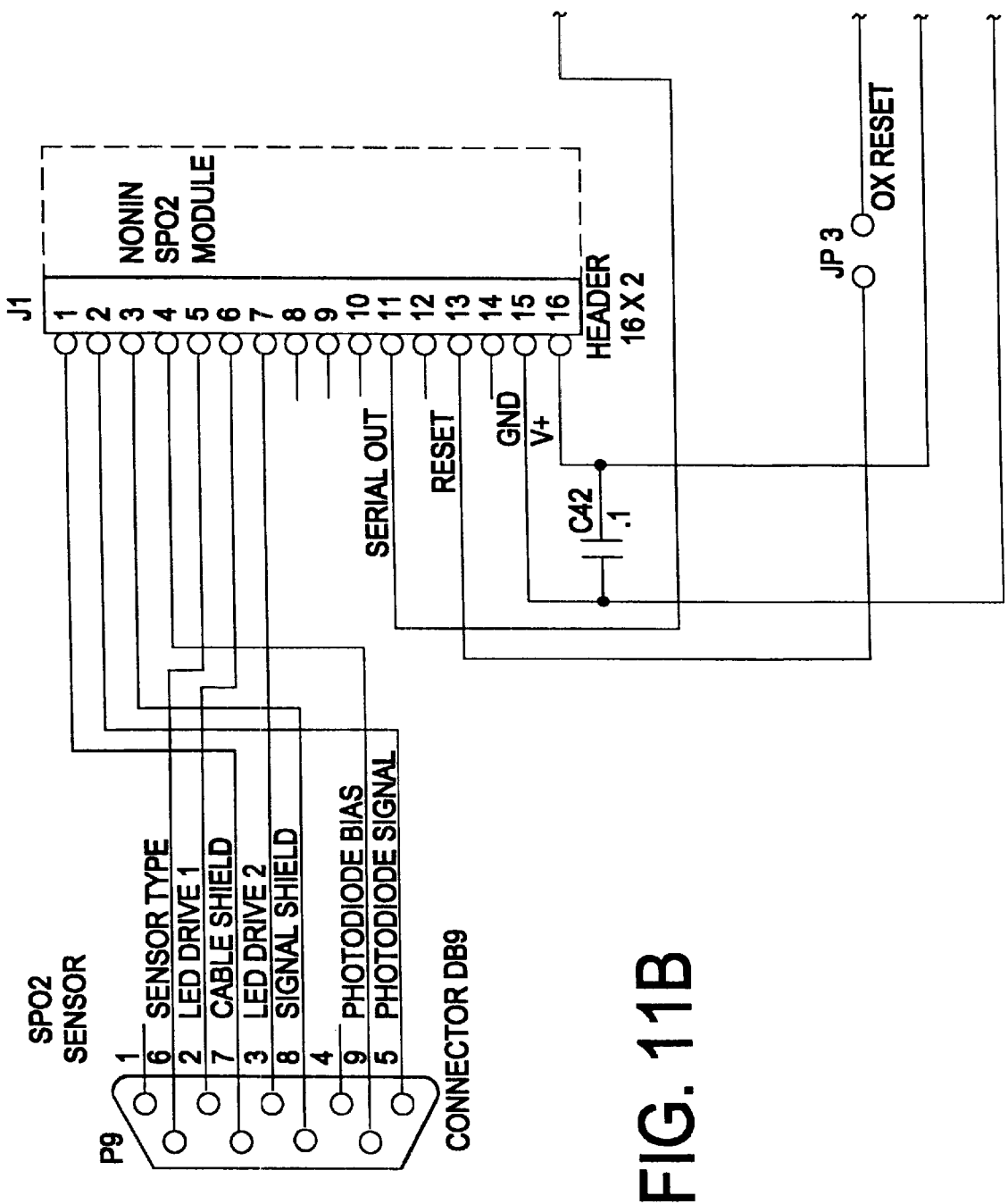
Figure 11C:
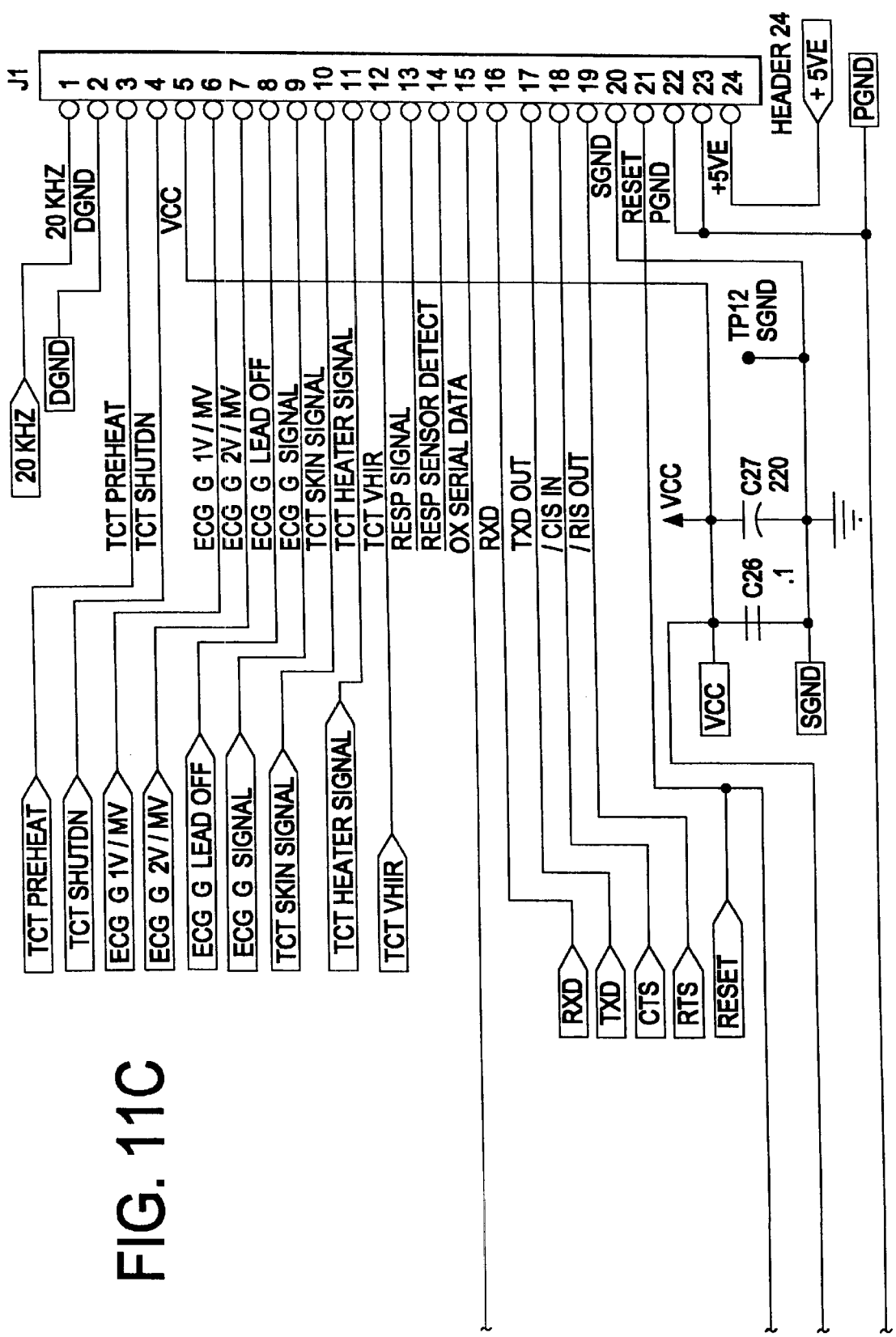

A respiration sensor 215 measures the approximate respiration rate from temperature changes in the inspired and expired air from the nostrils of the patient using a novel respiration rate algorithm (described below). ALARMS may be set for high and low respiration rates in accordance with INSTRUCTIONS received from the remote controller. Respiration rates are recorded and stored in the flash memory 222. The ambulatory patient monitor 20 detects a sensor or lead wire failure and provides an ALERT signal. Signals from respiratory sensor 216 are provided to respiratory interface circuit 208. Details of respiratory interface circuit 208 are shown in FIGS. 11A–11C. The ambulatory patient monitor 20 stores respiration data in memory 224 for one minute prior to an Event mark or Alarm condition.

Referring to FIGS. 11A–11C, interface circuit 208 provides the output of respiratory sensor 215. Preferably a commercially available sensor is used.

Respiration waveform data are scanned from a single analog channel at 10 samples/second. When this measurement system is enabled, power remains ON continuously on the measurement system. The Respiration waveform data is digitized and recorded to Random Access memory 223. An algorithm (described below) then uses the memory 223 to determine relative peaks in the digitized waveform. From the number of samples determined between each detected peak, the instantaneous respiration rate is derived. A weighted average respiration rate is calculated using a weighted average technique similar to that used for the Oximeter Measurement System. The respiratory measurement system outputs one byte, the respiratory rate in breaths per minute.

While the sensors are preferably intended to be for single patient use, the ambulatory patient monitor 20 itself can be used by multiple patients. The ambulatory patient monitor 20 can be cleaned and disinfected between patients and used with new sensors for use with a new patient.

Microcontroller 201 drives the respiration sensor 215 and respiration interface circuit 208 and the temperature sensor 216 and temperature interface circuit 209 in accordance with a task flow routine. Referring to FIGS. 16A–16E, when the temperature sensor 216 and the respiration sensor 215 are powered on, the microcontroller 201 begins the temperature and breath rate routine at step 800. This routine is repeated every 100 milliseconds. At step 802, the routine checks if the respiratory leads are properly attached. If not, the routine checks if the alert flag is set at step 804. If the flag is not set, the routine sets the flag and initializes the timer at step 806 and continues to step 816. If the alert flag is set, the routine checks if the timer has expired at step 808. If the timer has expired, the routine sets the respiration alert at step 810 and continues to step 816. If the timer has not expired, the routine continues to step 816. If the respiratory lead is properly attached, the routine resets the timer and the flag at step 812 and resets the ALERT at step 814. At step 816, the routine performs the respiratory rate algorithm (see FIGS. 13A–13B and description).

At step 818 the routine checks if the current respiratory rate has been determined. If not, the routine branches to step 846. If the rate has been determined, the routine checks if an ALERT is pending and the Instruction is current at step 820. If not, the routine branches to step 846. If true, the routine checks if the current rate is higher than the high limit at step 822. If true, the routine checks if the flag has been set at step 824. If the flag is not set, the routine sets the flag and the timer at step 826 and continues to step 834. If the flag is set, the routine checks if the timer has expired at step 828. If the timer has expired, the routine sets the high ALARM at step 830 and continues to step 834. If the current rate is not higher than the high limit, the routine resets the flag and timer at step 832 and continues to step 834.

At step 834, the routine checks if the current rate is lower than the low limit. If true, the routine checks if the flag has been set. If the flag has not been set, the routine sets the flag and the timer at step 838 and continues to step 846. If the flag is set, the routine checks if the timer has expired. If the timer has expired the routine sets the Low ALARM at step 842 and continues to step 846. If the timer has not expired, the routine continues to step 846. If the current rate is not lower than the low limit, the routine resets the flag and the timer at step 844.

At step 846 the routine checks if the temperature lead is properly connected. If not properly connected, the routine checks if the flag has been set at step 848. If the flag is not set, the routine sets the flag and initializes the timer at step 850 and continues to step 860. If the flag is set, the routine checks if the timer has expired at step 852. If the timer has expired, the routine sets the ALERT at step 854 and continues to step 860. If the timer has not expired, the routine continues to step 860. If the temperature sensor is properly connected, the routine resets the flag and the timer at step 856 and resets the ALERT at step 858.

At step 860 the routine calculates the current core temperature and then calculates a weighted average. At step 862 the routine checks if an ALERT is pending and an Instruction is current. If true, the routine continues at step 876. If not, the routine checks if the current temperature is greater than the high limit at step 864. If true, the routine checks if the flag is set at step 866. If the flag is not set, the routine sets the flag and the timer at step 868 and continue to step 876. If the flag is set, the routine checks if the timer has expired at step 870. If the timer has expired, the routine sets the ALARM at step 872 and continues to step 876. If the current temperature is not greater than the high limit, the routine resets the flag and the timer at step 874.

At step 876 the routine checks if the current temperature is lower than the low limit. If true the routine checks if the flag has been set at step 878. If the flag has not been set, the routine sets the flag and the timer at step 880 and continue to step 888. If the flag has been set, the routine checks if the timer has expired at step 882. If the timer has expired, the routine sets the alarm at step 884 and continues to step 888. If the current temperature is not lower than the low limit, the routine rests the flag and the timer at step 886 and continues to the end of the loop at step 886.

Alarms and Alerts

An ALARM is triggered whenever a physiological variable is measured which is outside of its prescribed limits stored in the Instruction Tables (see below). An ALERT is triggered for system and sensor failures (including misapplication of the sensor).—ALARMS must be treated with urgency and responded to in accordance with Instructions displayed on the display 219 or from the 15 speaker. The first response to an ALARM is to connect with the communications unit 30.

An ALERT or ALERT CHECK is a system test which checks the performance of the sensors and other system components against a set of pre-determined test limits. An ALARM or ALARM CHECK is a physiological data test limit that is set by the caregiver in the INSTRUCTION TABLE stored in the memory 224 of the ambulatory patient monitor 20. An ALARM Mode is the mode initiated in the ambulatory patient monitor 20 when an ALARM is tripped and data collected for one minute prior to the ALARM is transferred from the flash memory 222 to memory 224. Real-time data is also stored in memory 224 for one minute after the ALARM occurs.

Upon detection of an ALARM or ALERT, the programmable, ambulatory patient monitor 20 issues an audible and/or visual warning. The audible warning may be in tones or verbal instructions through a speech synthesizer. The visual warning may be through illuminated or flashing lights and/or an alphanumeric message on a display. When an ALARM is triggered, the power ON/OFF button 508 is disabled. The programmable, ambulatory patient monitor 20 may not be powered off until the ALARM is disabled by receipt of an appropriate signal from the caregiver.

The ALARM and ALERT warnings may, however, be disabled temporarily. Some patients may find it distracting to try to contact the caregiver while the ALARM warning is flashing or being repeated (in the case of a verbal message) . In these cases, the patient can disable the ALARM warning temporarily by pressing a HOLD or MUTE button 504. Pressing the MUTE button 504 disables the warnings for up to two minutes. ALERT warnings may also be disabled by pressing the HOLD or MUTE button 504.

ALARMS, ALERTS and the Back-up Audio Tone all have different tones. Each tone is repeated every ten seconds or at some other convenient preset interval. Voice instructions are repeated every fifteen seconds. Volume control 512 affects both tones and voice instructions, but cannot be used to turn them off. Activation of the Mute switch 504 silences the tones for up to two minutes at a time.

All ALARMS are automatically reset to the programmed INSTRUCTION values two minutes after they have been disarmed by the HOLD or MUTE button. ALARMS are locking and cannot be reset unless all conditions for release of the ALARM, including a reset signal from the caregiver, have been received. ALERTS are resettable by the patient and cleared whenever the problem causing the ALERT is corrected.

Priorities/Hierarchy. Providing for detection of various ALARM and ALERT conditions is essential to monitoring the patient's condition. The ambulatory patient monitor 20 is programmed to respond to ALARMS and ALERTS in accordance with predetermined priorities. These priorities can be varied by the caregiver depending on the needs of the patient and the specific equipment attached to the ambulatory patient monitor. If an ALARM occurs, the patient must contact the caregiver. If a second ALARM or an ALERT subsequently occurs, the action is the same: the patient must contact the caregiver.

If an ALERT occurs without an ALARM, the first action is for the patient to respond to the message on the display 219 and the voice annunciation (Instruction). In most cases, following the instructions on the display or from the annunciator will clear the ALERT. However, if the ALERT cannot be cleared by the patient or in some special situations, the action is to contact the caregiver. If an ALERT occurs, followed by an ALARM, the first action required is for the patient to contact the caregiver. Any ALARM has priority over the EVENT mode and will immediately switch the ambulatory patient monitor 20 from EVENT mode to ALARM mode. No further EVENT inputs will be accepted until the ALARM is cleared.

To insure no stored data is lost, if the ambulatory patient monitor 20 displays a Memory Full Alert, the patient is directed to contact the caregiver. In some cases, a Battery Low Alert may cause the ambulatory patient monitor 20 to display the contact the caregiver message in order to prevent an ALARM while changing the battery. If the ambulatory patient monitor 20 detects that the stored INSTRUCTIONS pertaining to sensor value ranges might be corrupted, the ambulatory patient monitor 20 displays the contact the caregiver message.

Table 1 lists example ALARMS and the preferred visual and auditory warnings to be displayed by monitor 20. Table 2 lists example ALERTS and the preferred visual and auditory warnings to be displayed by monitor 20. Other messages and sequences of auditory tones may be used.

TABLE 1

ALARMS

| TRIGGER | ALARM | DISPLAY | VOICE | PATIENT ACTION |
|---|---|---|---|---|
| Pulse Oximetry Low | Beep #1 per Instruction | contact caregiver OXYGEN LOW | "Contact caregiver oxygen too low" | Connect to Communication Unit |
| Heart Rate High | Beep #1 per Instruction | contact caregiver PULSE RATE HIGH | "Contact caregiver pulse rate too high" | Connect to Communication Unit |
| Heart Rate Low | Beep #1 per Instruction | contact caregiver PULSE RATE LOW | "Contact caregiver pulse rate too low" | Connect to Communication Unit |
| Respiratory Rate High | Beep #1 per Instruction | contact caregiver BREATHING FAST | "Contact caregiver breathing too fast" | Connect to Communication Unit |
| Respiration Rate Low | Beep #1 per Instruction | contact caregiver BREATHING SLOW | "Contact caregiver breathing too slow" | Connect to Communication Unit |
| Temp High | Beep #1 per Instruction | contact caregiver TEMP HIGH | "Contact caregiver temperature too high" | Connect to Communication Unit |
| Temp Low | Beep #1 per Instruction | contact caregiver TEMP LOW | "Contact caregiver temperature too low" | Connect to Communication Unit |

TABLE 2

ALERTS

| TRIGGER | ALARM | DISPLAY | VOICE | PATIENT ACTION |
|---|---|---|---|---|
| Memory Full | Beep #2 approx. 4 min. before | contact caregiver TRANSFER DATA | "Contact caregiver for data transfer" | Connect to Communication Unit |
| Battery Low | Beep #2 on occurrence | CHANGE BATTERIES NOW | "Replace batteries now" | Replace primary battery in APM |
| Pulse Oximetry Error | Beep #2 on occurrence | FINGER SENSOR RE-CONNECT | "Check finger sensor" | Re-apply sensor |
| Heart Rate Error | Beep #2 in occurrence | FINGER SENSOR RE-CONNECT | "Check finger sensor" | Re-apply sensor |
| Respiration Error | Beep #2 in occurrence | NASAL SENSOR RE-CONNECT | "Check nasal sensor" | Re-position sensor |
| ECG Error | Beep #2 on occurrence | ELECTRODE RE-CONNECT | "Check electrodes" | Re-apply sensors |
| Temperature Error | Beep #2 on occurrence | TEMP SENSOR RE-CONNECT | "Check temperature sensor" | Re-apply sensor |
| System Malfunction | Beep #1 and #2 on occurrence | contact care caregiver | "Contact caregiver for instruction" | Contact caregiver |
| Event | Beep #2 on occurrence | EVENT | None | None required |
| Continuous | No | Time of Day (12 hr or 24 hr format) | None | Diary Log |

Event Recording

The ambulatory patient monitor 20 includes an EVENT key 510 (switch or contact) which the patient (or caregiver) can use to initiate an EVENT recording. For example, if the patient is experiencing symptoms, equipment problems occur, pain is notable, medications are administered, or an accidental injury occurs, the EVENT recording key 510 may be selected. When the EVENT key 510 is selected, the ambulatory patient monitor 20 stores the following information: ECG, respiration rate, temperature, pulse oximetry and pulse rate from one minute prior to the EVENT to five minutes after the EVENT. After the Event key is pressed, the sampling data rate for all sensors is increased for five minutes after the EVENT, then the sampling rate reverts back to the prior sampling rate. This enables the collection of a greater number of data points for use in diagnosis. If the EVENT key 510 is pressed again, before or after the five minute period has elapsed, the event time is reset for an additional five minutes of data sampling.

In normal Run Mode (modes are described below) when an Instruction Table interval has arrived for a specific measurement, a data record will be recorded to Main Recording Memory 222 as well as to Temporary Recording Memory 223. As a rule, a record will be recorded to Main Recording Memory 222 for each time that any bit in an internal 32 bit status register has changed state. It is possible for a caregiver at a host station to perform an audit of the ambulatory patient monitor 20 by examining the status of retrieved records. The internal status register reflects status of ALERTS, ALARMS, memory and other internal parameters.

In Alarm Mode, the previous 60 seconds, or sixty records, from Temporary Recording Memory 223 are copied to Main-Recording Memory 223. Then real-time records are recorded to both Temporary Recording Memory 223 and to the Main Recording Memory 222 at one record per second until a data link command is received which terminates the Alarm Mode.

In Event Mode, the previous 60 seconds or 60 records, from Temporary Recording Memory 223 are copied to Main Recording Memory 222. Then real-time records are recorded to both Temporary Recording Memory 223 and to the Main Recording Memory 222 for a time limit determined by the Instruction Table. In Idle Mode, no records are recorded. Real-Time Clock (RTC) 221 places an RTC stamp on every record either in Temporary Recording Memory 223 or Main Recording Memory 222.

Figure 14A:
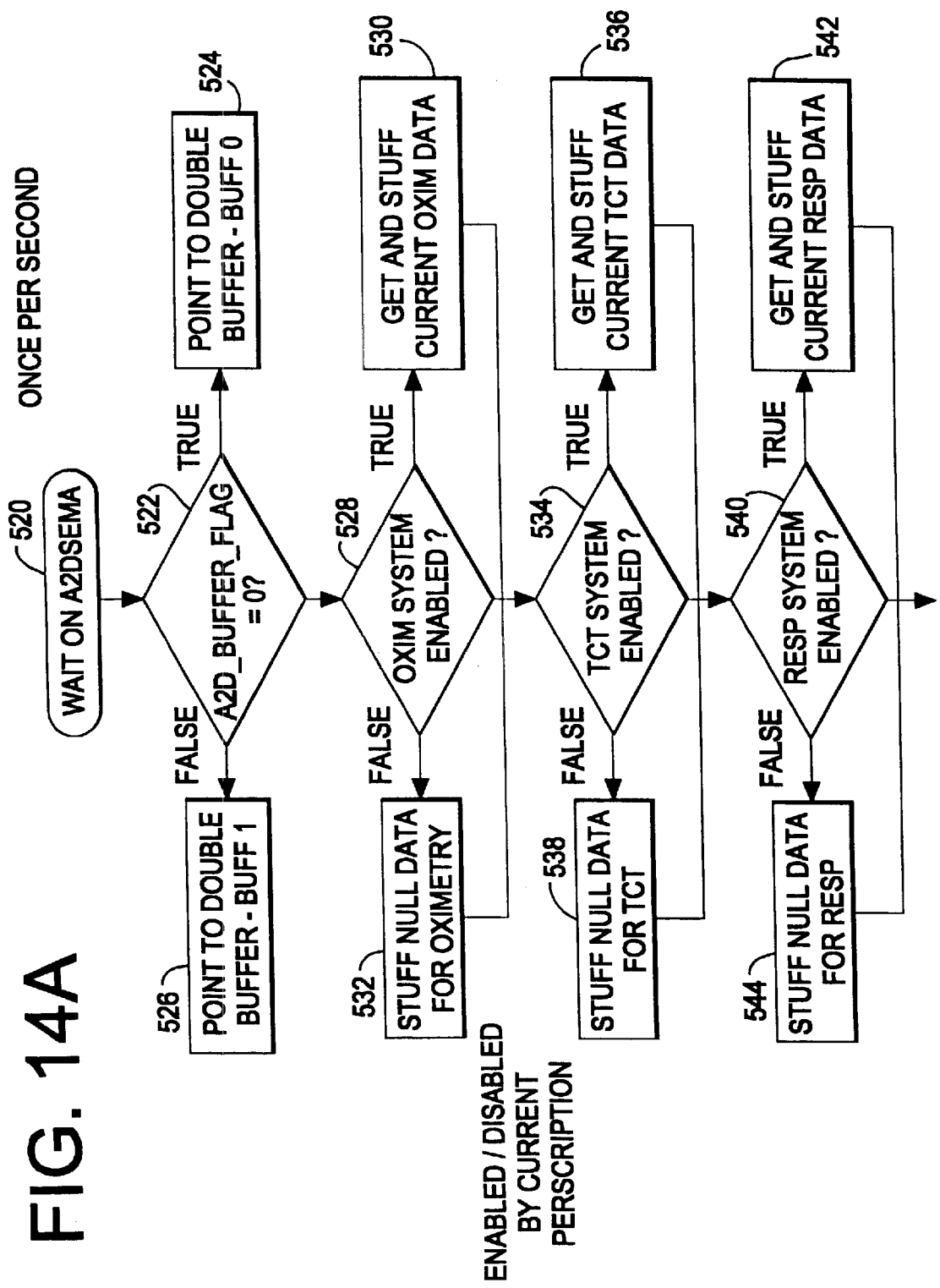
FIGS. 14A–14C are a flow chart of the memory management task flow in the ambulatory patient monitor.
Figure 14B:
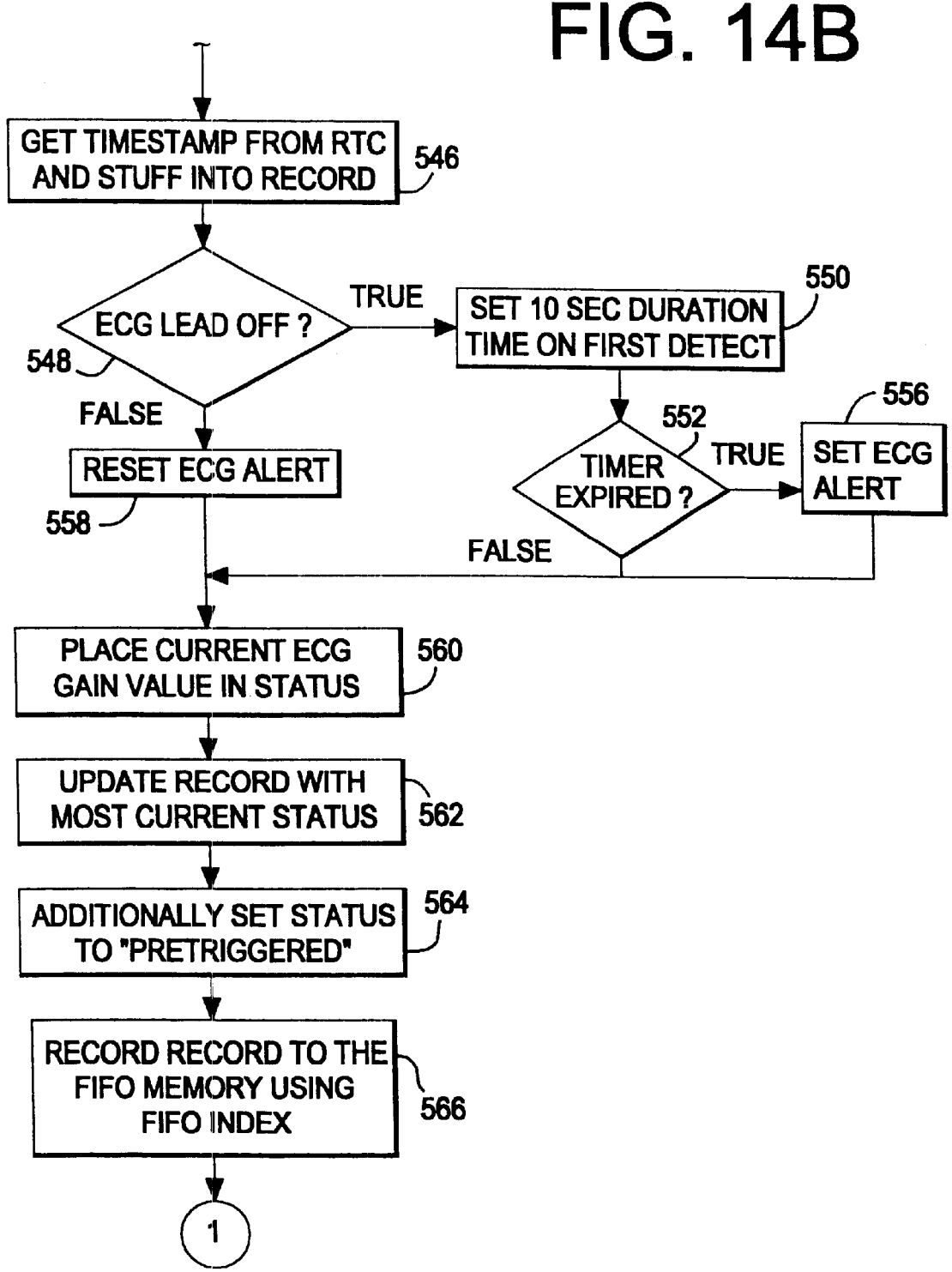
Figure 14C:
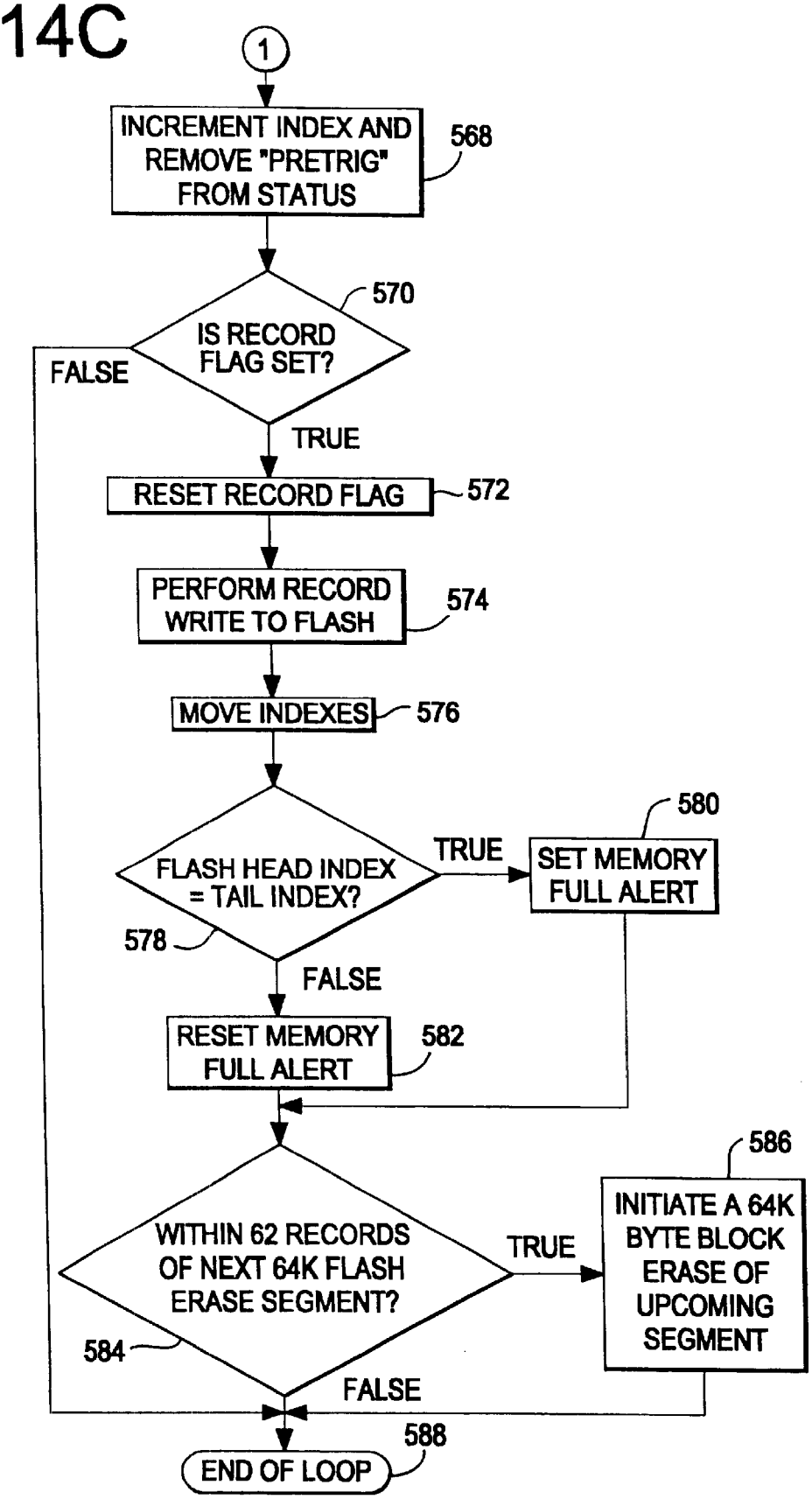
Figure 15A:
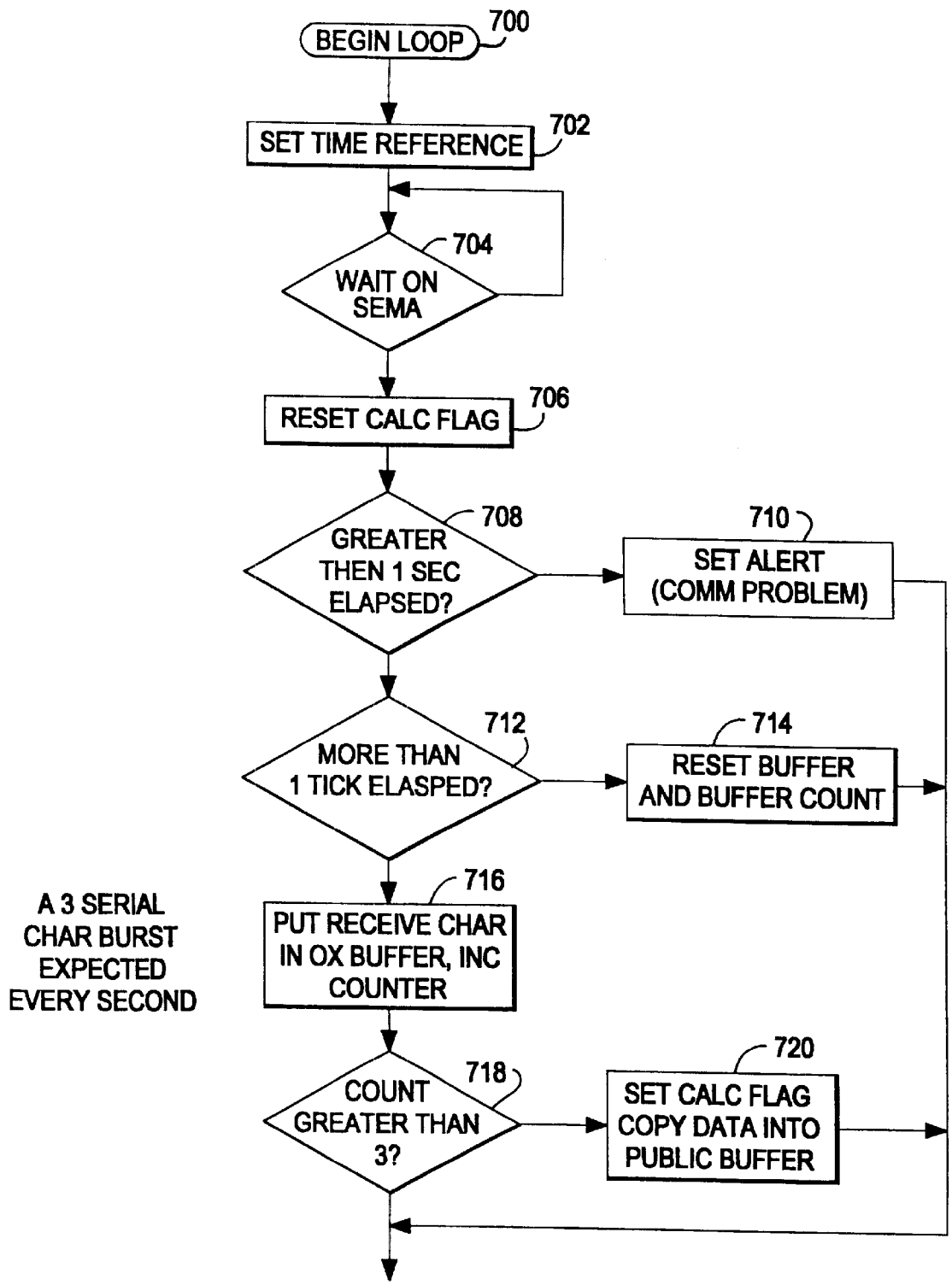
Figure 15B:
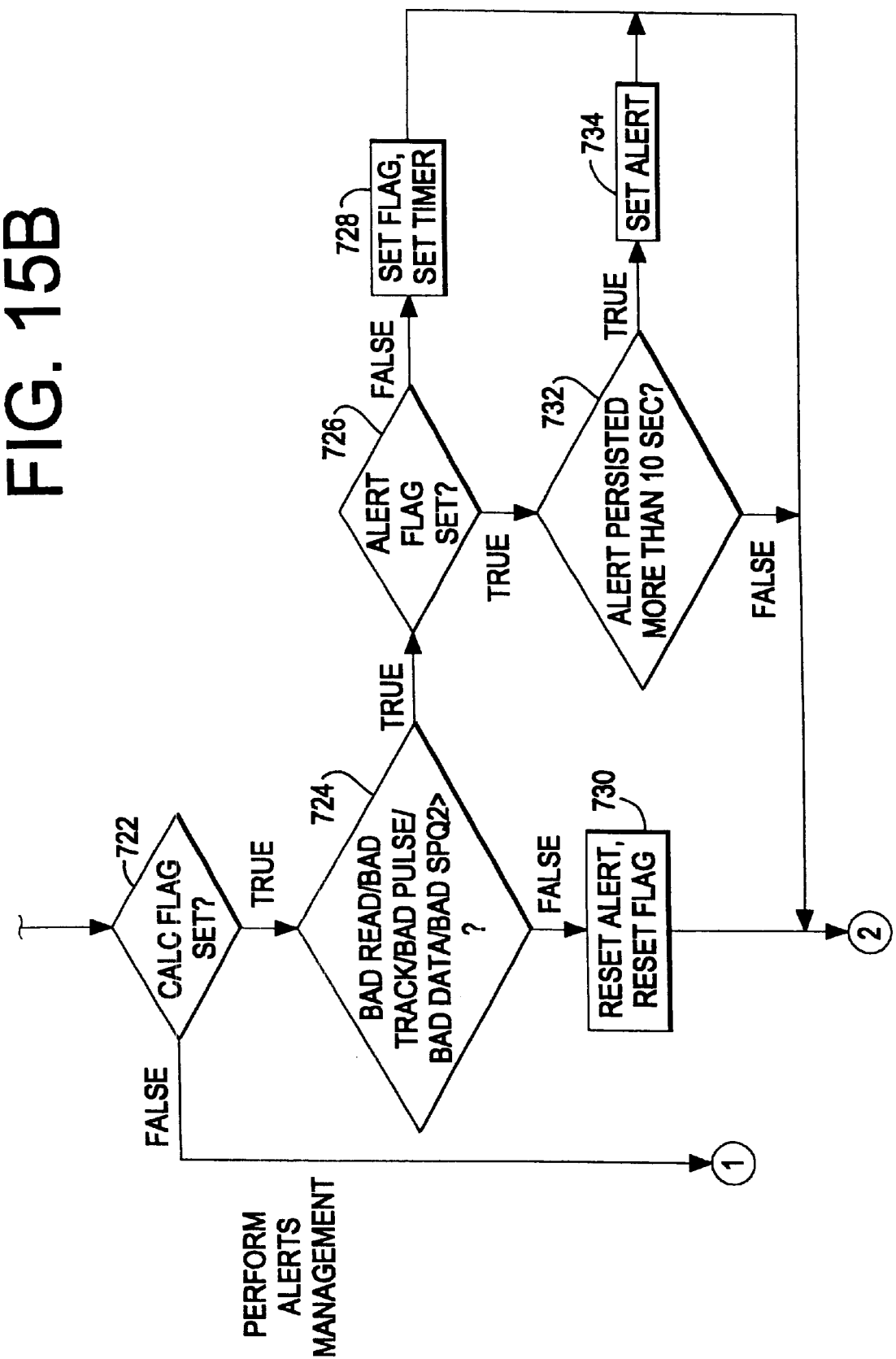
Figure 15D:
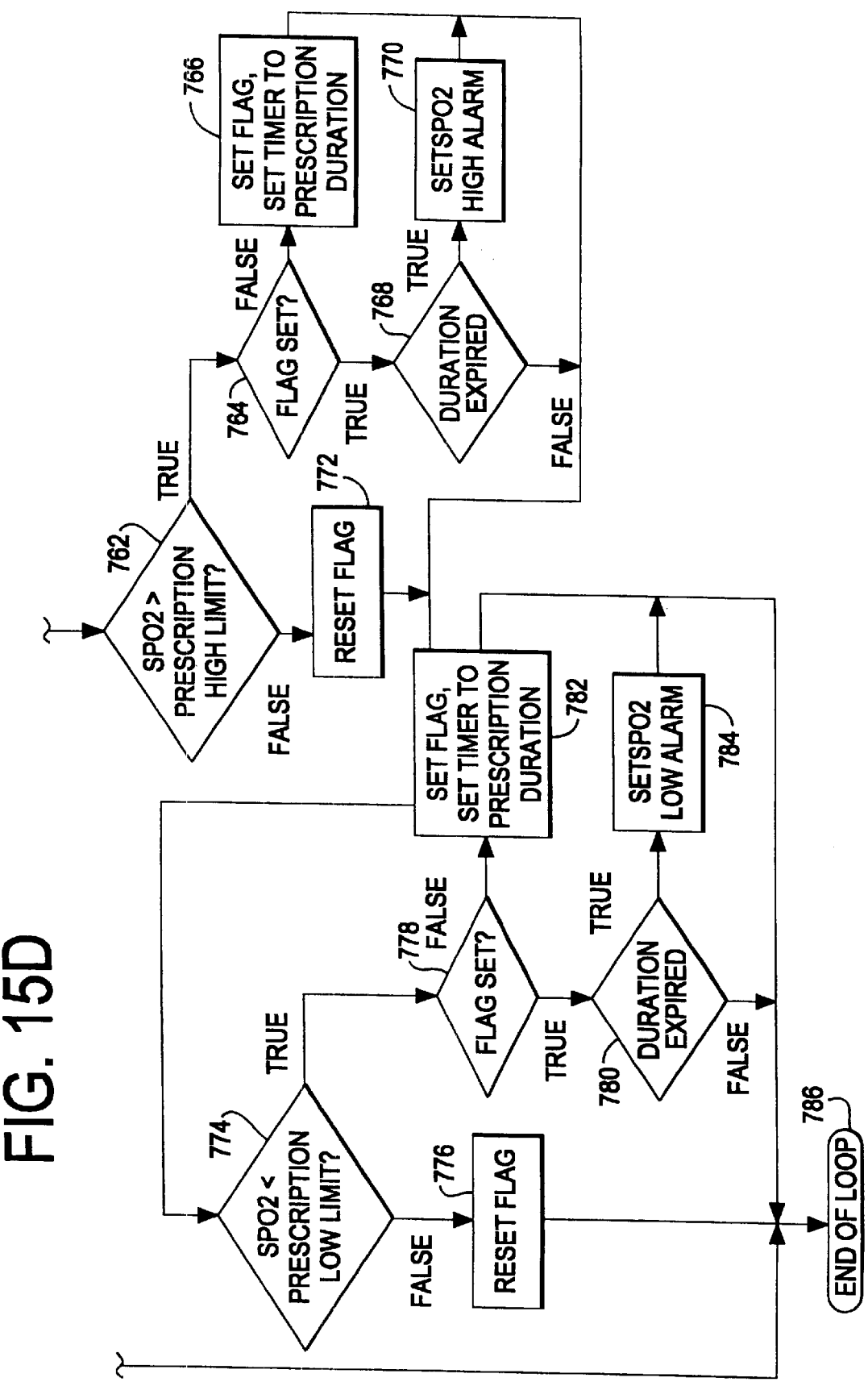
Figure 16A:
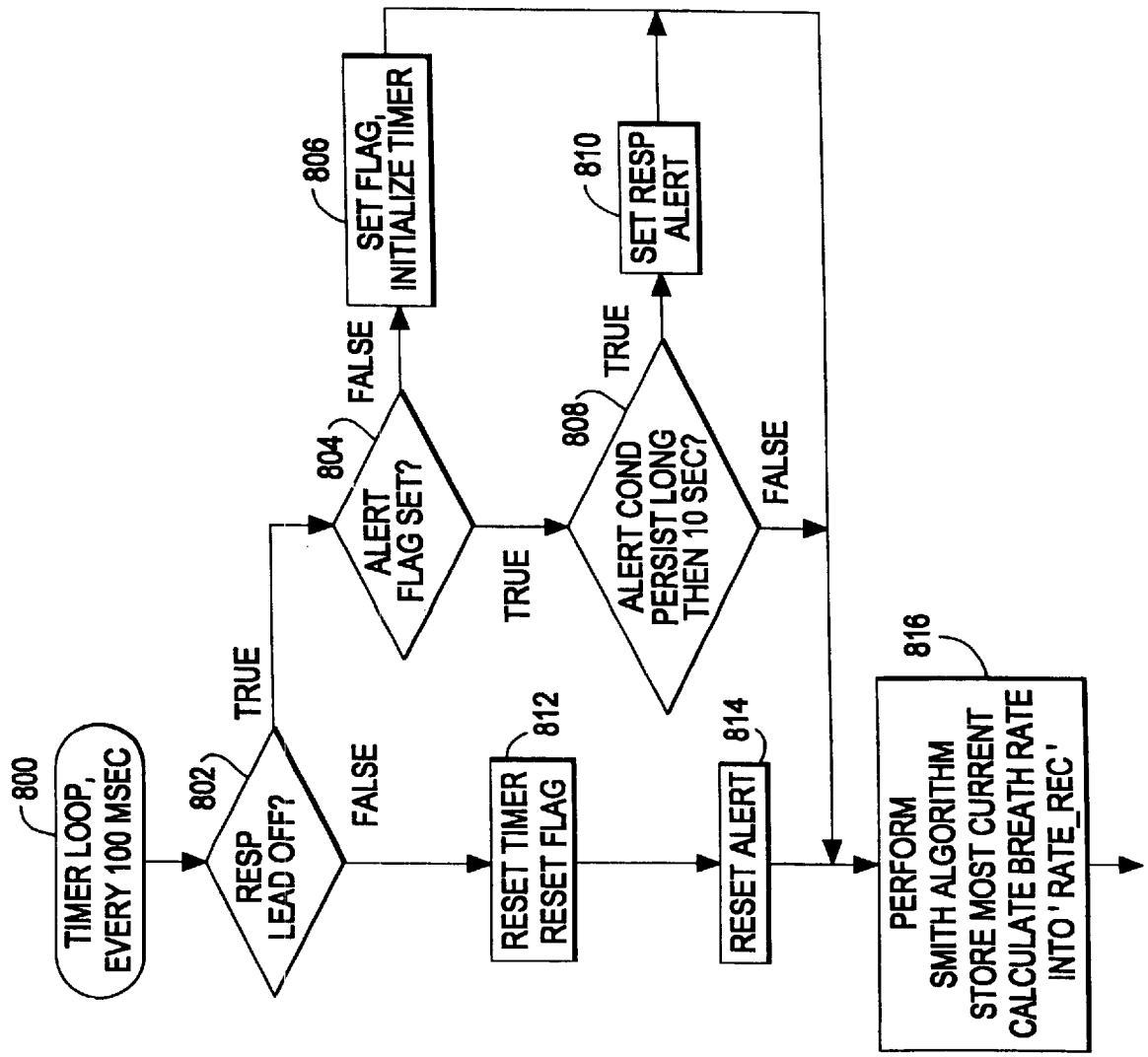
Figure 16C:
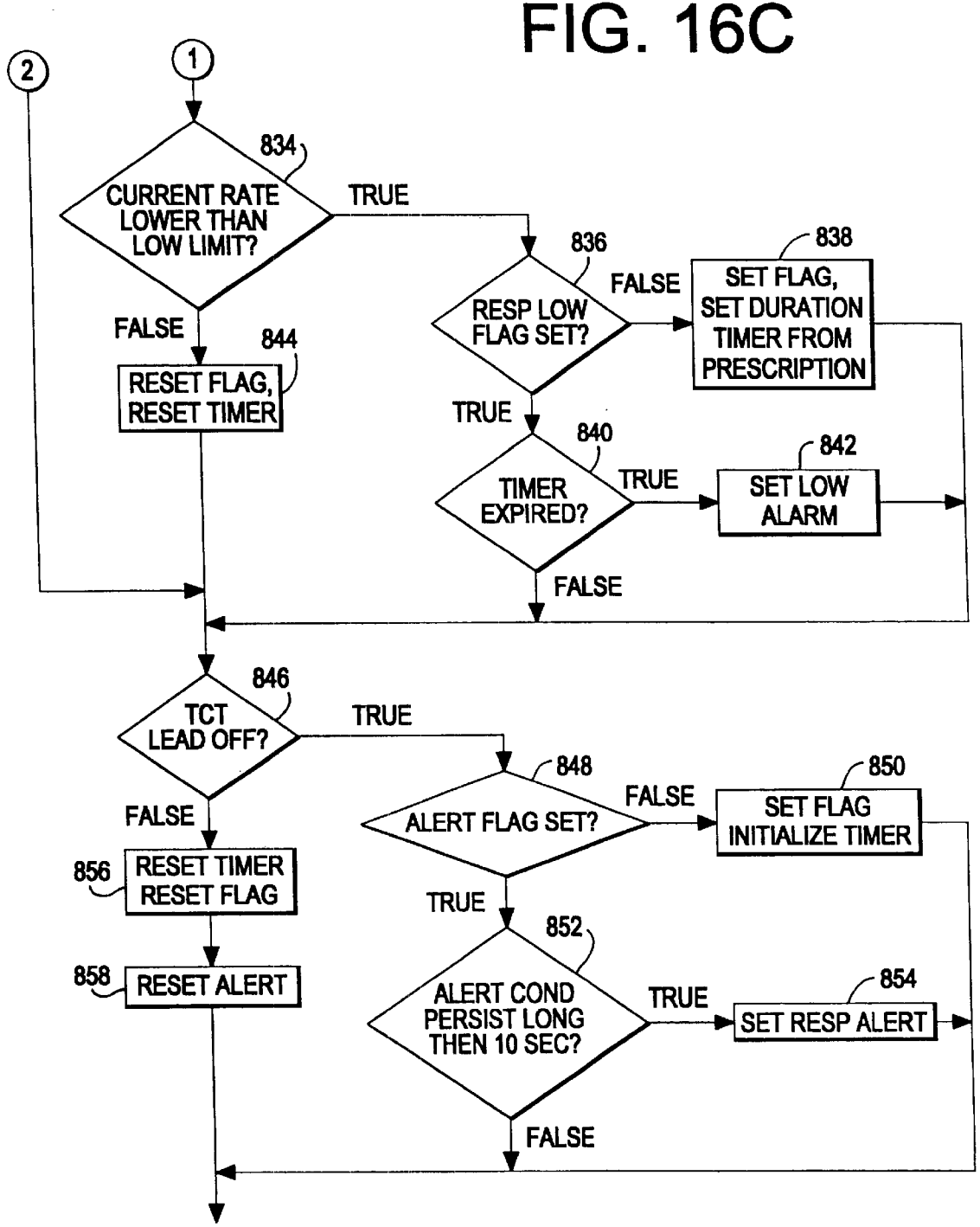
Figure 16D:
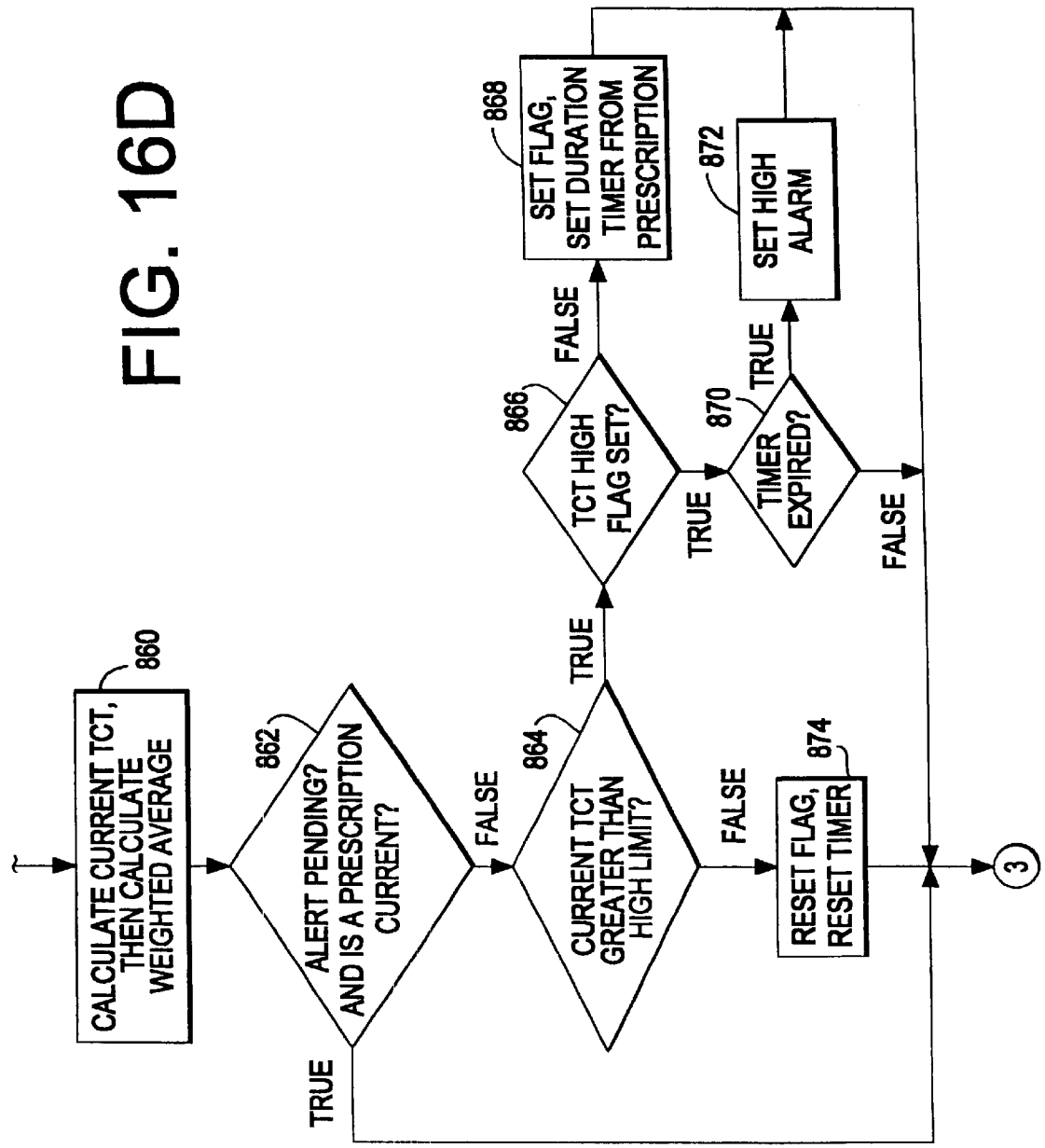
Figure 16E:
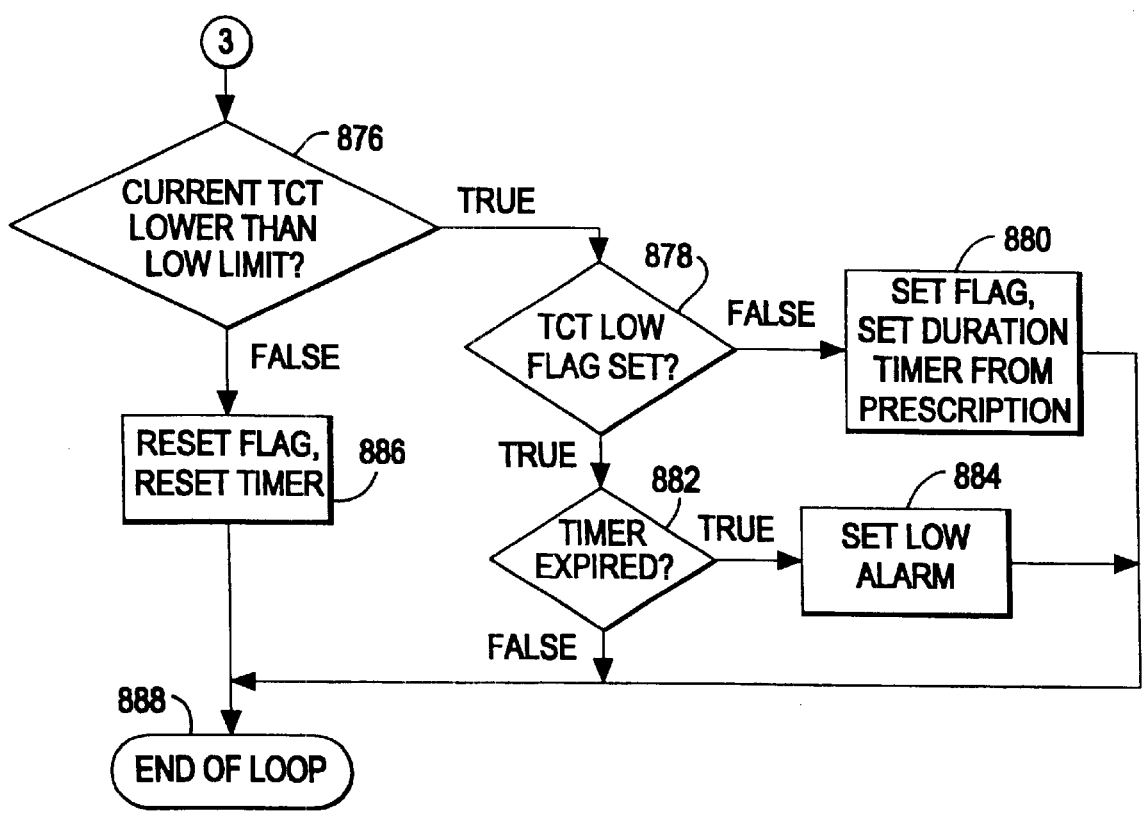
Figure 17A:
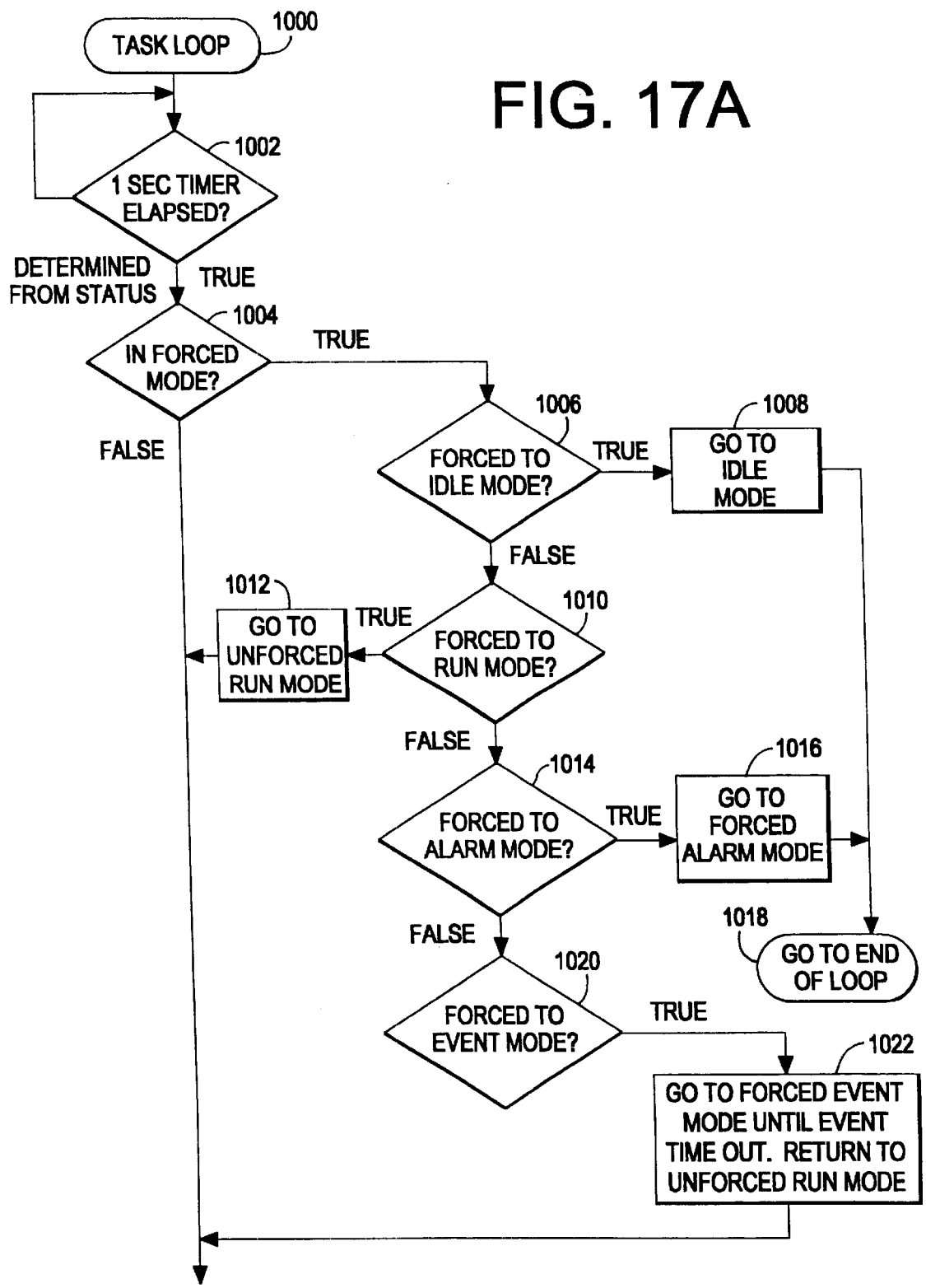
FIGS. 17A–17F are a flow chart of the control task flow in the ambulatory patient monitor.
Figure 17B:
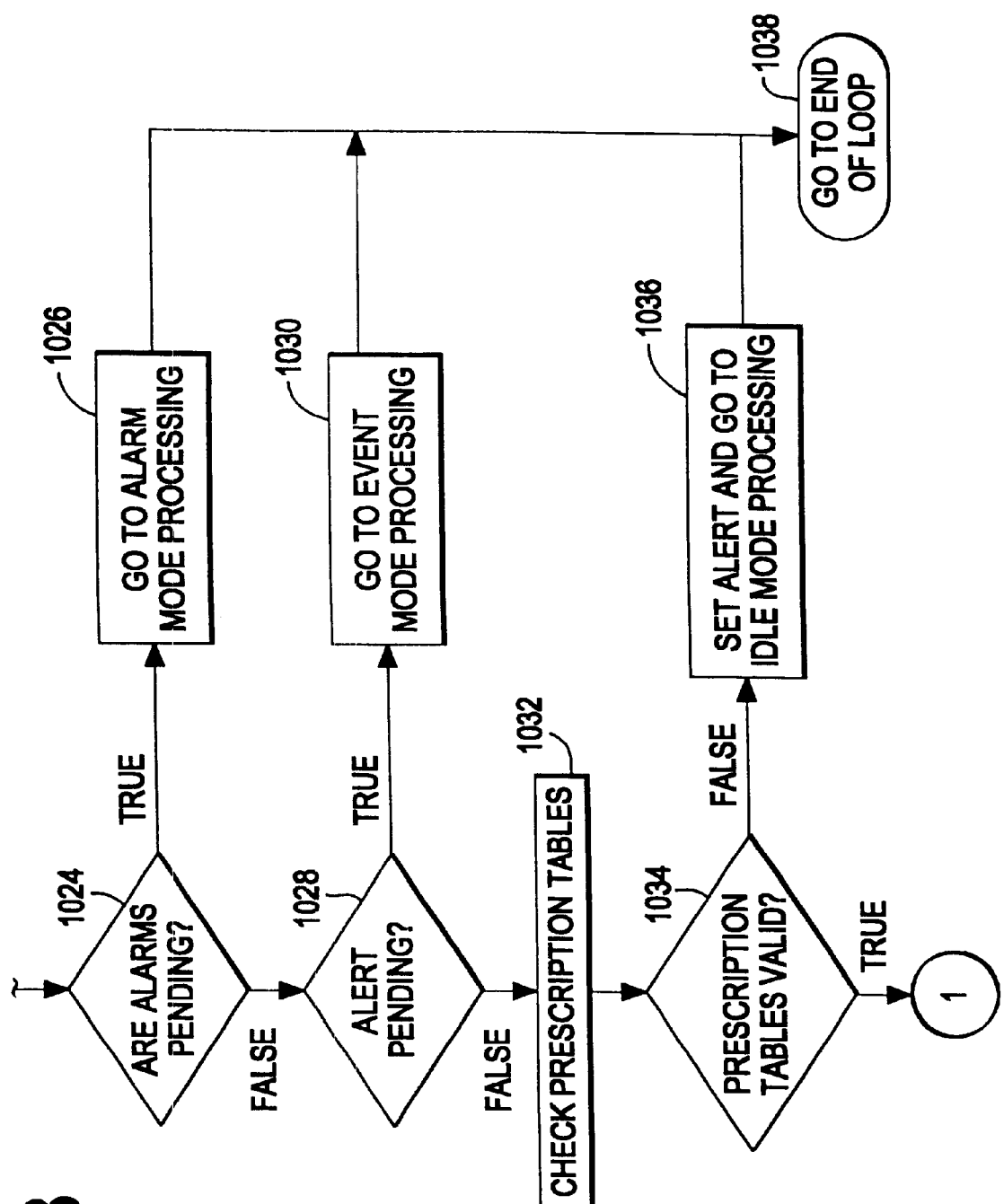
Figure 17C:
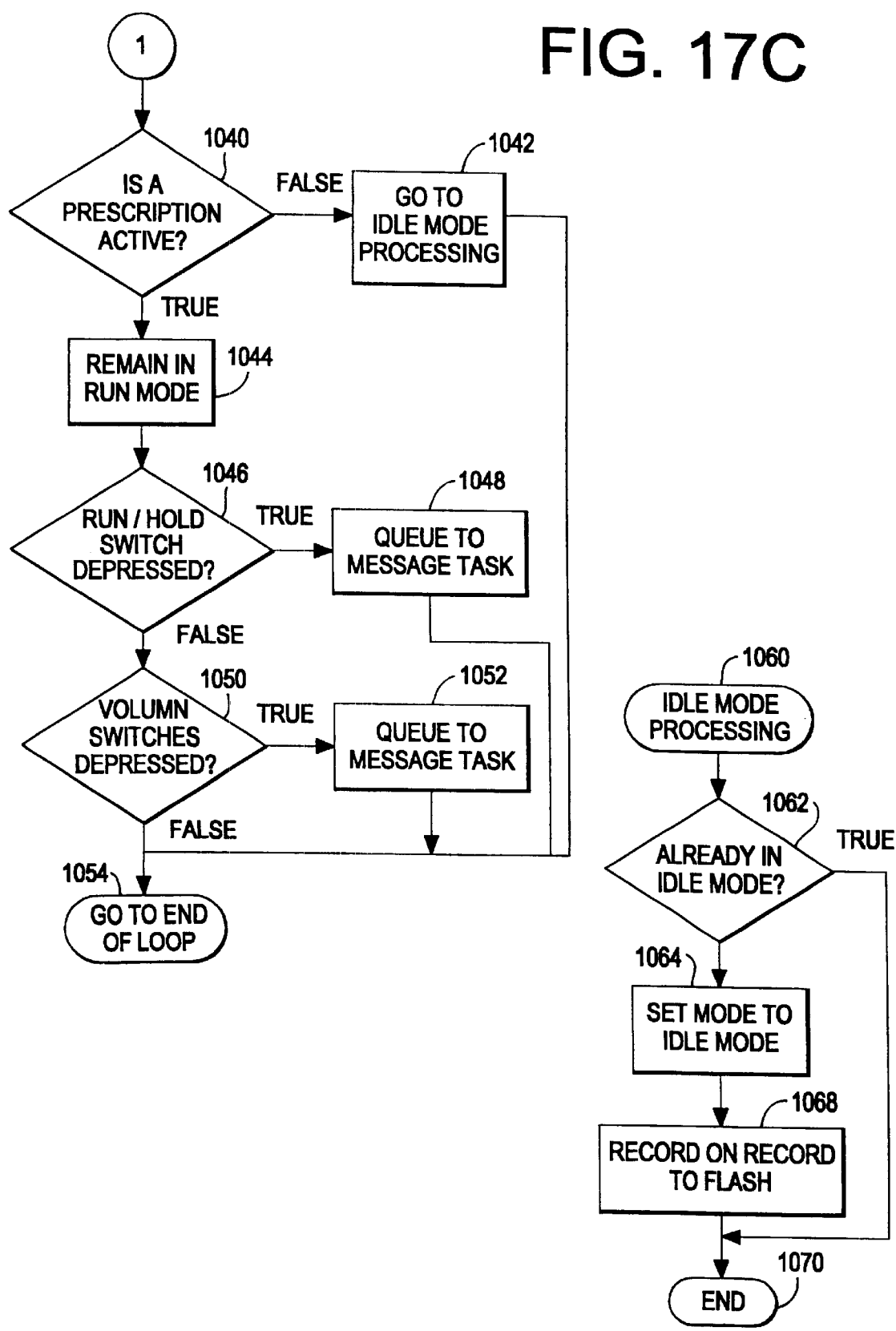
Figure 17D:
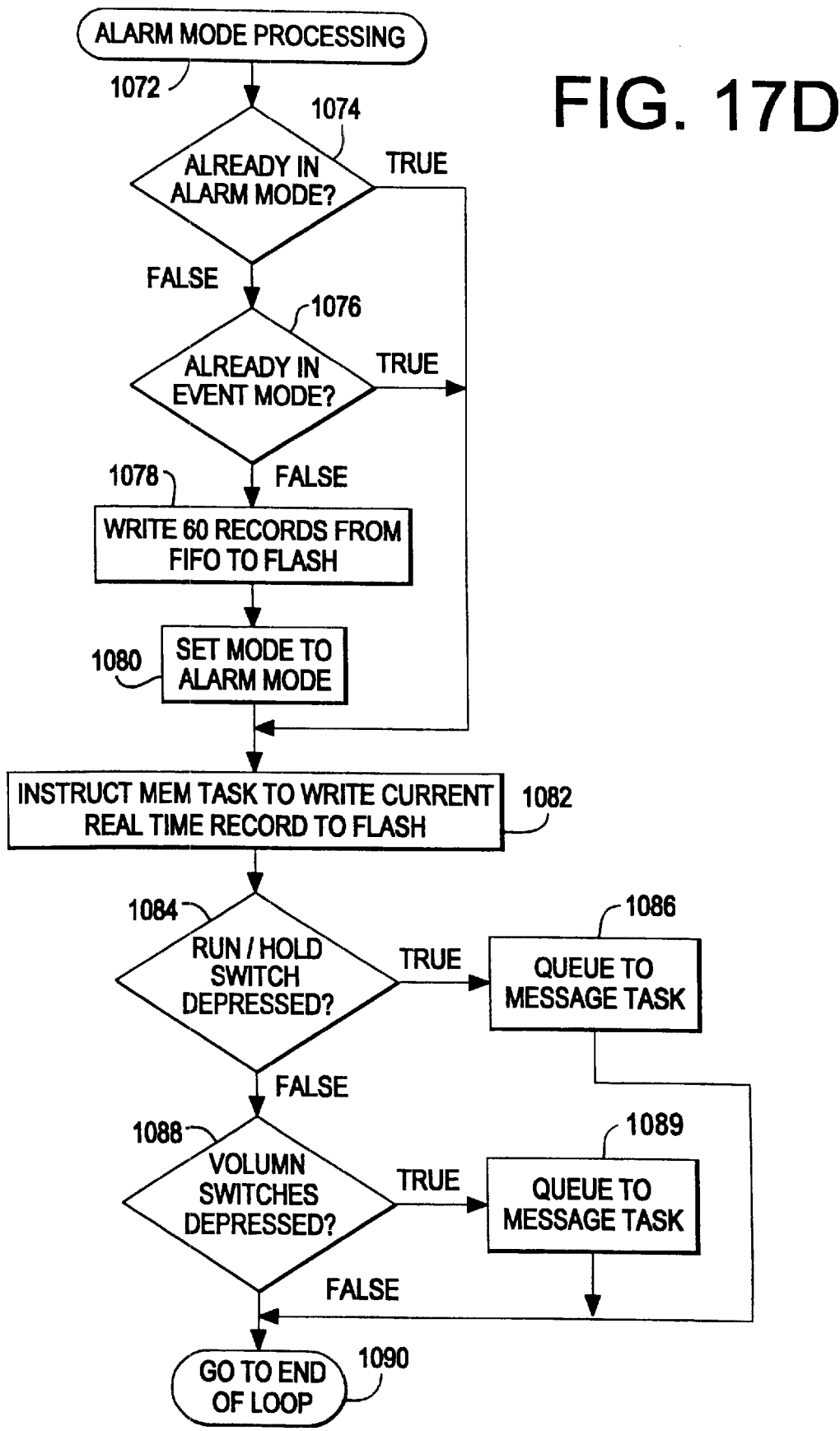
Figure 17E:
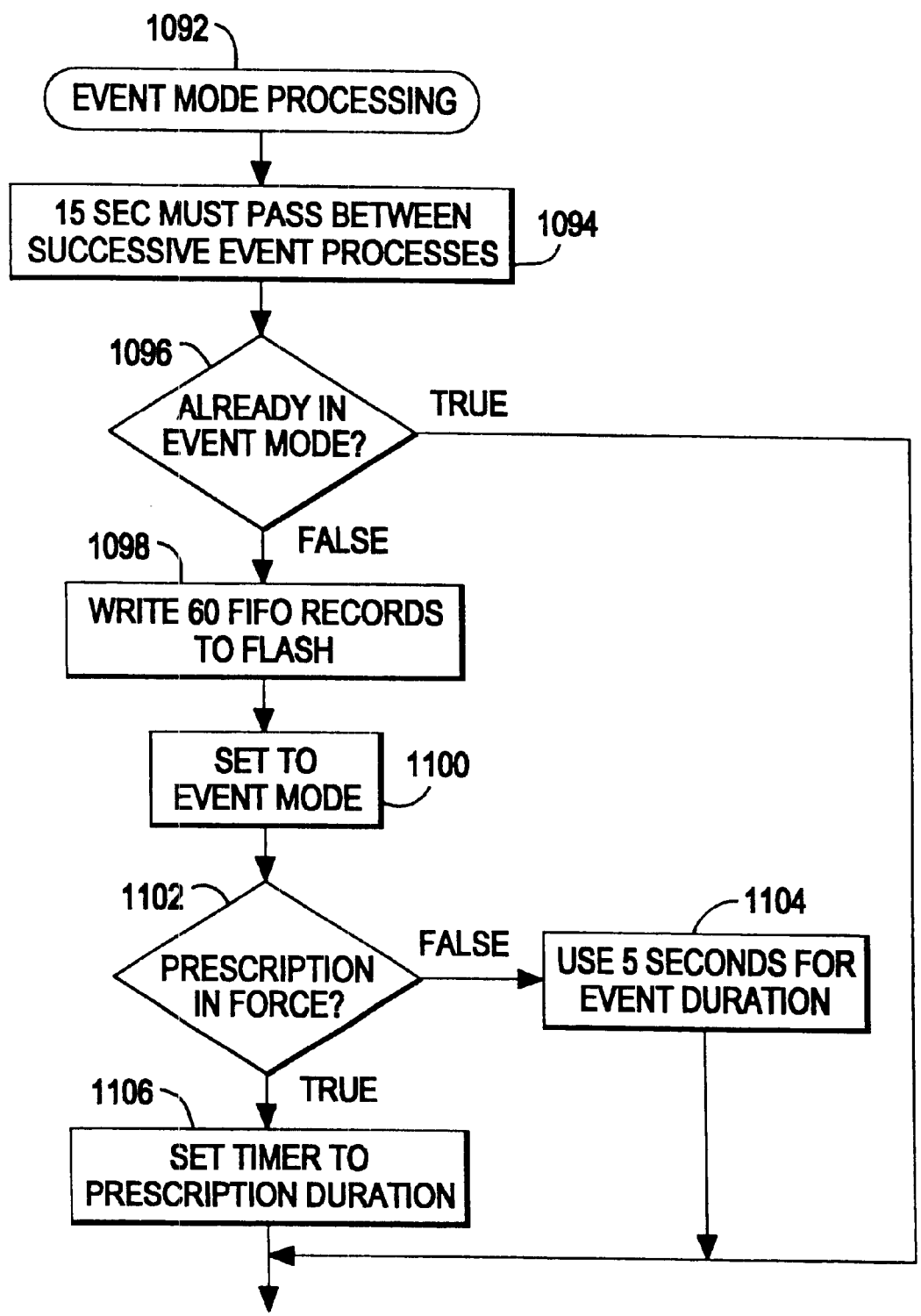
Figure 17F:
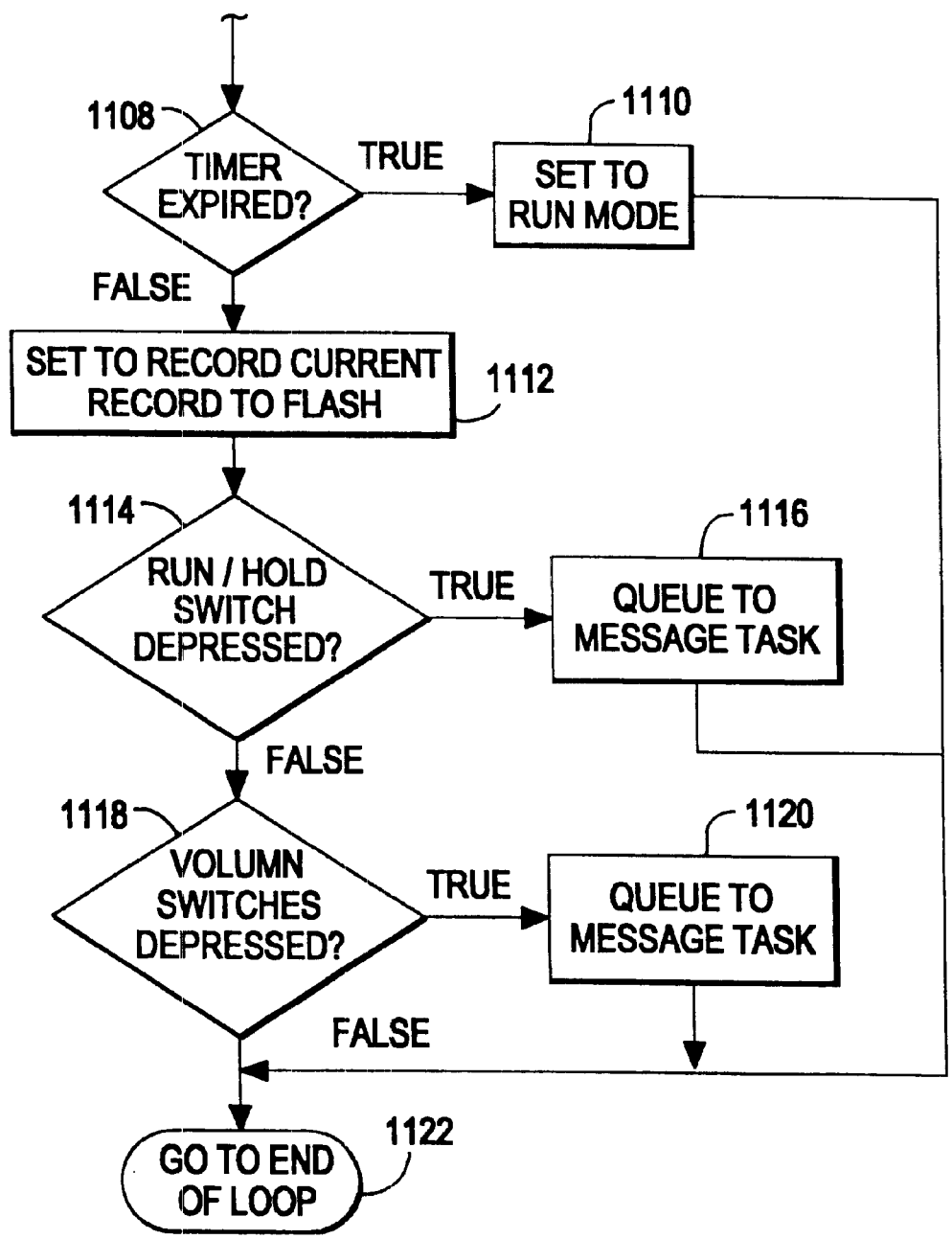

Microcontroller 201 controls the memory management tasks in accordance with a task flow routine. Referring to FIGS. 14A–14C, the microcontroller 201 begins the memory routine, which is executed every one second, at step 520. The routine checks if the buffer flag is zero at step 522 indicating the buffer is full. If true, the routine points to the double buffer 0 at step 524. If false, the routine points checks if the oximetry system is enabled at step 528. If true, the routine stores the current oximetry data in the oximetry buffer of temporary memory 223 at step 530. If not enabled, the routine stores null data in the oximetry buffer at step 532. Next the routine checks if the core temperature buffer in memory 223 at step 536. If false, the routine stores null data for the core temperature at step 538.

Next the routine checks if the respiratory module is enabled at step 540. If true, the routine stores the current respiratory data in the respiratory buffer of memory 223 at step 542. If not, the routine stores null data in the respiratory buffer at step 544. In step 546 the routine gets the current time from the real time clock 221 and stores it in memory 223.

At step 548 the routine checks if the ECG leads are properly attached. If not, the routine sets a timer at step 550. The routine checks if the timer has expired at step 552. If the timer has expired, the routine sets the ECG alert at step 556. If the timer has not expired, the routine continues at step 560. If the ECG leads are properly attached, the routine resets the ECG alert at step 558.

At step 560 the routine stores the current ECG gain value in the ECG status register. At step 562 the routine updates the record with the current status. At step 564 the routine sets the status to pretriggered. At step 566 the routine records the ECG record to memory 223. At step 568 the routine removes pretriggered from the status buffer.

At step 570 the routine checks if the memory 223 is full, by checking if the record flag is set. If false, the routine jumps to the end of the loop at step 588. If true, the routine resets the record flag at step 572. At step 574 the routine writes the records from memory 223 to flash memory 222. At step 576 the routine moves indexes. At step 578 the routine checks the value of the flash memory index. If the index is indicated as full, the routine sets the memory full alert at step 580. If the index indicates the memory is not full, the routine resets the memory full alert at step 582. At step 584 the routine checks if the memory is within a fixed distance of being full. If true, the routine initiates a block erase of the size of the fixed distance at step 586. If not, the routine ends at step 588.

Instructions

Preferably, two Instruction Tables are stored in the ambulatory patient monitor 20, called Instruction Table 1 and 2. Each Instruction Table contains parameters as shown below. If an Instruction Table is in effect, the parameters of the table are used to govern the operations of the ambulatory patient monitor 20. Each Instruction Table includes a START/STOP entry that determines what segment of a 24-hour period that the Instruction Table is in effect. Instruction Tables can be set and read back by command via the data link. An Instruction Table can be disabled by setting its START/STOP time parameters with identical values. Instruction Tables are maintained in non-volatile EEPROM 224 in ambulatory patient monitor 20.

Each Instruction Table includes check bytes that are generated by the host system as Instructions are transmitted to the ambulatory patient monitor 20 via data link. The ambulatory patient monitor 20 routinely checks the validity of the Instruction Tables using these check types. If an Instruction Table is not valid, the system will set an Alert and go to Idle Mode.

Start/Stop Time for the Instruction Tables is expressed in hours past midnight. Examples:

Start=0/Stop=6==>prescription is active from midnight to 6AM;

Start=13/Stop=2==>prescription is active from 1PM to 2AM;

Start=2/Stop=2==>prescription is inactive.

Event Time Duration (range 0 to 100 sec)—when the event button is depressed, the previous 60 seconds of data are recorded, followed by records over the event time duration.

| INSTRUCTION TABLE | |
|---|---|
| OXIMETRY | RANGE |
| Oximetry Measurement System Enable/Disable | On/Off |
| $S_pO_2$ Alarms Enable/Disable | On/Off |
| $S_pO_2$ Time Between Recordings | 0–1000 seconds |
| $S_pO_2$ Recording Duration | 0–1000 seconds |
| Low $S_pO_2$ Limit | 50–100% |
| High $S_pO_2$ Limit (High must be greater than low) | 50–100% |
| Maximum out of limit of $S_pO_2$ duration | 0–100 seconds |
| Heart Rate Alarms Enable/Disable | On/Off |
| Heart Rate Time between Recordings | 0–1000 seconds |
| Heart Rate Recording Duration | 0–1000 seconds |
| Low Heart Rate Limit | 30–250 beats/min. |
| High Heart Rate Limit (must be greater than low) | 30–250 beats/min. |
| Maximum out of limit of heart rate duration | 0–100 seconds |
| TEMPERATURE | |
| Temperature Measurement System enable/disable | On/Off |
| Temperature alarms enable/disable | On/Off |
| Time between Temp. recordings | 0–1000 seconds |
| Recording duration | 0–1000 seconds |
| Low Temp limit | 90–106 degrees F. |
| High Temp limit | 90–106 degrees F. |
| Maximum out of limit Temp duration | 0–100 seconds |
| RESPIRATORY | |
| Respiratory Measurement System Enable/disable | On/Off |
| Respiratory alarms enable/disable | On/Off |
| Time between respiratory rate recordings | 0–1000 seconds |
| Recording duration | 0–1000 seconds |
| Low Rate limit | 3–45 breaths/min |
| High Rate limit | 3–45 breaths/min |
| Maximum out of limit duration | 0–100 seconds |
| ECG | |
| ECG Measurement system enable/disable | On/Off |
| Time between ECG recording sessions | 0–1000 seconds |
| Duration of ECG recording session | 0–1000 seconds |

A Time Between Recording of 0 will cause the measurement set to be recorded "real-time," or once per second. If Low or High Limit Value is set to 256, then the physiological alarm associated with that parameter is disabled. An Instruction must be active if recorded records are to include measurement data and if alarms are to be armed. Otherwise only Null records are recorded. Null records contain null data with valid RTC data and status. The Alarms enable/disable parameter will disable all alarms of the system when disabled. This does not impact ALERTS. ALERTS pertaining to a measurement are always armed, unless the measurement system is disabled.

During an ALARM, the corresponding out-of-range value will be displayed. Pressing the REVIEW key will cause the display to alternate between the out-of-range alarm value and the corresponding alarm limit with each press.

As stated above, a preferred embodiment of the patient home management system 10 includes an ambulatory patient monitor 20 connected to four sensors: oximetry (arterial pulse oxygen saturation ($S_pO_2$) and heart rate (pulse rate)), electrocardiogram, temperature and respiration rate. The ambulatory patient monitor 20 interfaces with the communications unit 30 which communicates with the caregiver at a remote location. The caregiver uses the remote control software 410 to program, monitor and retrieve data from the ambulatory patient monitor 20 and the communications unit 30. ALARMS may be set by the caregiver using the remote control software 410 to establish INSTRUCTIONS and are transferred to the ambulatory patient monitor 20 by the communications unit 30. Once programmed, the ALARMS may only be changed by the caregiver using the remote control software 410. The INSTRUCTIONS are then sent to the communications unit 30 for downloading to the ambulatory patient monitor 20. ALARMS are locked until reset by the caregiver.

ALERT test limits are stored in both the ambulatory patient monitor 20 and the communications unit 30 and cannot be changed by commands from the communications unit 30. ALERTS are reset and clear automatically when the problem causing the ALERT is cleared.

When an ALARM is triggered, the power ON/OFF key 508 of the ambulatory patient monitor keyboard is disabled until the ALARM data is transferred to the caregiver via the communications unit 30 and a release command is received from the caregiver.

The ambulatory patient monitor 20 can operate from its own source of power, i.e. a battery, such as when it is being worn by a patient. The ambulatory patient monitor 20 can also operate from an external source of power from the communications unit 30 when it is coupled to the communications unit 30.

The ambulatory patient monitor 20 preferably operates from two batteries: a primary battery and a backup battery. If primary battery power is removed while the ambulatory patient monitor 20 is in ALARM mode, a Back-up Audio Tone is enabled (powered by the second battery) and remains ON until the primary battery is replaced. If the RUN mode is then activated, the ALARM mode will continue. The Back-up Audio Tone is also enabled by a watchdog timer reset or an abnormal primary power shut-down. Batteries should be replaced only after the ambulatory patient monitor 20 is connected to an alternate power supply through the communications unit 30.

When batteries are low, the ambulatory patient monitor 20 can be connected to the communications unit 30 (which operates offline current) while the batteries are being replaced. This enables the patient to be continuously monitored without having to turn otf the ambulatory patient monitor 20.

Figure 18A:
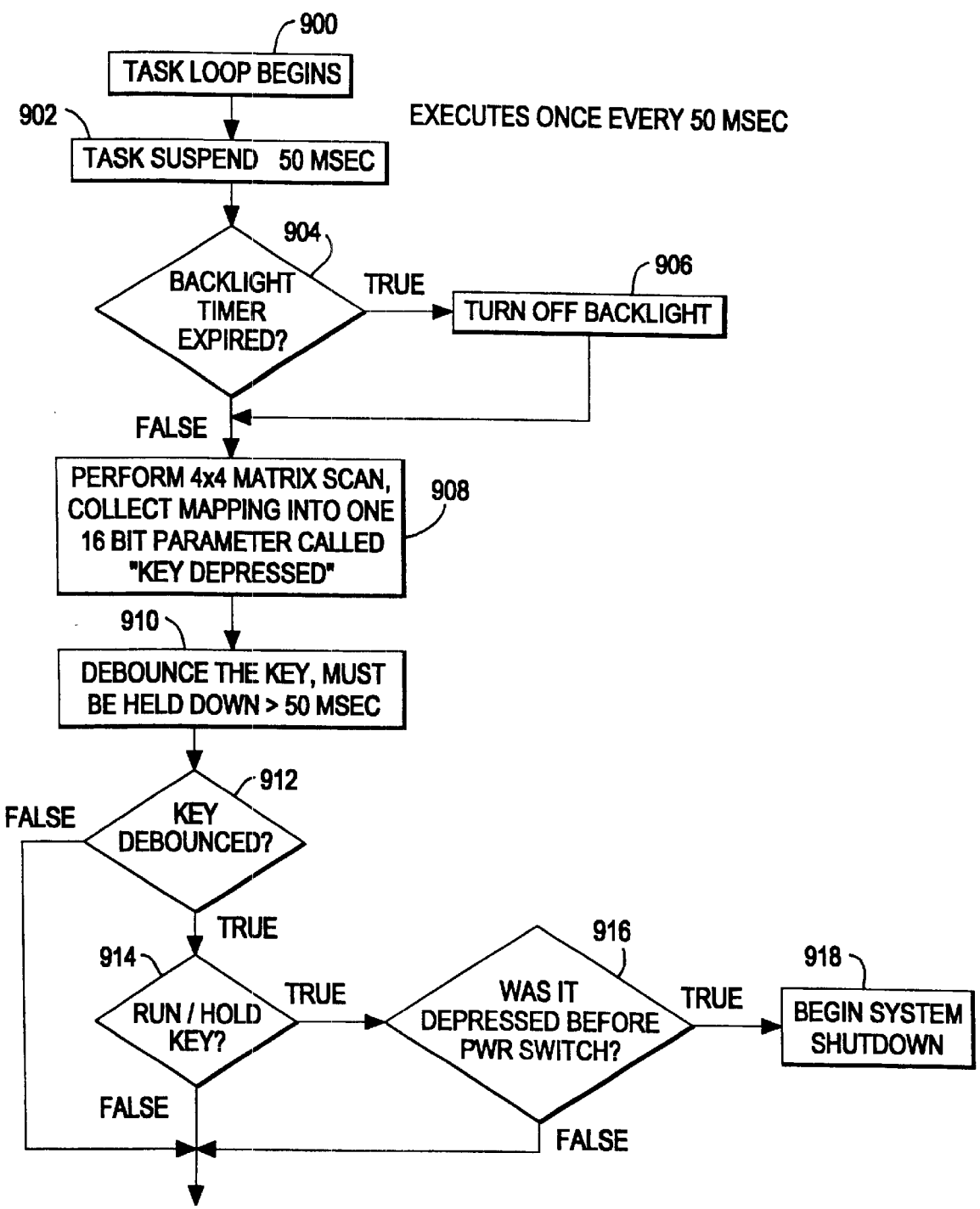
FIGS. 18A–B are a flow chart of the key pad and power management task in the ambulatory patient monitor.
Figure 18B:
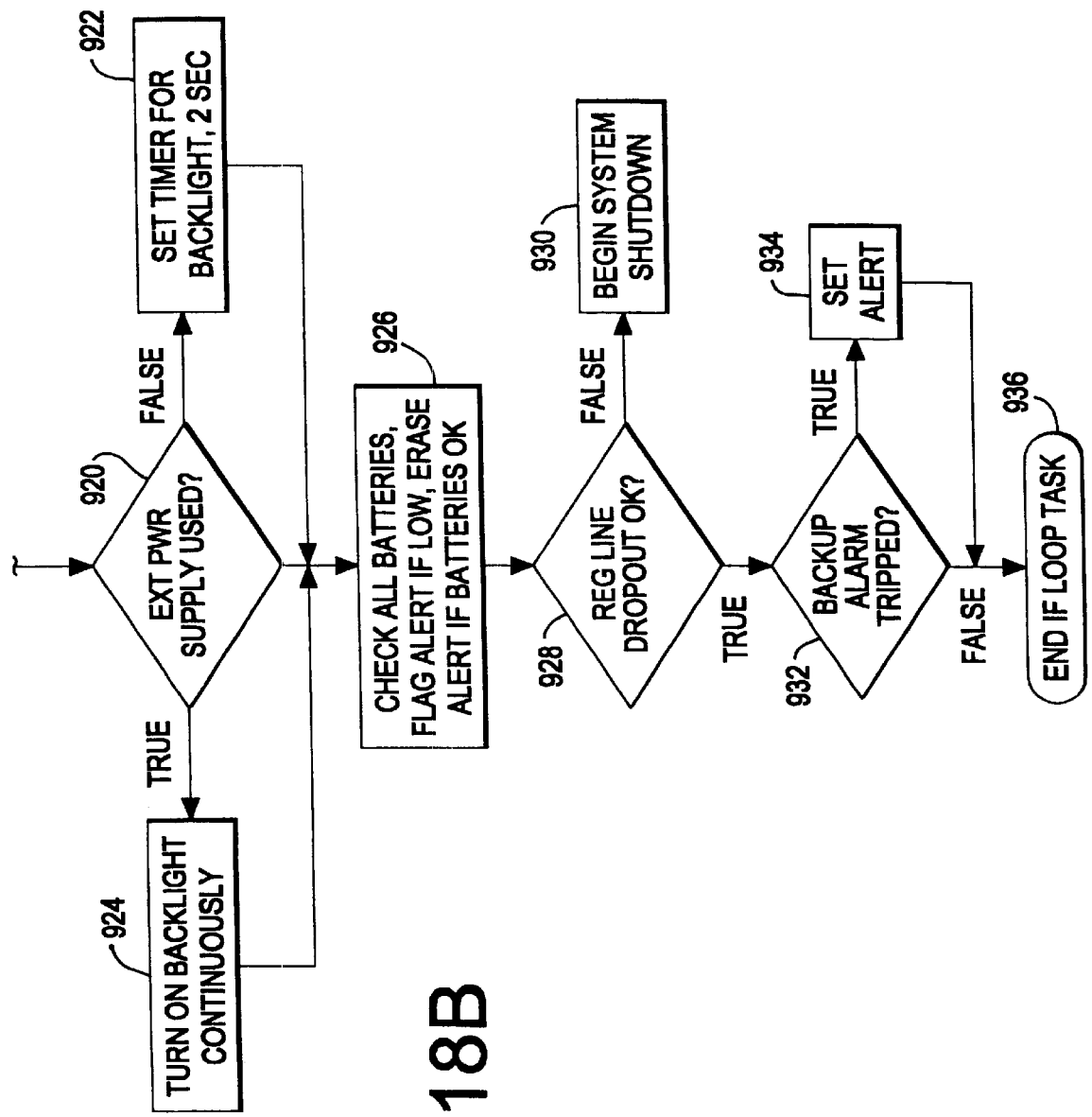

Microcontroller 201 drives the keypad and power management operation in accordance with a task flow routine. Referring to FIG. 18 the microcontroller 201 begins the routine at step 900. This loop executes every 50 milliseconds. At step 902 the routine suspends the 50 msec timer. At step 904 the routine checks if the backlight timer has expired. If true, the routine turns off the backlight at step 906. If not the routine performs a matrix scan to determine if any key has been depressed at step 908. At step 910 the routine debounces any key held down for greater than 50 msec.

At step 912 the routine checks if the key has been debounced. If not, the routine continues at step 920. If it has, the routine checks if the run/hold key is depressed at step 914. If not, the routine continues at step 920. If the run/hold key has been depressed, the routine checks if it was depressed before the power switch at step 916. If true, the routine powers down the system at step 918. If false, the routine continues at step 920.

At step 920 the routine checks if external power is being used. If not, the routine sets the backlight timer for two seconds at step 922. If true, the routine sets the backlight time for continuous at step 924. At step 926 the routine checks the batteries and issues alerts if one or more need changing. At step 928 the routine checks if line dropout is okay. If not, the routinebegins system shutdown at block 930. If true, the routine checks if the backup alarm has been tripped at step 932. If true, the routine sets the alert at step 934. If false, the routine ends at step 936.

Modes and Operation of Ambulatory Patient Monitor

The microcontroller 201 controls all of the various subsystems of the ambulatory patient monitor 20 including audio alarms, front panel switches, LCD status display, solid-state memory watchdog timers, power supply regulators, and a two-way serial interface.

Data Storage: Data is stored, preferably, for 24 hours and then downloaded by the use of a direct cable connection to the communications unit 30; however, the ambulatory patient monitor 20 preferably includes the capacity to store patient data for a week under the no-alarm conditions described below. The following data rates for sampling of the various sensor data are preferred:

ECG—15 seconds of data every 5 minutes for most recent 24 hours;
Pulse Oximetry and Pulse Rate—15 samples per minute for most recent 24 hours;
Temperature—1 sample per minute for most recent 24 hours;
Time/Date—1 sample per minute for most recent 24 hours;
System Error Alarms—1 sample per alarm.

"Real-Time" Data Transfer Rate: Data is preferably transferred to the communications unit 30 preferably in "real-time" at the following data rates:

ECG—240 samples per second;
Pulse Oximetry and Pulse Rate—1 sample per second;
Temperature—1 sample per 60 seconds;
Time/Date—1 sample per 60 seconds.

Speech Synthesizer: A speech synthesizer may be included which drives a speaker within the ambulatory patient monitor 20. The recorded vocabulary may be used to provide Instructions to the user with each ALARM or ALERT. The volume of the voice output may be adjustable by the user.

Disposables: Preferably the following disposables will be used with the system 10: Pulse oximetry sensor finger cover;

ECG electrodes; Batteries; Nasal cannula respiration sensor for day and night use; Sensor Placement Template; Tape strips to secure wires, temperature sensor cover.

The ambulatory patient monitor 20 has four modes of operation. The monitor 20 can go from one mode to another. Changing modes will cause at least one record to be recorded in main memory 224, such that an audit of the change (shown in internal status) can be maintained. RUN MODE (or NORMAL MODE) is the default mode of the ambulatory patient monitor 20. It is invoked on power-up, and it can be invoked via data link command. In this mode, the ambulatory patient monitor 20 continually monitors ALARMS and ALERTS. It records data records to the Flash Memory 222 according to an Instruction Table. Even if all measurement systems are disabled, or if Instructions are disabled, the ambulatory patient monitor 20 will record null records to the FIFO memory.

ALARM MODE begins when an alarm has tripped. The previous 60 seconds (60 records) of data from the FIFO memory 223 are stored to Flash Memory 222. Then a realtime record is stored to both temporary 223 and to FLASH memory 222 every second. This mode will continue until it is commanded to end via a data link command, or the ambulatory patient monitor 20 is powered down.

EVENT MODE is similar to Alarm Mode, except that a finite number of records are recorded. The Event Key 510 is located on the ambulatory patient monitor 20 front panel, and it can be invoked by the patient while the unit is in RUN MODE. Event Key activation will cause the ambulatory patient monitor 20 to copy the previous 60 seconds of record from Temporary memory 223 to Flash Memory 222. Then real-time records will be recorded to temporary memory 223 and to flash memory 222 at the rate of 1 record per second for a specific length of time as determined by the Instruction Table. Once this time is reached, the unit will return to Normal Mode operation unless alarms have been triggered while in Event Mode. If so then the ambulatory patient monitor 20 goes to Alarm Mode. If the patient invokes the Event Key before the time limit expires, then the limit timer is reloaded while the unit continues in Event Mode. The user could continually extend Event Mode operation by continually depressing the Event Key.

In IDLE MODE no data recording or data acquisition is performed. The monitor 20 will respond to data link commands.

In Run Mode, Alarm Mode, and Event Mode all of the measurement systems will continuously acquire sensor data and process their respective data unless a specific data link command is issued that directs the ambulatory patient monitor 20 to go to Idle Mode. There are other methods to disable certain measurement systems, such as from specific Instructions.

Microcontroller 201 drives the monitor 20 in accordance with a control task flow routine. Referring to FIGS. 17A–17F, the microcontroller 201 begins the routine at step 1000. At step 1002 the routine loops until one second has passed. At step 1004 the routine checks if the unit is in forced mode. If true, at step 1006 the routine checks if the monitor 20 is being forced to idle mode. If true, the routine puts the monitor 20 in idle mode at step 1008 and continues to the end of the loop at step 1018. If not forced into idle mode, the routine checks if the monitor 20 is being forced into run mode at step 1010. If true, the routine puts the monitor 20 in unforced run mode at step 1012 and continues to step 1024. If not in forced run mode, the routine checks if the monitor 20 is being forced into alarm mode at step 1014. If true, the routine puts the monitor 20 into forced alarm mode at step 1016 and then continues to the end of the loop at step 1018. If not in forced alarm mode, the routine checks if the monitor 20 is being forced to event mode at step 1020. If true, the routine puts the monitor 20 in forced event mode until the event time out and then continues to unforced run mode.

At step 1024 the routine checks if any alarms are pending. If yes, the routine branches to the alarm mode processing subroutine at step 1026 and then to the end of the loop at step 1038. If no alarms are pending, the routine checks if any alerts are pending at step 1028. If yes, the routine goes to event mode processing at step 1030 and then to the end of the loop at step 1038. If no alerts are pending, the routine fetches the values in the Instruction Tables at step 1032. At step 1034, the routine checks if the values are valid. If not valid, the routine sets an alert and goes to idle mode processing at step 1036 and then to the end of the loop at step 1038.

If the Instruction values are valid, the routine checks if the Instruction is active at step 1040. If not, the routine goes to idle mode processing at step 1042 and then to the end of the loop at step 1054. If the values are valid, the routine remains in run mode at step 1044. At step 1046 the routine checks if the run/hold switch is depressed. If yes, the routine queues to message task at step 1048, then goes to the end of the loop at step 1054. If not, the routine checks if the volume switches are depressed. If yes, the routine queues to the message task at step 1052, then goes to the end of the loop at step 1054. If not, the routine goes to the end of the loop at step 1054.

When idle mode processing is called at step 1060, the routine checks if the monitor 20 is already in idle mode. If true, the subroutine ends at step 1070. If false, the routine sets the mode to idle mode at step 1064 then records the state in flash memory 222 at step 1068, then ends at step 1070.

When alarm mode processing is called at step 1072, the routine checks if the monitor 20 is already in alarm mode at step 1074. If true, the routine jumps to step 1082. If not, the routine checks if the monitor 20 is already in event mode at step 1076. If yes, the routine jumps to step 1082. If not, the routine writes 60 records from temporary memory 223 to flash memory 222 in step 1078. At step 1080 the routine sets the mode to alarm mode.

At step 1082 the routine instructs the memory task to write the current real time record to memory 222. At step 1084 the routine checks if the run/hold switch is depressed. If true, the routine queues to message task at step 1086. If not, the routine checks if volume switches are depressed at step 1088. If true, the routine queues to message task at step 1089. If not, the routine goes to the end of the loop at step 1090.

When event mode processing is called at step 1092, the routines waits 15 seconds between successive event processing at step 1094. At step 1096 the routine checks if monitor 20 is already in event mode. If true, the routine jumps to step 1108. If not, the routine writes 60 records from memory 223 to memory 222 in step 1098. At step 1100 the routine sets the mode to event mode. At step 1102 the routine checks if the current Instruction is in force. If false, the routine uses five seconds for the event duration at step 1104 and continues at step 1108. If true the routine sets the timer to the Instruction value at step 1106. At step 1108 the routine checks if the timer has expired. If yes, the routine sets the mode to run mode at step 1110. If not the routine starts recording the current record to memory 222 at step 1112. At step 1114 the routine checks if the run/hold key is depressed. If true, the routine queues to message task. If not, the routine checks if the volume switches are depressed. If true, the routine queues to message task at step 1120. If not, the routine ends at step 1122.

Figure 19A:
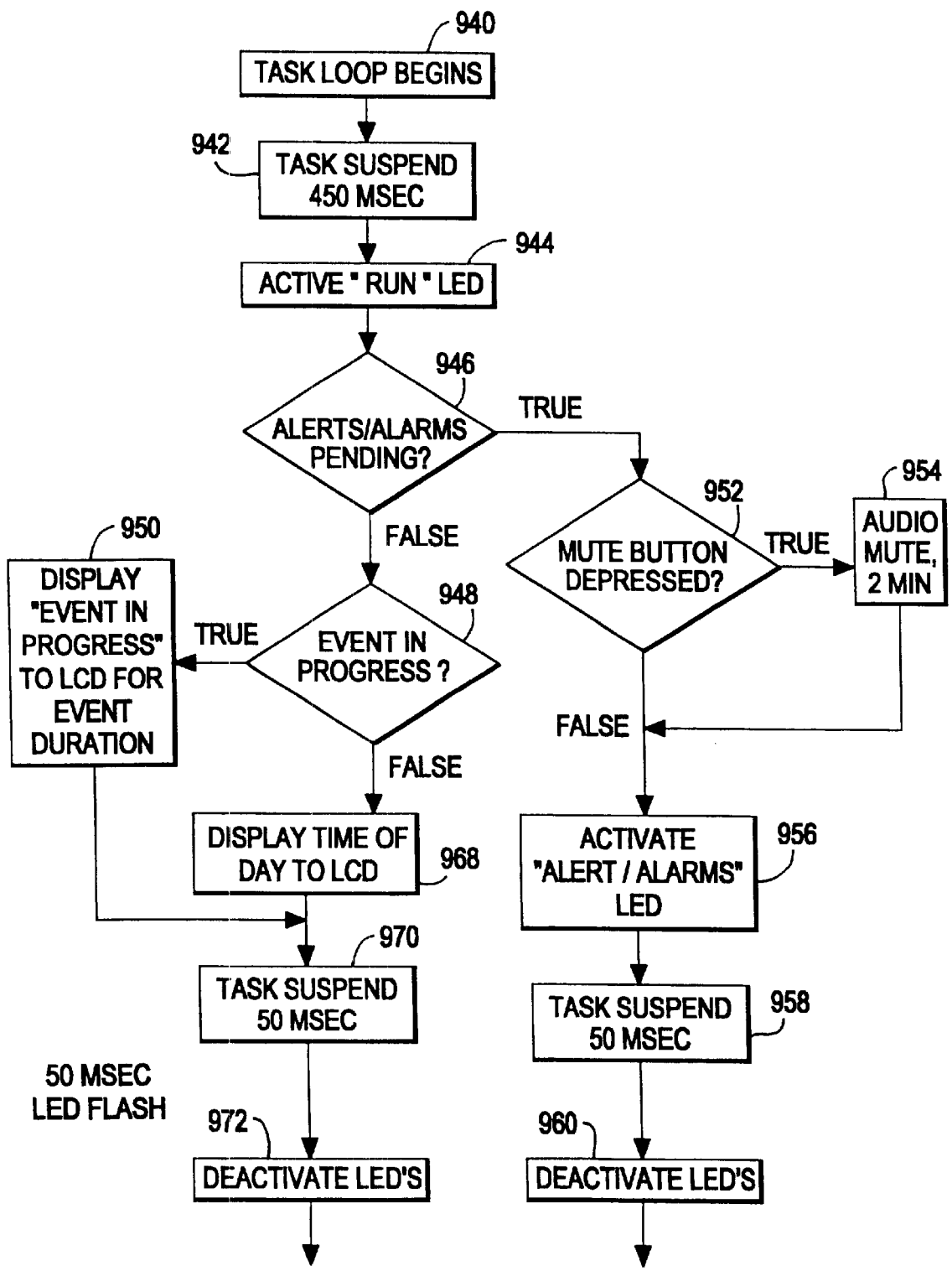
FIGS. 19A–B are a flow chart of the front panel output/ messaging task in the ambulatory patient monitor.
Figure 19B:
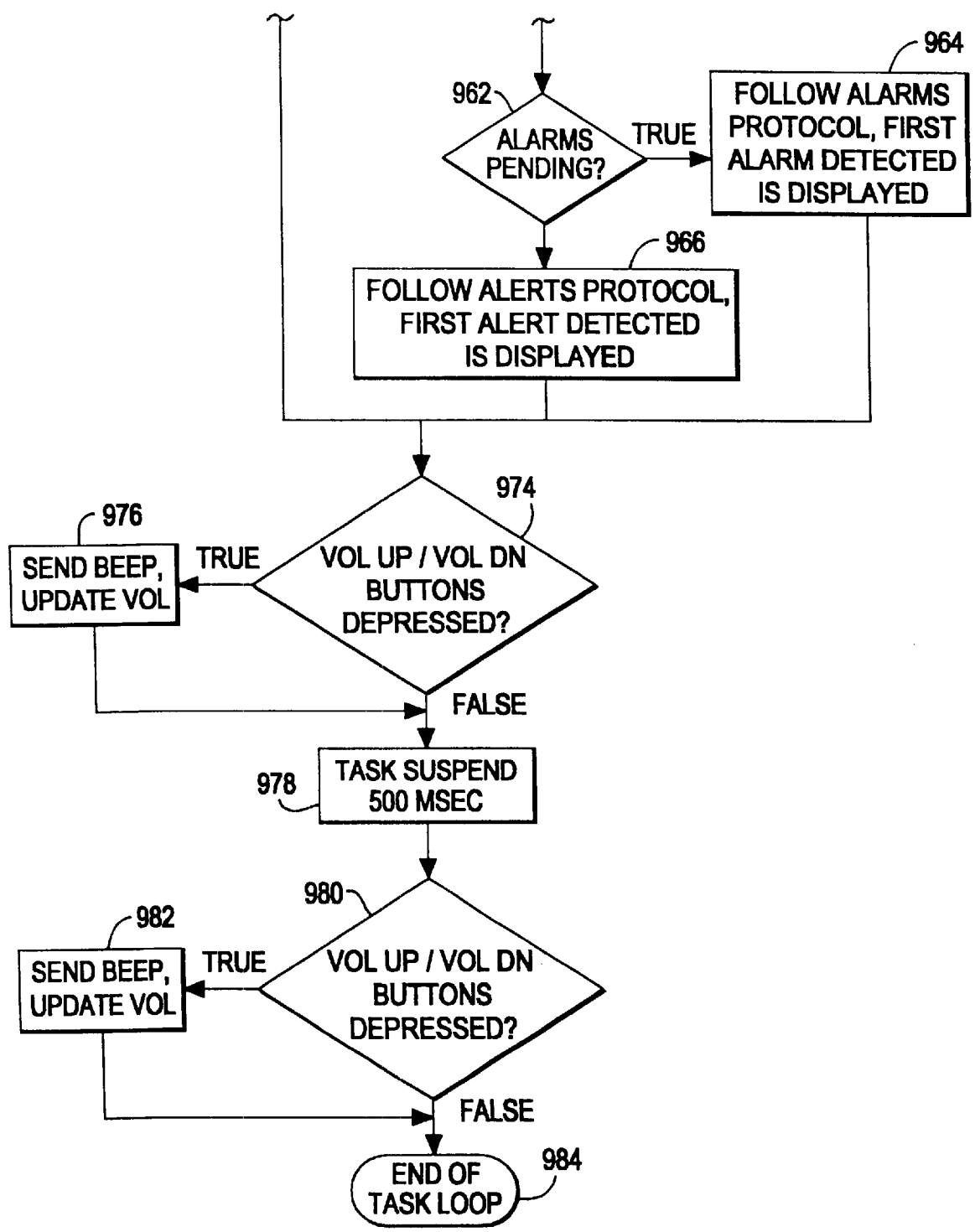

The message task flow chart is shown in FIGS. 19A–19B. When a message is queued to the message task, at step 940, the routine suspends the task for 450 milliseconds at step 942. At step 944 the routine enables the green "run" LED. At step 946 the routine checks for any pending alerts or alarms. If any are pending, the routine checks if the mute button is depressed at step 952. If yes, the routine enables an audio mute for two minutes at sep 954. If not, the routine activates the red "Alert/Alarm" LED at step 956. At step 958, the routine suspends the task for 50 milliseconds. At step 960 the routine deactivates the LEDs. At step 962 the routine checks if any alarms are pending. If true, the routine follows the alarms protocol at step 964. If not, the routine follows the alerts protocol in step 966.

If no alerts/alarms are pending, the routine checks if an event is in process at step 948. If true, the routine causes the message "Event in Progress" to be displayed on display 219 at step 950. If not, the routine causes the time of day to be displayed on display 219 at step 968. At step 970 the routine suspends the task for 50 milliseconds, then deactivates the LEDS at step 972.

At step 974 the routine checks if the volume buttons are depressed. If true, the routine causes a beep to be sent to the speaker and updates the volume register at step 976. If false, the routine suspends the task for 500 milliseconds at step 978. At step 980 the routine checks if the volume buttons have been depressed. If yes, the routine sends a beep and updates the volume register at step 982. If not, the routine ends at step 984.

Respiration Rate Algorithm: The respiration rate algorithm is designed to detect respiration by identifying temperature changes at the nostrils which are driven by the flow of air over the sensors. These temperature changes are converted into an estimation of respiration rate on a breath-by-breath basis. The Respiration Rate Calculation Algorithm uses a variant of the Smith Algorithm (A Simplified Approach to Peak Detection in Digitized Intrauterine Pressure Waveforms, Roger P. Smith, MD Biomedical Instrumentation & Technology, July 1989).

In the respiration rate algorithm, three detection windows are used to detect respiratory cycle peaks of a summed matrix of thermistors placed at the mouth and nose. The algorithm takes the time between each of the peaks and calculates breath rate per minute.

Figure 12:
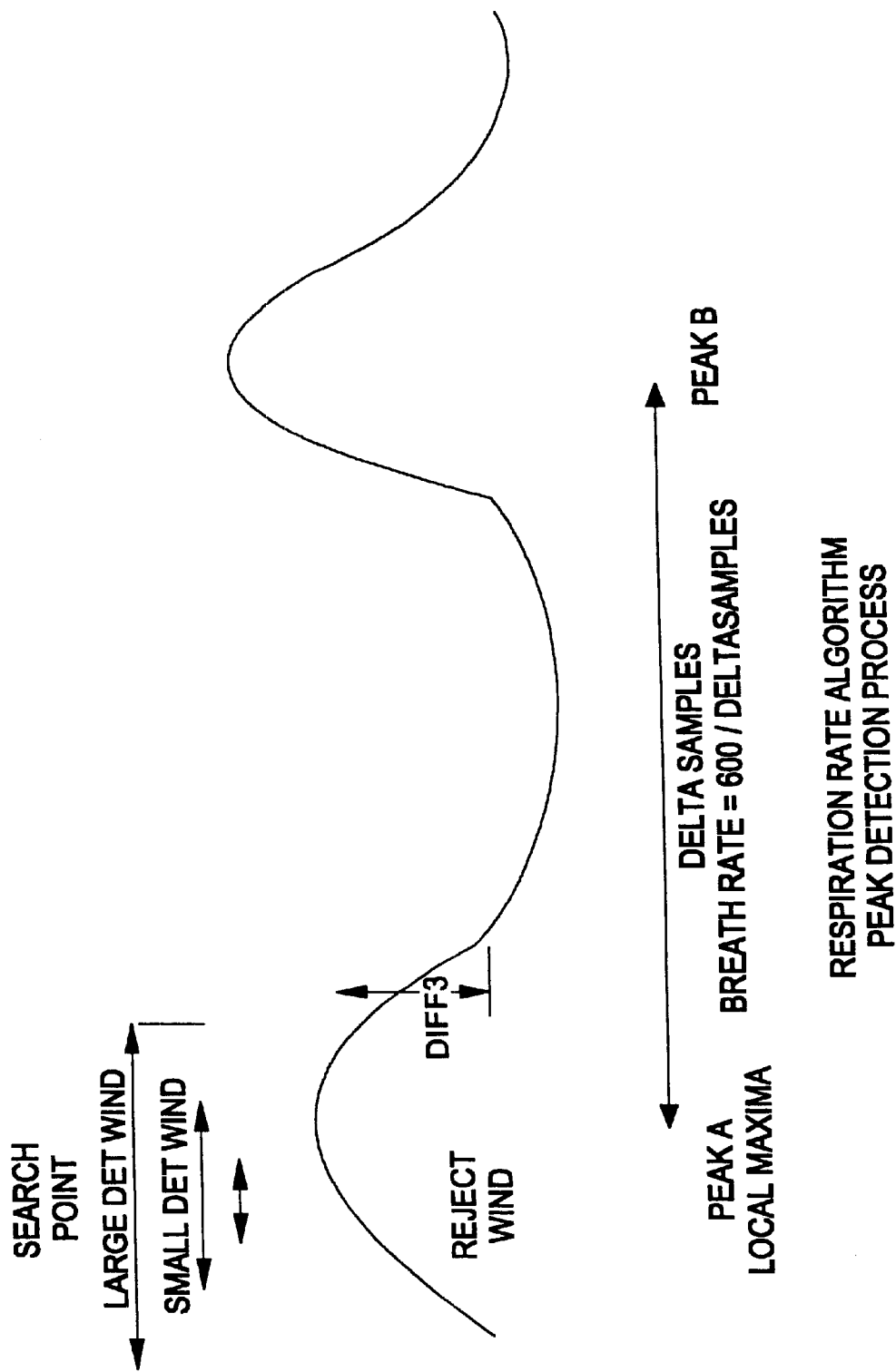
FIG. 12 is a waveform diagram of a single detection window used in the Smith Algorithm for respiration detection.

Referring to FIG. 12, the large Detection Window in the Smith Algorithm, represented in the waveform diagram contains a searchpoint, SP, which travels along the respiratory waveform, sample per sample. The window itself is a spread of N samples, with the SP situated in the center of the window. The window contains a difference parameter DIFF, expressed in digitized analog units or DAU, that is used at the boundaries of the window. The boundaries of the window are expressed as sample points $-N/2$ and $N/2$.

As the SP moves to each successive sample point of the waveform, the following test is performed: If the data at the SP minus the data found at sample $-N/2$ is greater than DIFF and if the data at the SP minus data found at sample $N/2$ is greater than DIFF, then this means that the window has encountered a peak in the waveform. Further, the local maxima of this peak lies between the SP and the sample $N/2$. After the local maxima is determined, then further SP testing is suspended until the SP moves to the past sample $N/2$ location. This is to prevent the algorithm from detecting again the same peak.

A counter, called SampleDelta, is used to accumulate the number of samples between local maximas of successive peaks. SampleDelta can then be converted into 20 the instantaneous respiratory (breath) rate per minute. To maintain stability of calculated respiratory rate a weighted respiratory function is used, which uses a chosen weight factor, a, to calculate the weighted respiratory rate as follows:

weighted respiratory rate (new)=weighted respiratory rate (old)*α+instantaneous respiratory rate*(1−α).

The constant, a, can be any number between 0 and 1.

Because respiratory rate can vary so widely, (from 4 to 40 breaths per second), several concurrent detection windows may be employed about the search point. Each window will have its own DIFF parameter. One window can be optimized to detect more slower peak waveforms, while another can be optimized to search for the faster peak waveforms. As a protection a rejection window can be employed, such if the peak is too narrow, it can be classified as a noise spike and ignored in the calculation process. Such is shown in the waveform diagram.

Figure 13A:
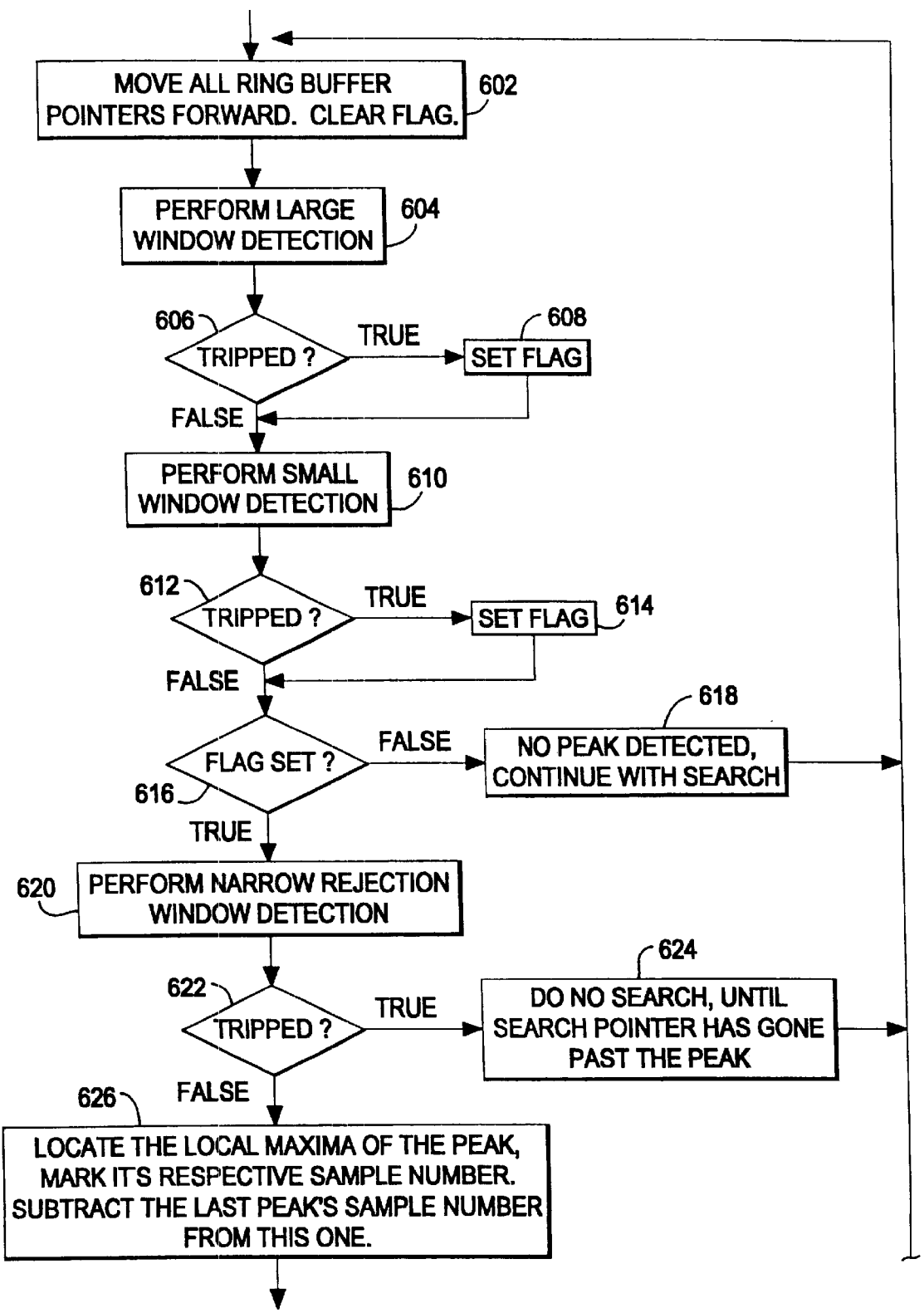
FIGS. 13A–13B are a flow chart of the respiratory data detection algorithm used in the ambulatory patient monitor to process respiratory data from the respiratory sensors.
Figure 13B:
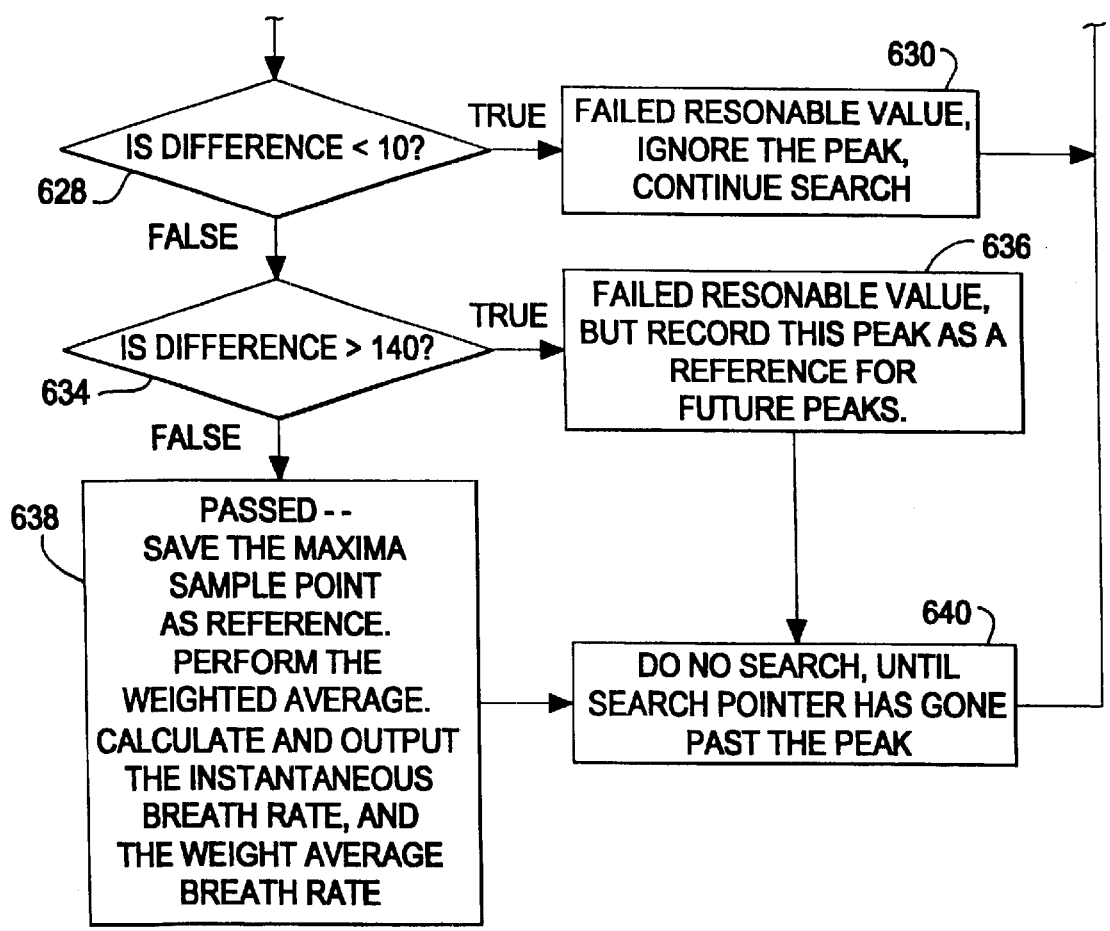

The three detection window algorithm as used in the patient ambulatory monitor 20 is shown in the flow diagram of FIGS. 13A–13B. After all ring buffer pointers are moved froward in step 602, the large window detection is performed in step 604. The routine checks if a peak is detected in step 606. If true, the peak detected flag is set in step 608. If false, the small window detection is performed in step 614. The routine checks if a peak is detected in step 612. If true, the peak detected flag is set in step 614. If false, the routine continues to step 616 where it checks for the peak flag set. If false, no peak is detected and the routine continues with the search at step 618 and returns to step 602. If a peak is found the routine performs the narrow rejection window detection in step 620 looking for the decrease in the value. At step 622 the routine checks for the peak. If the peak flag is still tripped, the routine stops the search at step 624 until the peak has been passed. If the search is past the peak, the routine locates the local maxima of the peak, marks the sample number and subtracts the last peak's sample number from the current one in step 626.

In step 628 the routine checks the value of the difference. If less than ten, indicating not a reasonable value, the peak is ignored and the search is continued at step 630. At step 634 the routine checks if the difference is greater than 140. If true, this also indicates not a reasonable value, but the peak is recorded for reference for future peak comparisons at step 636. If false, at step 638 the maxima sample point is saved as a reference. Now the routine performs the weighted average, calculates and outputs the instantaneous breath rate and the weighted average breath rate. At step 640 no search is performed until the peak has been passed. The routine loops until all data has been evaluated under the algorithm.

Remote Control Software

The caregiver can download stored data and send new Instructions from a remote location using remote control software. The remote control software can provide real-time interaction when the patient is dialed in and connected. It can review data stored in ambulatory patient monitor 20 or communications unit 30. It can schedule interactions between communications unit 30 and patient or clinician. The remote control software enables the caregiver to control the ambulatory patient monitor 20 through communications unit 30. Preferably the remote control software communicates with the communications unit 30 through modem to modem connection. The remote control software can store data pertaining to patient and settings/instructions for the ambulatory patient monitor 20 and communications unit 30. When connected to the communications unit 30, the remote control software can initiate measurements of sensors attached to communications unit 30. If not connected, the remote control software can dial up, establish a connection with the communications unit and order a specific measurement.

If the ambulatory patient monitor 20 is not connected to the communications unit 30, the remote control software can send a message to the communications unit to connect to the ambulatory patient monitor 20. Then it can send a message to make a measurement of a specific sensor attached to ambulatory patient monitor 20. Then the ambulatory patient monitor 20 makes the measurement, stores the data for the prescribed time period, transfers the data to the communications unit 30, then the communications unit 30 transmits the data to the remote control software.

Figure 20A:
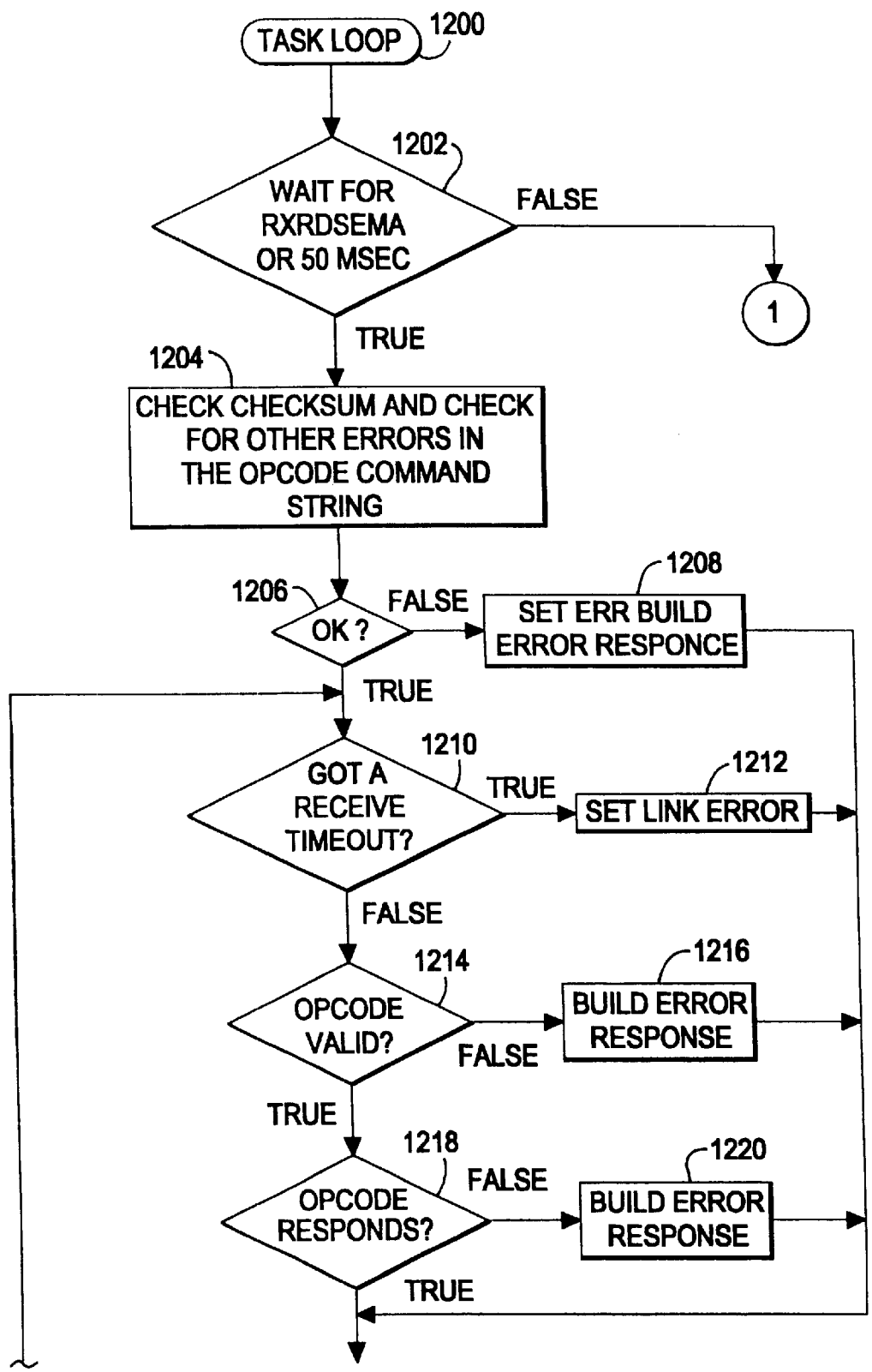
FIGS. 20A–20C are a flow chart of the communication link processing task in the ambulatory patient monitor and FIGS. 21A–21C are views of the core temperature shown in FIG. 3.
Figure 20B:
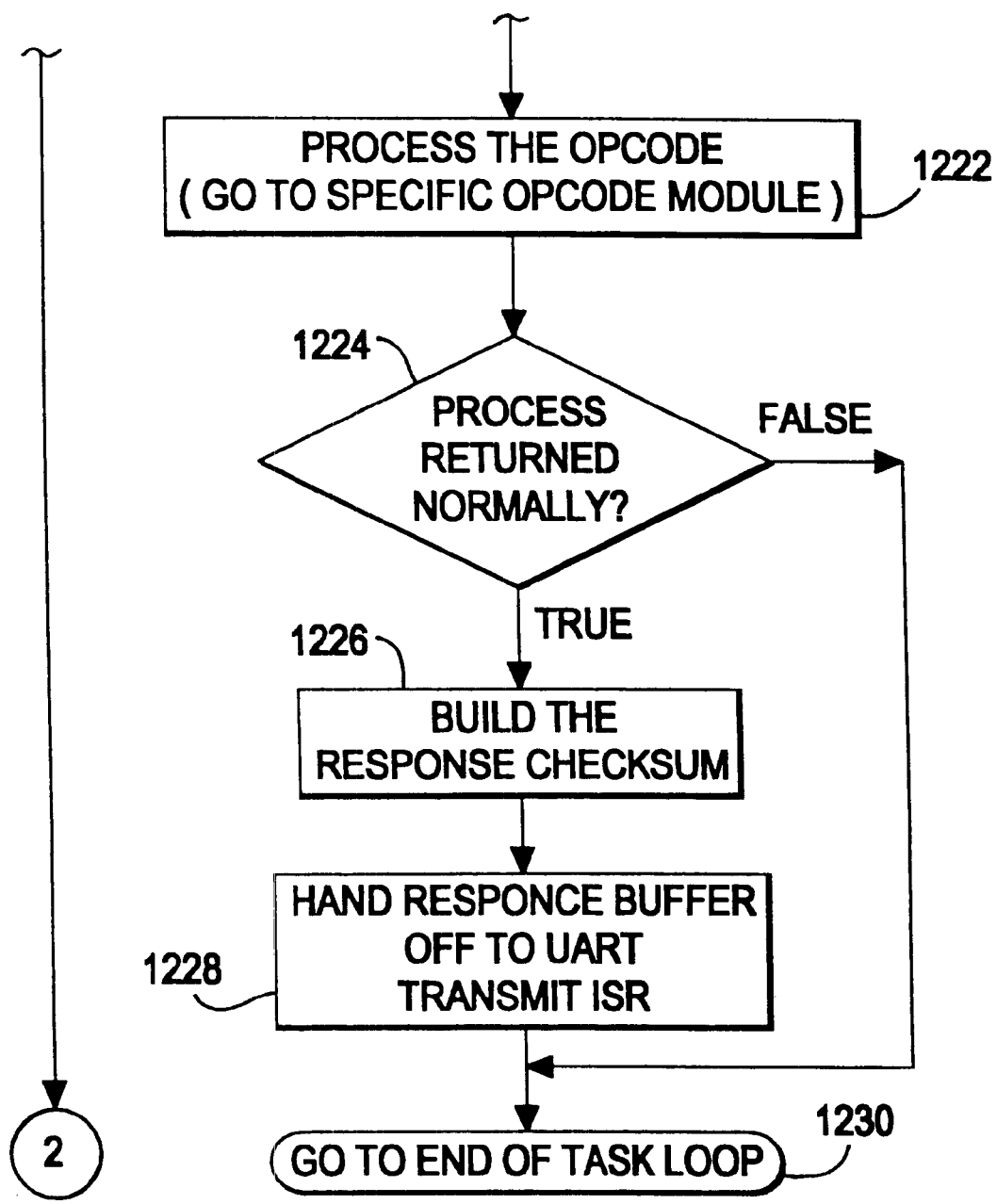
Figure 20C:
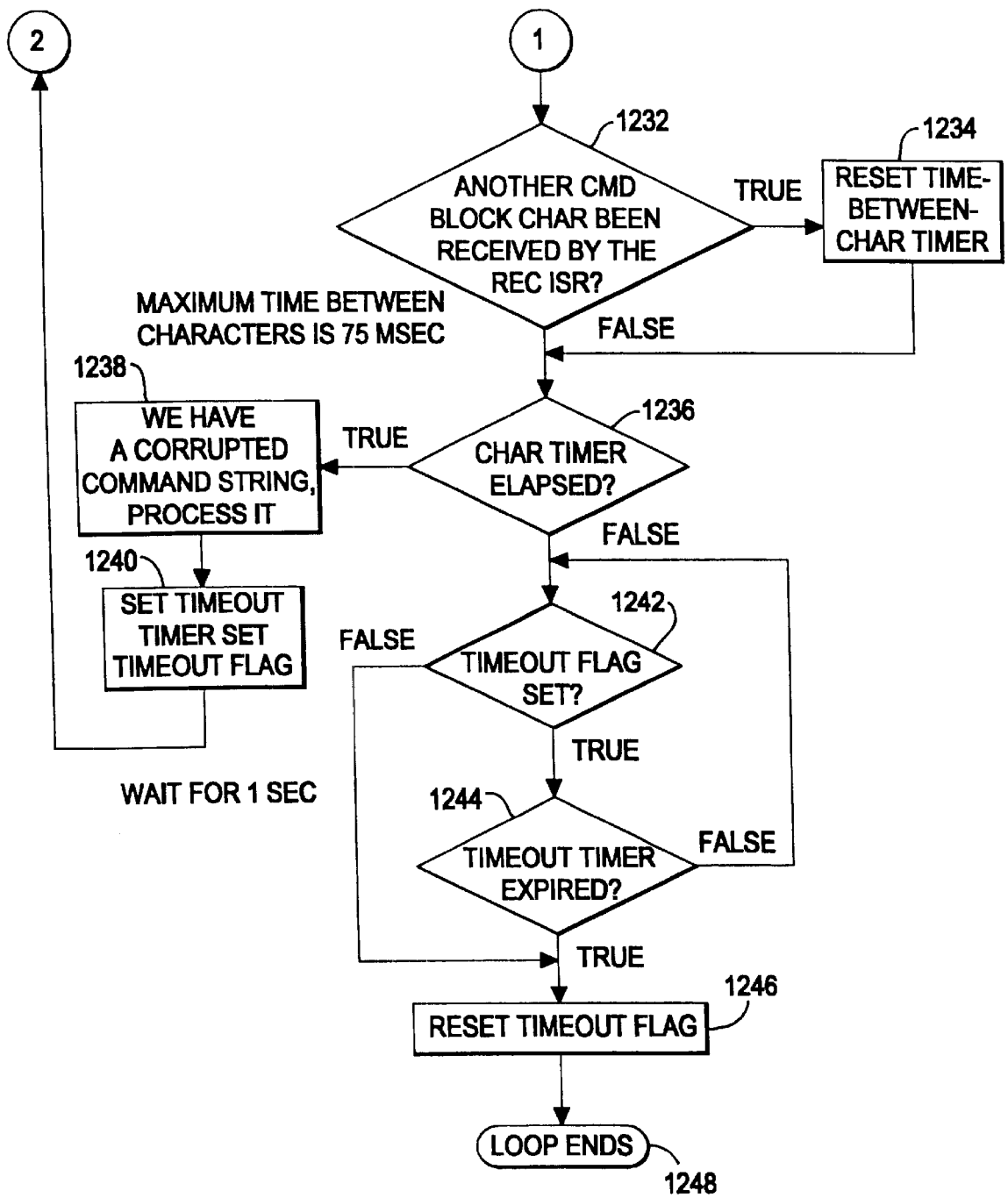

When the monitor 20 is connected to the communications unit and receives a communications signal, the microcontroller 201 executes the communications link task routine. Referring to FIGS. 20A–20C, the communication task begins at step 1200. At step 1202 the routine waits for the communication signal RXRDSEMA or 50 milliseconds. If this is false, the routine branches to step 1232. If true, the routine checks the checksum and for other errors in the data stream. If there are errors, the routine sets the error flag, builds the error response at step 1208 and continues to step 1222. If no errors, the routine checks for a receive timeout at step 1210. If true, the routine sets the error link at step 1212 and continues to step 1222. If false, the routine checks for a valid operations code at step 1218. If invalid, the routine builds a response at step 1220. If true the routine processes the opcode. Then the routine checks for normal process return at step 1224.

If the process return is not normal, the routine ends at step 1230. If the process routine is normal, the routine builds the response checksum at step 1224. At step 1228 the routine hands the response to the UART 225 and the loop ends at step 1230.

At step 1232 the routine checks for another command 30 character receipt. If true, the routine resets the time—between—character timer at step 1234. If false the routine checks for the char timer elapse. Maximum time between characters if 75 milliseconds. If true, the command string is corrupted and is processed at step 1238, then the timeout timer and timeout flag are set at step 1240 and the routine returns to step 1210. If false the routine checks for the timeout flag set at step 1242. If false, the routine resets the timeout flag at step 1246. If true, the routine checks for the timeout timer expired at step 1244. If false the routine returns to step 1242. If true, the routine resets the timeout flag at step 1246. The loop ends at step 1248.

While there has been illustrated and described a particular embodiment of the present invention, it will be appreciated that numerous changes and modifications will occur to those skilled in the art, and it is intended in the appended claims to cover all those changes and modifications which followed in the true spirit and scope of the present invention.

What is claimed is:

1. A method of detecting a respiration rate of a patient, comprising:

detecting temperature at the patient's nostrils, as a function of time, resulting from air flow over a temperature sensor;

periodically sampling peak temperature during a first detection window;

if no peak temperature is found during the first detection window, sampling peak temperature during a second detection window, wherein the second detection window is of a shorter duration than the first detection window;

if a peak temperature is found in either the first or second detection windows, sampling for a decrease in temperature from the peak temperature in a third detection window, wherein the third detection is of a shorter duration than the second detection window; and calculating the time difference between successive peak temperatures to obtain a breath rate per minute.

2. The method of claim 1, further comprising calculating a weighted respiratory rate in accordance with the relationship:

weighted respiratory rate (new)=weighted respiratory rate (old)*α+instantaneous respiratory rate*(1−α), where a is a constant number between 0 and 1.

* * * * *